(12) United States Patent
Thompson et al.

(10) Patent No.: US 12,139,526 B2
(45) Date of Patent: Nov. 12, 2024

(54) MODIFIED CHIMERIC RECEPTORS AND RELATED COMPOSITIONS AND METHODS

(71) Applicant: Juno Therapeutics, Inc., Seattle, WA (US)

(72) Inventors: Lucas James Thompson, Seattle, WA (US); Robert F. Dubose, Bellevue, WA (US); Archana Brahmandam, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1417 days.

(21) Appl. No.: 15/780,623

(22) PCT Filed: Dec. 2, 2016

(86) PCT No.: PCT/US2016/064861
§ 371 (c)(1),
(2) Date: May 31, 2018

(87) PCT Pub. No.: WO2017/096329
PCT Pub. Date: Jun. 8, 2017

(65) Prior Publication Data
US 2018/0355014 A1    Dec. 13, 2018

Related U.S. Application Data

(60) Provisional application No. 62/348,130, filed on Jun. 9, 2016, provisional application No. 62/262,911, filed on Dec. 3, 2015.

(51) Int. Cl.
| | | |
|---|---|---|
| *A61K 39/00* | (2006.01) | |
| *A61K 35/17* | (2015.01) | |
| *C07K 14/705* | (2006.01) | |
| *C07K 14/74* | (2006.01) | |
| *C12N 5/0783* | (2010.01) | |
| *C12N 5/10* | (2006.01) | |
| *A61K 35/66* | (2015.01) | |
| *A61P 35/00* | (2006.01) | |
| *A61P 35/04* | (2006.01) | |
| *A61P 37/00* | (2006.01) | |
| *C07K 7/06* | (2006.01) | |
| *C07K 9/00* | (2006.01) | |
| *C07K 16/28* | (2006.01) | |
| *C12N 15/62* | (2006.01) | |
| *C12N 15/86* | (2006.01) | |

(52) U.S. Cl.
CPC ........ *C07K 14/70539* (2013.01); *A61K 35/17* (2013.01); *C07K 14/705* (2013.01); *A61K 35/66* (2013.01); *A61P 35/00* (2018.01); *A61P 35/04* (2018.01); *A61P 37/00* (2018.01); *C07K 7/06* (2013.01); *C07K 9/00* (2013.01); *C07K 16/2812* (2013.01); *C07K 16/2815* (2013.01); *C07K 16/2818* (2013.01); *C07K 2317/56* (2013.01); *C07K 2317/622* (2013.01); *C07K 2319/03* (2013.01); *C07K 2319/033* (2013.01); *C12N 5/10* (2013.01); *C12N 15/62* (2013.01); *C12N 15/86* (2013.01)

(58) Field of Classification Search
None
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 4,795,698 A | 1/1989 | Owen |
| 5,087,616 A | 2/1992 | Myers et al. |
| 5,200,084 A | 4/1993 | Liberti |
| 5,219,740 A | 6/1993 | Miller |
| 6,040,177 A | 3/2000 | Riddell |
| 6,060,273 A | 5/2000 | Dirks et al. |

(Continued)

FOREIGN PATENT DOCUMENTS

| | | |
|---|---|---|
| CN | 103 483 453 | 1/2014 |
| CN | 104 583 230 | 4/2015 |

(Continued)

OTHER PUBLICATIONS

US 8,252,592 B2, 08/2012, Sadelain (withdrawn)

(Continued)

*Primary Examiner* — Michael Szperka
*Assistant Examiner* — Marianne DiBrino
(74) *Attorney, Agent, or Firm* — MORRISON & FOERSTER LLP

(57) ABSTRACT

Provided are chimeric receptors for engineering cells for adoptive therapy, including T cells, and the genetically engineered cells. In some embodiments, the chimeric receptors, such as chimeric antigen receptors (CARs) are modified in a junction region by one or more amino acid modifications such that peptide fragments of such region exhibit a lower binding affinity for a human leukocyte antigen (HLA) and/or the region exhibits reduced immunogenicity, including following administration to a subject. In some aspects, also provided are methods and compositions for engineering and producing cells expressing such chimeric receptors, compositions containing the cells, and method for their administration to subjects. In some embodiments, features of the chimeric receptors and engineered cells containing the chimeric receptors result in methods that provide for increased or improved activity, efficacy and/or persistence.

20 Claims, 14 Drawing Sheets
Specification includes a Sequence Listing.

(56) References Cited

U.S. PATENT DOCUMENTS

| | | |
|---|---|---|
| 6,207,453 B1 | 3/2001 | Maass |
| 6,410,319 B1 | 6/2002 | Raubitschek |
| 6,451,995 B1 | 9/2002 | Cheung |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain |
| 7,446,191 B2 | 11/2008 | Jensen |
| 7,855,268 B2 | 12/2010 | Atassi |
| 8,324,353 B2 | 12/2012 | Jensen |
| 8,389,282 B2 | 3/2013 | Sadelain |
| 8,399,645 B2 | 3/2013 | Campana |
| 8,497,118 B2 | 7/2013 | Jensen |
| 8,802,374 B2 | 8/2014 | Jensen |
| 8,822,647 B2 | 9/2014 | Jensen |
| 8,911,993 B2 | 12/2014 | June |
| 10,144,770 B2 * | 12/2018 | Campana ........... C07K 16/3084 |
| 11,266,739 B2 | 3/2022 | Gilbert |
| 2002/0131960 A1 | 9/2002 | Sadelain |
| 2002/0150914 A1 | 10/2002 | Andersen et al. |
| 2003/0170238 A1 | 9/2003 | Gruenberg |
| 2003/0191063 A1 | 10/2003 | Wraith et al. |
| 2005/0058643 A1 | 3/2005 | Wraith et al. |
| 2007/0128698 A1 | 6/2007 | Talor |
| 2007/0264229 A1 | 11/2007 | Strominger |
| 2010/0323966 A1 | 12/2010 | Wraith |
| 2011/0003380 A1 | 1/2011 | Miltenyi |
| 2012/0128586 A1 | 5/2012 | Calissano et al. |
| 2013/0149337 A1 | 6/2013 | Cooper |
| 2013/0156798 A1 | 6/2013 | Wraith et al. |
| 2013/0195900 A1 | 8/2013 | Dornmair et al. |
| 2013/0287748 A1 | 10/2013 | June |
| 2014/0271635 A1 | 9/2014 | Brogdon |
| 2014/0294841 A1 | 10/2014 | Scheinberg et al. |
| 2014/0348861 A1 | 11/2014 | Surolia et al. |
| 2015/0071967 A1 | 3/2015 | Wraith et al. |
| 2015/0139943 A1 | 5/2015 | Campana et al. |
| 2016/0158359 A1 | 6/2016 | Gilbert et al. |
| 2020/0297760 A1 | 9/2020 | Bonyhadi et al. |
| 2021/0284709 A1 | 9/2021 | Brandt et al. |
| 2024/0066122 A1 | 2/2024 | Gilbert et al. |

FOREIGN PATENT DOCUMENTS

| | | |
|---|---|---|
| CN | 104 910 279 | 9/2015 |
| CN | 106 163 547 | 11/2016 |
| EP | 0452342 | 10/1991 |
| EP | 1536826 | 9/2011 |
| EP | 2537416 | 12/2012 |
| EP | 3227323 | 10/2017 |
| EP | 3766895 | 1/2021 |
| JP | 2014-507118 | 3/2014 |
| JP | 2017/509621 | 4/2017 |
| JP | 2017-530694 | 10/2017 |
| WO | WO 1992/008796 | 5/1992 |
| WO | WO 1994/028143 | 12/1994 |
| WO | WO 1996/12737 | 5/1996 |
| WO | WO 1996/012737 | 5/1996 |
| WO | WO 2000/014257 | 3/2000 |
| WO | WO 2009/072003 | 6/2009 |
| WO | WO 2010/033140 | 3/2010 |
| WO | WO 2010/095031 | 8/2010 |
| WO | WO 2012/079000 | 6/2012 |
| WO | WO 2012/083069 | 6/2012 |
| WO | WO 2012/129514 | 9/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/011988 | 1/2014 |
| WO | WO 2014/031687 | 2/2014 |
| WO | WO 2014/055668 | 4/2014 |
| WO | WO 2014/144622 | 9/2014 |
| WO | WO 2014/153270 | 9/2014 |
| WO | WO 2015/131978 | 9/2015 |
| WO | WO 2015/142675 | 11/2015 |
| WO | WO 2015/184228 | 12/2015 |
| WO | WO 2016/028896 | 2/2016 |
| WO | WO 2016/069282 | 5/2016 |
| WO | WO 2016/090190 | 6/2016 |
| WO | WO 2016/146618 | 9/2016 |
| WO | WO 2017/064198 | 4/2017 |
| WO | WO 2017/093969 | 6/2017 |
| WO | WO 2017/096327 | 6/2017 |
| WO | WO 2018/067618 | 4/2018 |
| WO | WO 2019/070541 | 4/2019 |

OTHER PUBLICATIONS

Liu et al (Cancer Res., Sep. 2015, 75(17): 3596-3607) (Year: 2015).*
HLA Nomenclature (2015) (Year: 2015).*
Liu et al (Cancer Res. Sep. 1, 2015, 75(17): 3596-3607) (Year: 2015).*
Emboss Needle Alignment SEQ ID No. 5 (Year: 2022).*
Emboss Needle Alignment SEQ ID No. 137 (Year: 2022).*
Wieczorek et al (Front. Immunol. 2017, vol. 8, article 292: 1-16) (Year: 2017).*
Ochoa-Garay et al (Mol. Immunol. 1997, 34: 273-281) (Year: 1997).*
Stock et al (Int. J. Molec. Sci., 2019, 20, 6223, pp. 1-21) (Year: 2019).*
Hu et al (Protein Sci., 2007, 16: 2153-2165) (Year: 2007).*
Cheadle et al., "Natural expression of the CD19 antigen impacts the long-term engraftment but not antitumor activity of CD19-specic engineered T cells," J Immunol (2010) 184:1885-1896.
Davila et al., "How do CARs work ?: Early insights from recent clinical studies targeting CD19," Oncoimmunology (2012) 1(9):1577-1583.
Fry et al., "Clinical Activity and Persistence of Anti-CD22 Chimeric Antigen Receptor in Children and Young Adults with Relapsed/Refractory Acute Lymphoblastic Leukemia (ALL)," ASH, Dec. 2015; Retrieved from the Internet: //ash.confex.com/ash/2015/webprogram/Paper86307.html [retrieved Nov. 23, 2015].
Geiger et al., "Human naive and memory CD4+ T cell repertoires specific for naturally processed antigens analyzed using libraries of amplified T cells," J Exp Med (2009) 206(7):1525-1534.
Gertel et al., "Immune tolerance induction with multipitope peptide derived from citrullinated autoantigens attenuates arthritis manifestations in adjuvant arthrtis rats," J Immunol (2015) 194(12):5674-5680.
Gill et al., "CAR-modified anti-CD19 T cells for the treatment of B-cell malignancies: rules of the road," Expert Opinion on Biological Therapy (2014) 14(1):37-49.
Grupp et al., "Chimeric antigen receptor-modified T cells for acute lymphoid leukemia," N. Engl. J. Med. (2013) 368:1509-1518.
Haso et al., "Anti-CD22-chimeric antigen receptors targeting B-cell precursor acute lymphoblastic leukemia," Blood. (2013) 121(7):1165-1174.
Long et al., "Lessons learned from a highly-active CD22-specific chimeric antigen receptor," Oncolmmunology (2013) 2(4):e23641.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.
Arstila et al., "A Direct Estimate of the Human αβ T Cell Receptor Diversity," Science (1999) 286:958-961.
Barrett et al., "Chimeric Antigen Receptor Therapy for Cancer," Annual Review of Medicine (2014) 65:333-347.
Berger et al., "Analysis of transgene-specific immune responses that limit the in vivo persistence of adoptively transferred HSV-TK-modified donor T cells after allogeneic hematopoietic cell transplantation," Blood. Mar. 15, 2006;107(6):2294-302.
Berger et al., "Cutaneous T-cell lymphoma: malignant proliferation of T-regulatory cells," Blood. Feb. 15, 2005;105(4):1640-7.

(56) References Cited

OTHER PUBLICATIONS

Berger et al., "Nonmyeloablative immunosuppressive regimen prolongs In vivo persistence of gene-modified autologous T cells in a nonhuman primate model," J Virol. Jan. 2001;75(2):799-808.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7:2031-2034.

Brusic et al., "Prediction of MHC class II-binding peptides using an evolutionary algorithm and artificial neural network," Bioinformatics. (1998) 14:121-131.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10):1137-46.

Cavalieri et al., "Human T lymphocytes transduced by lentiviral vectors in the absence of TCR activation maintain an intact immune competence," Blood (2003) 102(2):497-505.

Cheadle et al., "Chimeric antigen receptors for T-cell based therapy," Methods Mol Biol (2012) 907:645-666.

Chicaybam et al., "An efficient low cost method for gene transfer to T lymphocytes," PLoS One (2013) 8(3):e60298.

Chmielewski et al., "Antigen-Specific T-Cell Activation Independently of the MHC: Chimeric Antigen Receptor-Redirected T Cells," Front Immunol. Nov. 11, 2013;4:371.

Cho et al., "Human mammalian cell sorting using a highly integrated micro-fabricated fluorescence-activated cell sorter (microFACS)," Lab Chip (2010) 10:1567-1573.

Clackson et al., "Making antibody fragments using phage display libraries," Nature (1991) 352:624-628.

Cohen et al., "Recombinant antibodies with MHC-restricted, peptide-specific, T-cell receptor-like specificity: new tools to study antigen presentation and TCR-peptide-MHC interactions," J Mol Recogn (2003) 16:324-332.

Cooper et al., "T-cell clones can be rendered specific for CD19: toward the selective augmentation of the graft-versus-B-lineage leukemia effect," Blood. (2003) 101:1637-1644.

Davila et al., "CD19 CAR-targeted T cells induce long-term remission and B Cell Aplasia in an immunocompetent mouse model of B cell acute lymphoblastic leukemia," PLoS One (2013) 8(4):e61338.

De Jesus et al., "The role of tryptophan side chains in membrane protein anchoring and hydrophobic mismatch," Biochim Biophys Acta. Feb. 2013;1828(2):864-76.

Ettinger et al., "A peptide binding motif for HLA-DQA1*0102/ DQB1*0602, the class II MHC molecule associated with dominant protection in insulin-dependent diabetes mellitus," J Immunol. Mar. 1, 1998;160(5):2365-73.

Fedorov et al., "PD-1- and CTLA-4-based inhibitory chimeric antigen receptors (iCARs) divert off-target immunotherapy responses," Sci. Transl. Medicine (2013) 5(215).

Fry et al., "T-cell adoptive immunotherapy for acute lymphoblastic leukemia," Hematology Am Soc Hematol Educ Program. (2013);2013:348-53.

Hermans et al., "The Vital assay: a versatile fluorometric technique for assessing CTL- and NKT-mediated cytotoxicity against multiple targets in vitro and in vivo," J. Immunological Methods (2004) 285(1):25-40.

Hilderbrand et al., "Structural features of transmembrane helices," FEBS Letters (2004) 559:145-151.

Honeyman et al., "Neural network-based prediction of candidate T-cell epitopes," Nat Biotechnol. Oct. 1998;16(10):966-9.

Huang et al., "DNA transposons for modification of human primary T lymphocytes," Methods Mol Biol (2009) 506:115-126.

Hudecek et al., "Receptor affinity and extracellular domain modifications affect tumor recognition by ROR1-specific chimeric antigen receptor T cells," Clin. Cancer Res. (2013) 19:3153-3164.

Jena et al., "Chimeric antigen receptor (CAR)-specific monoclonal antibody to detect CD19-specific T cells in clinical trials," PLoS One. (2013);8(3):e57838.

Johnston, et al., "Biolistic transformation: microbes to mice," Nature (1990) 346:776-777.

Karosiene et al., "NetMHCIIpan-3.0, a common pan-specific MHC class II prediction method including all three human MHC class II isotypes, HLA-DR, HLA-DP and HLA-DQ," Immunogenetics. Oct. 2013;65(10):711-24.

Kim et al., "Immune epitope database analysis resource," Nucleic Acids Res. Jul. 2012;40(Web Server issue):W525-30.

Klebanoff et al., "Sorting through subsets: which T-cell populations mediate highly effective adoptive immunotherapy?," J Immunother. (2012) 35(9):651-660.

Kochenderfer et al., "Construction and preclinical evaluation of an anti-CD19 chimeric antigen receptor," J. Immunotherapy (2009) 32(7):689-702.

Koste et al., "T-cell receptor transfer into human T cells with ecotropic retroviral vectors," Gene Therapy (2014) 21:533-538.

Kutler et al., "An algorithm for the prediction of proteasomal cleavages," J Mol Biol. May 5, 2000;298(3):417-29.

Lafuente et al., "Prediction of MHC-peptide binding: a systematic and comprehensive overview," Curr Pharm Des. (2009);15(28):3209-20.

Lamers et al., "Immune responses to transgene and retroviral vector in patients treated with ex vivo-engineered T cells," Blood (2011) 117:72-82.

Lucienne, "CD3-specific antibodies as promising tools to aim at immune tolerance in the clinic," Int Rev Immunol. May-Aug. 2006;25(3-4):215-33.

Lundegaard et al., "NetMHC-3.0: accurate web accessible predictions of human, mouse and monkey MHC class I affinities for peptides of length 8-11," Nucl. Acids Res. (2008);36 (suppl 2):W509-W512.

Lupton S. D. et al., "Dominant positive and negative selection using a hygromycin phosphotransferase-thymidine kinase fusion gene," Mol. and Cell Biol. (1991) 11:6.

Manuri et al., "piggyBac transposon/transposase system to generate CD19-specific T cells for the treatment of B-lineage malignancies," Hum Gene Ther (2010) 21(4):427-437.

Miller et al., "Improved retroviral vectors for gene transfer and expression," BioTechniques (1989) 7:980-990.

Miller et al., "Retrovirus packaging cells," Human Gene Therapy (1990) 1:5-14.

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.

Nielsen et al., "Quantitative predictions of peptide binding to any HLA-DR molecule of known sequence: NetMHCIIpan," PLoS Comput Biol. Jul. 4, 2008;4(7):e1000107.

Nielsen et al., "Reliable prediction of T-cell epitopes using neural networks with novel sequence representations," Protein Sci. (2003);12:1007-1017.

Nussbaum et al., "PAProC: a prediction algorithm for proteasomal cleavages available on the WWW," Immunogenetics. Mar. 2001;53(2):87-94.

Park et al., "Treating cancer with genetically engineered T cells," Trends Biotechnol. (2011) 29(11):550-557.

Parker et al., "Scheme for ranking potential HLA-A2 binding peptides based on independent binding of individual peptide side-chains," J Immunol. Jan. 1, 1994;152(1):163-75.

Pegram et al., "CD28z CARs and armored CARs," Cancer J. Mar.-Apr. 2014;20(2):127-33.

Peters et al., "Generating quantitative models describing the sequence specificity of biological processes with the stabilized matrix method," BMC Bioinformatics. May 31, 2005;6:132.

Peters et al., "The immune epitope database and analysis resource: From vision to blueprint.," PLoS Biol (2005);3(3):379-381.

(56) References Cited

OTHER PUBLICATIONS

Portolano et al., "Lack of promiscuity in autoantigen-specific H and L chain combinations as revealed by human H and L chain "roulette"," J Immunol (1993) 150(3):880-887.
Rammensee et al., "SYFPEITHI: database for MHC ligands and peptide motifs," Immunogenetics. Nov. 1999;50(3-4):213-9.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Riddell et al., "T-cell mediated rejection of gene-modified HIV-specific cytotoxic T lymphocytes in HIV-infected patients," Nature Medicine (1996) 2, 216-223.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4):388-398.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloney-based vectors in ecotropic and amphotropic packaging cell lines," Virology (1991) 180:849-852.
Sette et al., "Peptide binding to the most frequent HLA-A class I alleles measured by quantitative molecular binding assays," Mol Immunol. Aug. 1994;31(11):813-22.
Shaffer et al., "Foreign or Domestic CARs: Receptor Ligands as Antigen-Binding Domains," Med. Sci. (2014), 2(1), 23-36.
Sharma et al., "Efficient sleeping beauty DNA transposition from DNA minicircles," Molec Ther Nucl Acids (2013) 2, e74.
Sidney et al., "Quantitative peptide binding motifs for 19 human and mouse MHC class I molecules derived using positional scanning combinatorial peptide libraries," Immunome Res. Jan. 25, 2008;4:2.
Solberg et al., "Balancing selection and heterogeneity across the classical human leukocyte antigen loci: a meta-analytic review of 497 population studies," Hum Immunol. Jul. 2008;69(7):443-64.
Southwood et al., "Several common HLA-DR types share largely overlapping peptide binding repertoires," J Immunol. Apr. 1, 1998;160(7):3363-73.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10):928-933.
Tsukahara et al., "CD19 target-engineered T-cells accumulate at tumor lesions in human B-cell lymphoma xenograft mouse models," Biochem Biophys Res Commun (2013) 438(1):84-9.
Turtle et al., "Engineered T cells for anti-cancer therapy," Curr. Opin. Immunol. (2012) 24(5):633-39.
Van Tendeloo et al., "High-level transgene expression in primary human T lymphocytes and adult bone marrow CD34+ cells via electroporation-mediated gene delivery," Gene Therapy (2000) 7(16):1431-1437.
Verhoeyen et al., "Lentiviral vector gene transfer into human T cells," Methods Mol Biol. (2009) 506:97-114.
Wadhwa et al., "Receptor mediated glycotargeting," J. Drug Targeting (1995) 3:111.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1977) 11(1):223-232.
Wu et al., "Adoptive T-cell therapy using autologous tumor-infiltrating lymphocytes for metastatic melanoma: current status and future outlook," Cancer (2012) 18(2):160-75.
Wu et al., "Remote control of therapeutic T cells through a small molecule-gated chimeric receptor," Science (2015) 350(6258):aab4077.

Zhang et al., "TEPITOPEpan: extending TEPITOPE for peptide binding prediction covering over 700 HLA-DR molecules," PLoS One. (2012);7(2):e30483. doi: 10.1371/journal.pone.0030483.
Zhao et al., "Structural Design of Engineered Costimulation Determines Tumor Rejection Kinetics and Persistence of Car T Cells," Cancer Cell (2015) 28(4):415-428.
NCI Clinical Trial Identifier NCT02315612, dated Nov. 11, 2015. Retrieved from https://clinicaltrials.gov/ct2/history/NCT02315612?V_9=View#StudyPageTop.
Newberg et al., "Importance of MHC Class I α2 and α3 Domains in the Recognition of Self and Non-Self MHC Molecules The Journal of Immunology (1996) 156(7):2473-2480.
United States Securities and Exchange Commission, "Annual Report Pursuant To Section 13 OR 15(d) Of the Securities Exchange Act Of 1934," signed Mar. 18, 2015.
Geneseq Accession No. AGD24541, dated Jan. 25, 2013. Retrieved from Sequence 21997 from patent U.S. Pat. No. 8,343,764—Protein—NCBI (nih.gov).
Baker et al., "Immunogenicity of protein therapeutics," Self/Nonself (2010) 1(4):314-322.
Draper et al., "Targeting of HPV-16+ Epithelial Cancer Cells by TCR Gene Engineered T Cells Directed against E6," Clinical Cancer Research, (2015) 21(19):4431-4439.
Dubois et al., "Tolerant CD8 T Cells Induced by Multiple Injections of Peptide Antigen Show Impaired TCR Signaling and Altered Proliferative Responses In Vitro and In Vivo," J Immunol (1998) 161:5260-5267.
Fandrich et al., "Different in vivo tolerogenicity of MHC class I peptides," Journal of Leukocyte Biology (1999) 65:16-27.
Hardet et al., "Oral-tolerization Prevents Immune Responses and Improves Transgene Persistence Following Gene Transfer Mediated by Adeno-associated Viral Vector," Mol Ther (2016) 24(1):87-95.
Haso et al., "CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared To Those Containing CD28," Blood (2013) 22(21):1431.
Jensen et al., "Antitransgene rejection responses contribute to attenuated persistence of adoptively transferred CD20/CD19-specific chimeric antigen receptor redirected T cells in humans," Biol Blood Marrow Transplant. Sep. 2010; 16(9):1245-1256.
Lee et al., "T cells expressing CD19 chimeric antigen receptors for acute lymphoblastic leukaemia in children and young adults: a phase 1 dose-escalation trial," Lancet (2015) 385(9967): 517-528.
Mack et al. "Common and well-documented HLA alleles: 2012 update to the CWD catalogue," Tissue Antigens (2013) 81:194-203.
Makkouk et al., "Cancer Immunotherapy and Breaking Immune Tolerance: New Approaches to an Old Challenge," Cancer Res (2015) 75(1):5-10.
Mariuzza et al., The structural basis of antigen-antibody recognition, Ann. Rev. Biophys. Biophys. Chem., 1987, vol. 16, pp. 139-159.
Maude et al., "Chimeric antigen receptor T cells for sustained remissions in leukemia," N Engl J Med. (2014) 371(16): 1507-1517.
Newberg et al., Importance of MHC Class I α2 and α3 Domains in the Recognition of Self and Non-Self MHC Molecules The Journal of Immunology (1996) 156(7):2473-2480.
Osborn et al., "Evaluation of TCR Gene Editing Achieved by TALENs, CRISPR/Cas9, and megaTAL Nucleases," Mol. Ther., (2016) 24(3):570-581.
Salyaev et al. "The study of immunogenicity of the antigenic protein of high risk oncogenic type of the human papillomavirus HPV16 L1 produced in the plant expression system on the base of transgenic tomato." Doklady Biochemistry and Biophysics. vol. 474. No. 1. Pleiades Publishing, 2017. 186 abstract.
Toes et al., "Enhancement of Tumor Outgrowth Through CTL Tolerization After Peptide Vaccination Is Avoided by Peptide Presentation on Dendritic Cells," J. Immunol (1998) 160:4449-4456.
Abate-Daga et a;., "CAR models: next-generation CAR modifications for enhanced T-cell function," Mol Ther Oncol (2016) 3:16014.
Aidoo et al., "Identification of conserved antigenic components for a cytotoxic T lymphocyte-inducing vaccine against malaria," Lancet (1995) 345:1003-1007.

(56) References Cited

OTHER PUBLICATIONS

Banu et al., "Building and Optimizing a Virus-specific T Cell Receptor Library for Targeted Immunotherapy in Viral Infections" Scientific Reports (2014) 4:1-10.
Bhasin et al., "MHCBN: a comprehensive database of MHC binding and non-binding peptides," Bioinformatics (2003) 19(5):665-666.
Brunner et al., "Cytotoxic T cells: Double-barreled shot guns," Nature Medicine (1999) vol. 5, N. 1, abstract.
Celis et al., "Identification of Potential CTL Epitopes of Tumor-associated Antigen Mage-1 for Fice Common HLA-A Alleles," Mol Immunol (1994) 31(18) 1423-1430.
Koyko et al., Immunology translation from English, edited by N.B. Serebryanaya, Moscow, "Akademiya", 2008, p. 37.
Eyquem et al., "Targeting a CAR to the TRAC locus with CRISPR/Cas9 enhances tumour rejection", Nature (2017) 543(7643):113-117.
HLA Nomenclature "HLA Alleles Numbers," Retrieved on Sep. 27, 2023 from //hla.alleles.org/nomenclature/stats.html, pp. 1-2.
Li et al., "Adena-associated virus vectors: potential applications for cancer gene therapy" Cancer Gene Therapy (2005) 12:913-925.
Liu et al., "Major Histocompatibility complex: interaction with peptides," IN: eLS. John Wiley & Sons, Ltd: Chichester, DOI: 10.1002/9780470015902. a0000922.pub2, 2011, pp. 1-12) (Year: 2011).
Liu et al in "Rapid induction of cytotoxic T-cell response against cervical cancer cells by human papillomavirus type 16 E6 antigen gene delivery into human dendritic cells by an adeno-associated virus vector" Cancer Gene Therapy (2001) 8(12):948-957.
Monjezi et al., "Enhanced CAR T-cell engineering using non-viral Sleeping Beauty transposition from minicircle vectors" Leukemia (2017) 31:186-194.
Munoz et al., "Epidemiologic Classification of Human Papillomavirus Types Associated with Cervical Cancer," N Engl J Med (2003) 348(6):518-527 abstract.
Roitt et al., Immunology (2000) pp. 4-6 with translation.
Schumann et al., "Generation of knock-in primary human T cells using Cas9 ribonucleoproteins," Proceedings of the National Academy of Sciences (2015) 112(33):10437-10442.
Wagner et al., "Immunogenicity of CAR T cells in cancer therapy," Nature Reviews (2021) 18:379-393.
Wieczorek et al., "Major Histocompatibility Complex (MHC) Class I and MHC Class II Proteins: Conformational Plasticity in Antigen Presentation," Front Immunol (2017) 9:Article 292, pp. 1-16.
Kehrl et al., "Molecular mechanisms regulating CD19, CD20 and CD22 gene expression," Immunol Today. (1994) 15(9):432-436.
Raponi et al., "Flow cytometric study of potential target antigens (CD19, CD20, CD22, CD33) for antibody-based immunotherapy in acute lymphoblastic leukemia: analysis of 552 cases," Leuk Lymphoma. (2011) 52(6):1098-107.

\* cited by examiner

FIG. 6

```
            CD28 transmembrane domain  ←·· ── ·· ── ·· ── Junction Region ── ·· ──→
FWVLVVVGGV  LACYSLLVTV  AFIIFWVKRG                                    30

── ·· ── ·· ──→         4-1BB costimulatory domain
RKKLLYIFKQ  PFMRPVQTTQ  EEDGCSCRFP                                    60

── ── ── ──→
EEEEGGCEL                                                             69
```

SEQ ID NO: 5

FIG. 7   % Potential Impact in the Population Based on REVEAL® Score

SEQUENCE LISTING

<160> NUMBER OF SEQ ID NOS: 184

<210> SEQ ID NO 1
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: IgG4 hinge

<400> SEQUENCE: 1

Glu Ser Lys Tyr Gly Pro Pro Cys Pro Cys Pro
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Synthetic
<220> FEATURE:
<223> OTHER INFORMATION: CD28 transmembrane domain

<400> SEQUENCE: 2

```
Phe Trp Val Leu Val Val Gly Gly Val Leu Ala Cys Tyr Ser Leu
1               5                   10                  15

Leu Val Thr Val Ala Phe Ile Ile Phe Trp Val
                20                  25
```

```
<210> SEQ ID NO 3
<211> LENGTH: 42
<212> TYPE: PRT
<213> ORGANISM: Homo sapiens
<220> FEATURE:
<223> OTHER INFORMATION: 4-1BB costimulatory domain

<400> SEQUENCE: 3
```

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

```
<210> SEQ ID NO 4
<211> LENGTH: 112
<212> TYPE: PRT
<213> ORGANISM: Artificial Sequence
<220> FEATURE:
<223> OTHER INFORMATION: Synthetic
<220> FEATURE:
<223> OTHER INFORMATION: CD3-zeta intracellular signaling domain

<400> SEQUENCE: 4
```

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 5
<211> LENGTH: 69
<212> TYPE: PRT
<213> ORGANISM: Artificial Sequence
<220> FEATURE:
<223> OTHER INFORMATION: Synthetic
<220> FEATURE:
<223> OTHER INFORMATION: CD28-4-1BB

<400> SEQUENCE: 5
```

```
Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
                20                  25                  30

Lys Leu Leu Tyr Ile Phe Lys Gln Pro Phe Met Arg Pro Val Gln Thr
            35                  40                  45
```

```
Thr Gln Glu Glu Asp Gly Cys Ser Cys Arg Phe Pro Glu Glu Glu
    50                  55                  60

Gly Gly Cys Glu Leu
65

<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

Cys Tyr Ser Leu Leu Val Thr Val Ala Phe Ile Ile Phe Trp Val Lys
1               5                   10                  15

Arg Gly Arg Lys Lys Leu Leu Tyr Ile Phe Lys Gln Pro Phe
            20                  25                  30

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Val Ala Phe Ile Ile Phe Trp Val Lys Arg Gly Arg Lys Lys Leu Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Phe Ile Ile Phe Trp Val Lys Arg Gly Arg Lys Lys Leu Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Phe Trp Val Lys Arg Gly Arg Lys Lys Leu Leu Tyr Ile Phe Lys
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Phe Ile Ile Phe Trp Val Lys Arg Gly Arg Lys Lys Leu Leu
1               5                   10

<210> SEQ ID NO 11
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 11

Phe Ile Ile Phe Trp Val Lys Arg Gly Arg Lys Lys Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ile Ile Phe Trp Val Lys Arg Gly Arg Lys Lys Leu Leu
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: Variant junction region

<400> SEQUENCE: 13

Cys Tyr Ser Leu Leu Val Thr Val Ala Phe Ile Ile Phe Trp Val Asn
1               5                   10                  15

Asn Lys Arg Gly Arg Lys Lys Leu Leu Tyr Ile Phe Lys Gln Pro Phe
            20                  25                  30

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: Variant peptide

<400> SEQUENCE: 14

Ile Ile Phe Trp Val Asn Asn Lys Arg Gly Arg Lys Lys Leu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: Variant peptide

<400> SEQUENCE: 15

Ile Ile Phe Trp Val Asn Asn Lys Arg Gly Arg Lys Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16
```

Val Ala Phe Ile Ile Phe Trp Val Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Ala Phe Ile Ile Phe Trp Val Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Phe Ile Ile Phe Trp Val Lys Arg Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Ile Ile Phe Trp Val Lys Arg Gly Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Ile Phe Trp Val Lys Arg Gly Arg Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Phe Trp Val Lys Arg Gly Arg Lys Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Trp Val Lys Arg Gly Arg Lys Lys Leu

```
<210> SEQ ID NO 23
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 23

Val Ala Phe Ile Ile Phe Trp Val Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 24

Ala Phe Ile Ile Phe Trp Val Ser Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 25

Phe Ile Ile Phe Trp Val Ser Arg Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 26

Ile Ile Phe Trp Val Ser Arg Gly Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 27

Ile Phe Trp Val Ser Arg Gly Arg Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 28

Phe Trp Val Ser Arg Gly Arg Lys Lys
1               5
```

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 29

Trp Val Ser Arg Gly Arg Lys Lys Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 30

Val Ala Phe Ile Ile Phe Trp Val Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 31

Ala Phe Ile Ile Phe Trp Val Leu Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 32

Phe Ile Ile Phe Trp Val Leu Arg Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 33

Ile Ile Phe Trp Val Leu Arg Gly Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 34

Ile Phe Trp Val Leu Arg Gly Arg Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 35

Phe Trp Val Leu Arg Gly Arg Lys Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 36

Trp Val Leu Arg Gly Arg Lys Lys Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 37

Val Ala Phe Ile Ile Phe Trp Val His
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 38

Ala Phe Ile Ile Phe Trp Val His Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 39

Phe Ile Ile Phe Trp Val His Arg Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 40

Ile Ile Phe Trp Val His Arg Gly Arg
1               5

```
<210> SEQ ID NO 41
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 41

Ile Phe Trp Val His Arg Gly Arg Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 42

Phe Trp Val His Arg Gly Arg Lys Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 43

Trp Val His Arg Gly Arg Lys Lys Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 44

Val Ala Phe Ile Ile Phe Trp Val Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 45

Ala Phe Ile Ile Phe Trp Val Ala Arg
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 46

Ile Ile Phe Trp Val Ala Arg Gly Arg
1               5

<210> SEQ ID NO 47
```

```
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 47

Ile Phe Trp Val Ala Arg Gly Arg Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 48

Phe Trp Val Ala Arg Gly Arg Lys Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 49

Trp Val Ala Arg Gly Arg Lys Lys Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 50

Val Ala Phe Ile Ile Phe Trp Val Gln
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 51

Ala Phe Ile Ile Phe Trp Val Gln Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 52

Phe Ile Ile Phe Trp Val Gln Arg Gly
1               5

<210> SEQ ID NO 53
<211> LENGTH: 9
```

```
<212> TYPE: PRT
<213> ORGANISM: Artificial Sequence
<220> FEATURE:
<223> OTHER INFORMATION: Synthetic peptide K28Q

<400> SEQUENCE: 53

Ile Ile Phe Trp Val Gln Arg Gly Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 54

Ile Phe Trp Val Gln Arg Gly Arg Lys
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 55

Phe Trp Val Gln Arg Gly Arg Lys Lys
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 56

Trp Val Gln Arg Gly Arg Lys Lys Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 57

Ile Ile Phe Trp Val Lys Arg Gly Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 58

Ile Phe Trp Val Lys Arg Gly Ser Lys
1               5

<210> SEQ ID NO 59
<211> LENGTH: 9
<212> TYPE: PRT
```

```
<213> ORGANISM: Artificial Sequence
<220> FEATURE:
<223> OTHER INFORMATION: Synthetic peptide R31S

<400> SEQUENCE: 59

Phe Trp Val Lys Arg Gly Ser Lys Lys
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 60

Trp Val Lys Arg Gly Ser Lys Lys Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 61

Ile Ile Phe Trp Val Lys Arg Gly Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 62

Ile Phe Trp Val Lys Arg Gly Leu Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 63

Phe Trp Val Lys Arg Gly Leu Lys Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 64

Trp Val Lys Arg Gly Leu Lys Lys Leu
1               5

<210> SEQ ID NO 65
<211> LENGTH: 9
<212> TYPE: PRT
<213> ORGANISM: Artificial Sequence
```

```
<220> FEATURE:
<223> OTHER INFORMATION: Synthetic peptide R31H

<400> SEQUENCE: 65

Ile Ile Phe Trp Val Lys Arg Gly His
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 66

Ile Phe Trp Val Lys Arg Gly His Lys
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 67

Phe Trp Val Lys Arg Gly His Lys Lys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 68

Trp Val Lys Arg Gly His Lys Lys Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 69

Ile Ile Phe Trp Val Lys Arg Gly Ala
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 70

Ile Phe Trp Val Lys Arg Gly Ala Lys
1               5

<210> SEQ ID NO 71
<211> LENGTH: 9
<212> TYPE: PRT
<213> ORGANISM: Artificial Sequence
<220> FEATURE:
```

```
<223> OTHER INFORMATION: Synthetic peptide R31A

<400> SEQUENCE: 71

Phe Trp Val Lys Arg Gly Ala Lys Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 72

Trp Val Lys Arg Gly Ala Lys Lys Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 73

Ile Ile Phe Trp Val Lys Arg Gly Asn
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 74

Ile Phe Trp Val Lys Arg Gly Asn Lys
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 75

Phe Trp Val Lys Arg Gly Asn Lys Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 76

Trp Val Lys Arg Gly Asn Lys Lys Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide K28Q/R31S
```

```
<400> SEQUENCE: 77

Ile Ile Phe Trp Val Gln Arg Gly Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 78

Ile Phe Trp Val Gln Arg Gly Ser Lys
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 79

Phe Trp Val Gln Arg Gly Ser Lys Lys
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 80

Trp Val Gln Arg Gly Ser Lys Lys Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 81

Ile Ile Phe Trp Val Gln Arg Gly Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 82

Ile Phe Trp Val Gln Arg Gly Ala Lys
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide K28Q/R31A
```

```
<400> SEQUENCE: 83

Phe Trp Val Gln Arg Gly Ala Lys Lys
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 84

Trp Val Gln Arg Gly Ala Lys Lys Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 85

Ile Ile Phe Trp Val Gln Arg Gly Asn
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 86

Ile Phe Trp Val Gln Arg Gly Asn Lys
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 87

Phe Trp Val Gln Arg Gly Asn Lys Lys
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 88

Trp Val Gln Arg Gly Asn Lys Lys Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide L34S

<400> SEQUENCE: 89
```

```
Trp Val Lys Arg Gly Arg Lys Lys Ser
1               5
```

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide L34A

<400> SEQUENCE: 90

```
Trp Val Lys Arg Gly Arg Lys Lys Ala
1               5
```

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide K28Q/L34S

<400> SEQUENCE: 91

```
Trp Val Gln Arg Gly Asn Lys Lys Ser
1               5
```

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide K28Q/L34A

<400> SEQUENCE: 92

```
Trp Val Gln Arg Gly Asn Lys Lys Ala
1               5
```

<210> SEQ ID NO 93
<211> LENGTH: 255
<212> TYPE: PRT
<213> ORGANISM: Homo sapiens
<220> FEATURE:
<223> OTHER INFORMATION: 4-1BB

<400> SEQUENCE: 93

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140
```

```
Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 94
<211> LENGTH: 255
<212> TYPE: PRT
<213> ORGANISM: Homo sapiens
<220> FEATURE:
<223> OTHER INFORMATION: CD28

<400> SEQUENCE: 94

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 95
<211> LENGTH: 164
<212> TYPE: PRT
<213> ORGANISM: Homo sapiens
<220> FEATURE:
<223> OTHER INFORMATION: CD3 zeta chain

<400> SEQUENCE: 95

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 96
<211> LENGTH: 14
<212> TYPE: PRT
<213> ORGANISM: Artificial Sequence
<220> FEATURE:
<223> OTHER INFORMATION: Synthetic

<400> SEQUENCE: 96

Phe Ile Ile Phe Trp Val Asn Asn Lys Arg Gly Arg Lys Lys
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic

<400> SEQUENCE: 97

Ile Phe Trp Val Asn Asn Lys Arg Gly Arg Lys Lys Leu Leu
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic

<400> SEQUENCE: 98

```
Phe Ile Ile Phe Trp Val Asn Asn Lys Arg Gly Arg Lys Lys
1               5                   10
```

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

```
Ile Phe Trp Val Asn Asn Lys Arg Gly Arg Lys Lys Leu Leu
1               5                   10
```

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide K28R

<400> SEQUENCE: 100

```
Val Ala Phe Ile Ile Phe Trp Val Arg
1               5
```

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide K28R

<400> SEQUENCE: 101

```
Ala Phe Ile Ile Phe Trp Val Arg Arg
1               5
```

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 102

```
Phe Ile Ile Phe Trp Val Ala Arg Gly
1               5
```

<210> SEQ ID NO 103
<211> LENGTH: 28
<212> TYPE: PRT
<213> ORGANISM: Homo sapiens
<220> FEATURE:
<223> OTHER INFORMATION: CD28 transmembrane domain

<400> SEQUENCE: 103

```
Met Phe Trp Val Leu Val Val Val Gly Gly Val Leu Ala Cys Tyr Ser
1               5                   10                  15

Leu Leu Val Thr Val Ala Phe Ile Ile Phe Trp Val
                20                  25
```

<210> SEQ ID NO 104
<211> LENGTH: 66
<212> TYPE: PRT
<213> ORGANISM: Homo sapiens
<220> FEATURE:
<223> OTHER INFORMATION: CD28

-continued

<400> SEQUENCE: 104

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 105
<211> LENGTH: 112
<212> TYPE: PRT
<213> ORGANISM: Homo sapiens
<220> FEATURE:
<223> OTHER INFORMATION: CD3 zeta

<400> SEQUENCE: 105

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 106
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 106
gaatctaagt acggaccgcc ctgcccccct tgccct                                36

<210> SEQ ID NO 107
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 107

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

```
Ile Ala Val Glu Trp Glu Ser Asn Gly Gln Pro Glu Asn Asn Tyr Lys
 50                  55                  60

Thr Thr Pro Pro Val Leu Asp Ser Asp Gly Ser Phe Phe Leu Tyr Ser
 65                  70                  75                  80

Arg Leu Thr Val Asp Lys Ser Arg Trp Gln Glu Gly Asn Val Phe Ser
                 85                  90                  95

Cys Ser Val Met His Glu Ala Leu His Asn His Tyr Thr Gln Lys Ser
                100                 105                 110

Leu Ser Leu Ser Leu Gly Lys
            115

<210> SEQ ID NO 108
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 108

Glu Ser Lys Tyr Gly Pro Pro Cys Pro Pro Cys Pro Ala Pro Glu Phe
 1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225

<210> SEQ ID NO 109
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 109
```

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 110
<211> LENGTH: 24
<212> TYPE: PRT
<213> ORGANISM: Artificial Sequence
<220> FEATURE:
<223> OTHER INFORMATION: Synthetic
<220> FEATURE:
<223> OTHER INFORMATION: T2A

<400> SEQUENCE: 110

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 111
<211> LENGTH: 357
<212> TYPE: PRT
<213> ORGANISM: Artificial Sequence
<220> FEATURE:

<223> OTHER INFORMATION: Synthetic
<220> FEATURE:
<223> OTHER INFORMATION: tEGFR

<400> SEQUENCE: 111

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
            355
```

<210> SEQ ID NO 112
<211> LENGTH: 41
<212> TYPE: PRT

<213> ORGANISM: Homo sapiens
<220> FEATURE:
<223> OTHER INFORMATION: CD28 cytoplasmic domain

<400> SEQUENCE: 112

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 113
<211> LENGTH: 41
<212> TYPE: PRT
<213> ORGANISM: Homo sapiens
<220> FEATURE:
<223> OTHER INFORMATION: CD28 cytoplasmic domain

<400> SEQUENCE: 113

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 114
<211> LENGTH: 69
<212> TYPE: PRT
<213> ORGANISM: Artificial Sequence
<220> FEATURE:
<223> OTHER INFORMATION: Synthetic K28A

<400> SEQUENCE: 114

Phe Trp Val Leu Val Val Val Gly Gly Val Leu Ala Cys Tyr Ser Leu
1               5                   10                  15

Leu Val Thr Val Ala Phe Ile Ile Phe Trp Val Ala Arg Gly Arg Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 115
<211> LENGTH: 69
<212> TYPE: PRT
<213> ORGANISM: Artificial Sequence
<220> FEATURE:
<223> OTHER INFORMATION: Synthetic K28H

<400> SEQUENCE: 115

Phe Trp Val Leu Val Val Val Gly Gly Val Leu Ala Cys Tyr Ser Leu
1               5                   10                  15

Leu Val Thr Val Ala Phe Ile Ile Phe Trp Val His Arg Gly Arg Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu

-continued

```
            50                  55                  60

Gly Gly Cys Glu Leu
 65

<210> SEQ ID NO 116
<211> LENGTH: 69
<212> TYPE: PRT
<213> ORGANISM: Artificial Sequence
<220> FEATURE:
<223> OTHER INFORMATION: Synthetic K28L

<400> SEQUENCE: 116

Phe Trp Val Leu Val Val Gly Gly Val Leu Ala Cys Tyr Ser Leu
  1               5                  10                  15

Leu Val Thr Val Ala Phe Ile Ile Phe Trp Val Leu Arg Gly Arg Lys
                 20                  25                  30

Lys Leu Leu Tyr Ile Phe Lys Gln Pro Phe Met Arg Pro Val Gln Thr
                 35                  40                  45

Thr Gln Glu Glu Asp Gly Cys Ser Cys Arg Phe Pro Glu Glu Glu Glu
             50                  55                  60

Gly Gly Cys Glu Leu
 65

<210> SEQ ID NO 117
<211> LENGTH: 69
<212> TYPE: PRT
<213> ORGANISM: Artificial Sequence
<220> FEATURE:
<223> OTHER INFORMATION: Synthetic K28Q

<400> SEQUENCE: 117

Phe Trp Val Leu Val Val Gly Gly Val Leu Ala Cys Tyr Ser Leu
  1               5                  10                  15

Leu Val Thr Val Ala Phe Ile Ile Phe Trp Val Gln Arg Gly Arg Lys
                 20                  25                  30

Lys Leu Leu Tyr Ile Phe Lys Gln Pro Phe Met Arg Pro Val Gln Thr
                 35                  40                  45

Thr Gln Glu Glu Asp Gly Cys Ser Cys Arg Phe Pro Glu Glu Glu Glu
             50                  55                  60

Gly Gly Cys Glu Leu
 65

<210> SEQ ID NO 118
<211> LENGTH: 69
<212> TYPE: PRT
<213> ORGANISM: Artificial Sequence
<220> FEATURE:
<223> OTHER INFORMATION: Synthetic K28S

<400> SEQUENCE: 118

Phe Trp Val Leu Val Val Gly Gly Val Leu Ala Cys Tyr Ser Leu
  1               5                  10                  15

Leu Val Thr Val Ala Phe Ile Ile Phe Trp Val Ser Arg Gly Arg Lys
                 20                  25                  30

Lys Leu Leu Tyr Ile Phe Lys Gln Pro Phe Met Arg Pro Val Gln Thr
                 35                  40                  45

Thr Gln Glu Glu Asp Gly Cys Ser Cys Arg Phe Pro Glu Glu Glu Glu
             50                  55                  60

Gly Gly Cys Glu Leu
 65
```

```
<210> SEQ ID NO 119
<211> LENGTH: 69
<212> TYPE: PRT
<213> ORGANISM: Artificial Sequence
<220> FEATURE:
<223> OTHER INFORMATION: Synthetic R31A

<400> SEQUENCE: 119
```

Phe Trp Val Leu Val Val Val Gly Gly Val Leu Ala Cys Tyr Ser Leu
1               5                   10                  15

Leu Val Thr Val Ala Phe Ile Ile Phe Trp Val Lys Arg Gly Ala Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

```
<210> SEQ ID NO 120
<211> LENGTH: 69
<212> TYPE: PRT
<213> ORGANISM: Artificial Sequence
<220> FEATURE:
<223> OTHER INFORMATION: Synthetic R31H

<400> SEQUENCE: 120
```

Phe Trp Val Leu Val Val Val Gly Gly Val Leu Ala Cys Tyr Ser Leu
1               5                   10                  15

Leu Val Thr Val Ala Phe Ile Ile Phe Trp Val Lys Arg Gly His Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

```
<210> SEQ ID NO 121
<211> LENGTH: 69
<212> TYPE: PRT
<213> ORGANISM: Artificial Sequence
<220> FEATURE:
<223> OTHER INFORMATION: Synthetic R31L

<400> SEQUENCE: 121
```

Phe Trp Val Leu Val Val Val Gly Gly Val Leu Ala Cys Tyr Ser Leu
1               5                   10                  15

Leu Val Thr Val Ala Phe Ile Ile Phe Trp Val Lys Arg Gly Leu Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

```
<210> SEQ ID NO 122
<211> LENGTH: 69
```

```
<212> TYPE: PRT
<213> ORGANISM: Artificial Sequence
<220> FEATURE:
<223> OTHER INFORMATION: Synthetic R31N

<400> SEQUENCE: 122

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 123
<211> LENGTH: 69
<212> TYPE: PRT
<213> ORGANISM: Artificial Sequence
<220> FEATURE:
<223> OTHER INFORMATION: Synthetic L34A

<400> SEQUENCE: 123

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Ala Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 124
<211> LENGTH: 69
<212> TYPE: PRT
<213> ORGANISM: Artificial Sequence
<220> FEATURE:
<223> OTHER INFORMATION: Synthetic L34S

<400> SEQUENCE: 124

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Ser Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 125
<211> LENGTH: 69
<212> TYPE: PRT
<213> ORGANISM: Artificial Sequence
<220> FEATURE:
<223> OTHER INFORMATION: Synthetic K28Q/R31A
```

```
<400> SEQUENCE: 125

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Ala Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 126
<211> LENGTH: 69
<212> TYPE: PRT
<213> ORGANISM: Artificial Sequence
<220> FEATURE:
<223> OTHER INFORMATION: Synthetic K28Q/R31N

<400> SEQUENCE: 126

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 127
<211> LENGTH: 69
<212> TYPE: PRT
<213> ORGANISM: Artificial Sequence
<220> FEATURE:
<223> OTHER INFORMATION: Synthetic K28Q/R31S

<400> SEQUENCE: 127

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Ser Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 128
<211> LENGTH: 69
<212> TYPE: PRT
<213> ORGANISM: Artificial Sequence
<220> FEATURE:
<223> OTHER INFORMATION: Synthetic K28Q/L34A

<400> SEQUENCE: 128

Phe Trp Val Leu Val Val Val Gly Gly Val Leu Ala Cys Tyr Ser Leu
```

```
                1               5                   10                  15
Leu Val Thr Val Ala Phe Ile Ile Phe Trp Val Gln Arg Gly Arg Lys
                20                  25                  30

Lys Ala Leu Tyr Ile Phe Lys Gln Pro Phe Met Arg Pro Val Gln Thr
                35                  40                  45

Thr Gln Glu Glu Asp Gly Cys Ser Cys Arg Phe Pro Glu Glu Glu Glu
                50                  55                  60

Gly Gly Cys Glu Leu
65

<210> SEQ ID NO 129
<211> LENGTH: 69
<212> TYPE: PRT
<213> ORGANISM: Artificial Sequence
<220> FEATURE:
<223> OTHER INFORMATION: Synthetic K28Q/L34S

<400> SEQUENCE: 129

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Arg Lys
                20                  25                  30

Lys Ser Leu Tyr Ile Phe Lys Gln Pro Phe Met Arg Pro Val Gln Thr
                35                  40                  45

Thr Gln Glu Glu Asp Gly Cys Ser Cys Arg Phe Pro Glu Glu Glu Glu
                50                  55                  60

Gly Gly Cys Glu Leu
65

<210> SEQ ID NO 130
<211> LENGTH: 69
<212> TYPE: PRT
<213> ORGANISM: Artificial Sequence
<220> FEATURE:
<223> OTHER INFORMATION: Synthetic R31N/L34A

<400> SEQUENCE: 130

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
                20                  25                  30

Lys Ala Leu Tyr Ile Phe Lys Gln Pro Phe Met Arg Pro Val Gln Thr
                35                  40                  45

Thr Gln Glu Glu Asp Gly Cys Ser Cys Arg Phe Pro Glu Glu Glu Glu
                50                  55                  60

Gly Gly Cys Glu Leu
65

<210> SEQ ID NO 131
<211> LENGTH: 69
<212> TYPE: PRT
<213> ORGANISM: Artificial Sequence
<220> FEATURE:
<223> OTHER INFORMATION: Synthetic R31N/L34S

<400> SEQUENCE: 131

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
                20                  25                  30
```

```
Lys Ser Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65
```

<210> SEQ ID NO 132
<211> LENGTH: 69
<212> TYPE: PRT
<213> ORGANISM: Artificial Sequence
<220> FEATURE:
<223> OTHER INFORMATION: Synthetic K28Q/R31N/L34A

<400> SEQUENCE: 132

```
Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
        20                  25                  30

Lys Ala Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65
```

<210> SEQ ID NO 133
<211> LENGTH: 69
<212> TYPE: PRT
<213> ORGANISM: Artificial Sequence
<220> FEATURE:
<223> OTHER INFORMATION: Synthetic K28Q/R31N/L34S

<400> SEQUENCE: 133

```
Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
        20                  25                  30

Lys Ser Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65
```

<210> SEQ ID NO 134
<211> LENGTH: 71
<212> TYPE: PRT
<213> ORGANISM: Artificial Sequence
<220> FEATURE:
<223> OTHER INFORMATION: Synthetic
<220> FEATURE:
<223> OTHER INFORMATION: NN Insertion

<400> SEQUENCE: 134

```
Phe Trp Val Leu Val Val Gly Gly Val Leu Ala Cys Tyr Ser Leu
1               5                   10                  15

Leu Val Thr Val Ala Phe Ile Ile Phe Trp Val Asn Asn Lys Arg Gly
        20                  25                  30

Arg Lys Lys Leu Leu Tyr Ile Phe Lys Gln Pro Phe Met Arg Pro Val
```

```
            35                  40                  45
Gln Thr Thr Gln Glu Glu Asp Gly Cys Ser Cys Arg Phe Pro Glu Glu
    50                  55                  60

Glu Glu Gly Gly Cys Glu Leu
65                  70

<210> SEQ ID NO 135
<211> LENGTH: 70
<212> TYPE: PRT
<213> ORGANISM: Artificial Sequence
<220> FEATURE:
<223> OTHER INFORMATION: Synthetic

<400> SEQUENCE: 135

Met Phe Trp Val Leu Val Val Gly Gly Val Leu Ala Cys Tyr Ser
1               5                   10                  15

Leu Leu Val Thr Val Ala Phe Ile Ile Phe Trp Val Lys Arg Gly Arg
            20                  25                  30

Lys Lys Leu Leu Tyr Ile Phe Lys Gln Pro Phe Met Arg Pro Val Gln
        35                  40                  45

Thr Thr Gln Glu Glu Asp Gly Cys Ser Cys Arg Phe Pro Glu Glu Glu
    50                  55                  60

Glu Gly Gly Cys Glu Leu
65                  70

<210> SEQ ID NO 136
<211> LENGTH: 108
<212> TYPE: PRT
<213> ORGANISM: Artificial Sequence
<220> FEATURE:
<223> OTHER INFORMATION: Synthetic

<400> SEQUENCE: 136

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Gly Gly
        35                  40                  45

Val Leu Ala Cys Tyr Ser Leu Leu Val Thr Val Ala Phe Ile Ile Phe
    50                  55                  60

Trp Val Lys Arg Gly Arg Lys Lys Leu Leu Tyr Ile Phe Lys Gln Pro
65                  70                  75                  80

Phe Met Arg Pro Val Gln Thr Thr Gln Glu Glu Asp Gly Cys Ser Cys
                85                  90                  95

Arg Phe Pro Glu Glu Glu Glu Gly Gly Cys Glu Leu
                100                 105

<210> SEQ ID NO 137
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region

<400> SEQUENCE: 137

Ser Leu Leu Val Thr Val Ala Phe Ile Ile Phe Trp Val Lys Arg Gly
1               5                   10                  15
```

Arg Lys Lys Leu Leu Tyr Ile Phe Lys Gln
            20                  25

<210> SEQ ID NO 138
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14A

<400> SEQUENCE: 138

Ser Leu Leu Val Thr Val Ala Phe Ile Ile Phe Trp Val Ala Arg Gly
1               5                   10                  15

Arg Lys Lys Leu Leu Tyr Ile Phe Lys Gln
            20                  25

<210> SEQ ID NO 139
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14H

<400> SEQUENCE: 139

Ser Leu Leu Val Thr Val Ala Phe Ile Ile Phe Trp Val His Arg Gly
1               5                   10                  15

Arg Lys Lys Leu Leu Tyr Ile Phe Lys Gln
            20                  25

<210> SEQ ID NO 140
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14L

<400> SEQUENCE: 140

Ser Leu Leu Val Thr Val Ala Phe Ile Ile Phe Trp Val Leu Arg Gly
1               5                   10                  15

Arg Lys Lys Leu Leu Tyr Ile Phe Lys Gln
            20                  25

<210> SEQ ID NO 141
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q

<400> SEQUENCE: 141

Ser Leu Leu Val Thr Val Ala Phe Ile Ile Phe Trp Val Gln Arg Gly
1               5                   10                  15

Arg Lys Lys Leu Leu Tyr Ile Phe Lys Gln
            20                  25

<210> SEQ ID NO 142
<211> LENGTH: 26
<212> TYPE: PRT

```
<213> ORGANISM: Artificial Sequence
<220> FEATURE:
<223> OTHER INFORMATION: Synthetic
<220> FEATURE:
<223> OTHER INFORMATION: junction region K14S

<400> SEQUENCE: 142

Ser Leu Leu Val Thr Val Ala Phe Ile Ile Phe Trp Val Ser Arg Gly
1               5                   10                  15
Arg Lys Lys Leu Leu Tyr Ile Phe Lys Gln
            20                  25

<210> SEQ ID NO 143
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17A

<400> SEQUENCE: 143

Ser Leu Leu Val Thr Val Ala Phe Ile Ile Phe Trp Val Lys Arg Gly
1               5                   10                  15
Ala Lys Lys Leu Leu Tyr Ile Phe Lys Gln
            20                  25

<210> SEQ ID NO 144
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17H

<400> SEQUENCE: 144

Ser Leu Leu Val Thr Val Ala Phe Ile Ile Phe Trp Val Lys Arg Gly
1               5                   10                  15
His Lys Lys Leu Leu Tyr Ile Phe Lys Gln
            20                  25

<210> SEQ ID NO 145
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17L

<400> SEQUENCE: 145

Ser Leu Leu Val Thr Val Ala Phe Ile Ile Phe Trp Val Lys Arg Gly
1               5                   10                  15
Leu Lys Lys Leu Leu Tyr Ile Phe Lys Gln
            20                  25

<210> SEQ ID NO 146
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17N

<400> SEQUENCE: 146
```

```
Ser Leu Leu Val Thr Val Ala Phe Ile Ile Phe Trp Val Lys Arg Gly
1               5                   10                  15

Asn Lys Lys Leu Leu Tyr Ile Phe Lys Gln
            20                  25

<210> SEQ ID NO 147
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region L20A

<400> SEQUENCE: 147

Ser Leu Leu Val Thr Val Ala Phe Ile Ile Phe Trp Val Lys Arg Gly
1               5                   10                  15

Arg Lys Lys Ala Leu Tyr Ile Phe Lys Gln
            20                  25

<210> SEQ ID NO 148
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region L20S

<400> SEQUENCE: 148

Ser Leu Leu Val Thr Val Ala Phe Ile Ile Phe Trp Val Lys Arg Gly
1               5                   10                  15

Arg Lys Lys Ser Leu Tyr Ile Phe Lys Gln
            20                  25

<210> SEQ ID NO 149
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17A

<400> SEQUENCE: 149

Ser Leu Leu Val Thr Val Ala Phe Ile Ile Phe Trp Val Gln Arg Gly
1               5                   10                  15

Ala Lys Lys Leu Leu Tyr Ile Phe Lys Gln
            20                  25

<210> SEQ ID NO 150
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17N

<400> SEQUENCE: 150

Ser Leu Leu Val Thr Val Ala Phe Ile Ile Phe Trp Val Gln Arg Gly
1               5                   10                  15

Asn Lys Lys Leu Leu Tyr Ile Phe Lys Gln
            20                  25
```

<210> SEQ ID NO 151
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17S

<400> SEQUENCE: 151

Ser Leu Leu Val Thr Val Ala Phe Ile Ile Phe Trp Val Gln Arg Gly
1               5                   10                  15

Ser Lys Lys Leu Leu Tyr Ile Phe Lys Gln
            20                  25

<210> SEQ ID NO 152
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/L20A

<400> SEQUENCE: 152

Ser Leu Leu Val Thr Val Ala Phe Ile Ile Phe Trp Val Gln Arg Gly
1               5                   10                  15

Arg Lys Lys Ala Leu Tyr Ile Phe Lys Gln
            20                  25

<210> SEQ ID NO 153
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/L20S

<400> SEQUENCE: 153

Ser Leu Leu Val Thr Val Ala Phe Ile Ile Phe Trp Val Gln Arg Gly
1               5                   10                  15

Arg Lys Lys Ser Leu Tyr Ile Phe Lys Gln
            20                  25

<210> SEQ ID NO 154
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17N/L20A

<400> SEQUENCE: 154

Ser Leu Leu Val Thr Val Ala Phe Ile Ile Phe Trp Val Lys Arg Gly
1               5                   10                  15

Asn Lys Lys Ala Leu Tyr Ile Phe Lys Gln
            20                  25

<210> SEQ ID NO 155
<211> LENGTH: 26
<212> TYPE: PRT
<213> ORGANISM: Artificial Sequence
<220> FEATURE:
<223> OTHER INFORMATION: Synthetic

```
<220> FEATURE:
<223> OTHER INFORMATION: junction region R17N/L20S

<400> SEQUENCE: 155

Ser Leu Leu Val Thr Val Ala Phe Ile Ile Phe Trp Val Lys Arg Gly
1               5                   10                  15

Asn Lys Lys Ser Leu Tyr Ile Phe Lys Gln
            20                  25

<210> SEQ ID NO 156
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17N/L20A

<400> SEQUENCE: 156

Ser Leu Leu Val Thr Val Ala Phe Ile Ile Phe Trp Val Gln Arg Gly
1               5                   10                  15

Asn Lys Lys Ala Leu Tyr Ile Phe Lys Gln
            20                  25

<210> SEQ ID NO 157
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17N/L20S

<400> SEQUENCE: 157

Ser Leu Leu Val Thr Val Ala Phe Ile Ile Phe Trp Val Gln Arg Gly
1               5                   10                  15

Asn Lys Lys Ser Leu Tyr Ile Phe Lys Gln
            20                  25

<210> SEQ ID NO 158
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 158
gaatctaagt acggaccgcc ctgcccccct tgccct                              36

<210> SEQ ID NO 159
<211> LENGTH: 112
<212> TYPE: PRT
<213> ORGANISM: Artificial Sequence
<220> FEATURE:
<223> OTHER INFORMATION: Synthetic
<220> FEATURE:
<223> OTHER INFORMATION: CD3 Zeta

<400> SEQUENCE: 159

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 160
<211> LENGTH: 36
<212> TYPE: PRT
<213> ORGANISM: Artificial Sequence
<220> FEATURE:
<223> OTHER INFORMATION: Synthetic

<400> SEQUENCE: 160

Cys Tyr Ser Leu Leu Val Thr Val Ala Phe Ile Ile Phe Trp Val Lys
1               5                   10                  15

Arg Gly Arg Lys Lys Leu Leu Tyr Ile Phe Lys Gln Pro Phe Met Arg
                20                  25                  30

Pro Val Gln Thr
        35

<210> SEQ ID NO 161
<211> LENGTH: 15
<212> TYPE: PRT
<213> ORGANISM: Artificial Sequence
<220> FEATURE:
<223> OTHER INFORMATION: Synthetic

<400> SEQUENCE: 161

Cys Tyr Ser Leu Leu Val Thr Val Ala Phe Ile Ile Phe Trp Val
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic

<400> SEQUENCE: 162

Leu Leu Val Thr Val Ala Phe Ile Ile Phe Trp Val Lys Arg Gly
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Synthetic

<400> SEQUENCE: 163

Thr Val Ala Phe Ile Ile Phe Trp Val Lys Arg Gly Arg Lys Lys
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetic

```
<400> SEQUENCE: 164

Phe Ile Ile Phe Trp Val Lys Arg Gly Arg Lys Lys Leu Leu Tyr
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic

<400> SEQUENCE: 165

Phe Trp Val Lys Arg Gly Arg Lys Lys Leu Leu Tyr Ile Phe Lys
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Synthetic

<400> SEQUENCE: 166

Lys Arg Gly Arg Lys Lys Leu Leu Tyr Ile Phe Lys Gln Pro Phe
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic

<400> SEQUENCE: 167

Arg Lys Lys Leu Leu Tyr Ile Phe Lys Gln Pro Phe Met Arg Pro
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Leu Leu Tyr Ile Phe Lys Gln Pro Phe Met Arg Pro Val Gln Thr
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic peptide R31H

<400> SEQUENCE: 169

Thr Val Ala Phe Ile Ile Phe Trp Val Lys Arg Gly His Lys Lys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic peptide R31H

<400> SEQUENCE: 170
```

Phe Ile Ile Phe Trp Val Lys Arg Gly His Lys Lys Leu Leu Tyr
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic peptide R31H

<400> SEQUENCE: 171

Phe Trp Val Lys Arg Gly His Lys Lys Leu Leu Tyr Ile Phe Lys
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Synthetic peptide R31H

<400> SEQUENCE: 172

Lys Arg Gly His Lys Lys Leu Leu Tyr Ile Phe Lys Gln Pro Phe
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Synthetic peptide R31H

<400> SEQUENCE: 173

His Lys Lys Leu Leu Tyr Ile Phe Lys Gln Pro Phe Met Arg Pro
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Synthetic peptide R31N

<400> SEQUENCE: 174

Thr Val Ala Phe Ile Ile Phe Trp Val Lys Arg Gly Asn Lys Lys
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Synthetic peptide R31N

<400> SEQUENCE: 175

Phe Ile Ile Phe Trp Val Lys Arg Gly Asn Lys Lys Leu Leu Tyr
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Synthetic peptide R31N

<400> SEQUENCE: 176

-continued

Phe Trp Val Lys Arg Gly Asn Lys Lys Leu Leu Tyr Ile Phe Lys
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Synthetic peptide R31N

<400> SEQUENCE: 177

Lys Arg Gly Asn Lys Lys Leu Leu Tyr Ile Phe Lys Gln Pro Phe
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Synthetic peptide R31N

<400> SEQUENCE: 178

Asn Lys Lys Leu Leu Tyr Ile Phe Lys Gln Pro Phe Met Arg Pro
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic peptide L34A

<400> SEQUENCE: 179

Phe Ile Ile Phe Trp Val Lys Arg Gly Arg Lys Lys Ala Leu Tyr
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthetic peptide L34A

<400> SEQUENCE: 180

Phe Trp Val Lys Arg Gly Arg Lys Lys Ala Leu Tyr Ile Phe Lys
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Synthetic peptide L34A

<400> SEQUENCE: 181

Lys Arg Gly Arg Lys Lys Ala Leu Tyr Ile Phe Lys Gln Pro Phe
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic peptide L34A

<400> SEQUENCE: 182

Arg Lys Lys Ala Leu Tyr Ile Phe Lys Gln Pro Phe Met Arg Pro

```
<210> SEQ ID NO 183
<211> LENGTH: 69
<212> TYPE: PRT
<213> ORGANISM: Artificial Sequence
<220> FEATURE:
<223> OTHER INFORMATION: Synthetic R31S

<400> SEQUENCE: 183

Phe Trp Val Leu Val Val Val Gly Gly Val Leu Ala Cys Tyr Ser Leu
1               5                   10                  15

Leu Val Thr Val Ala Phe Ile Ile Phe Trp Val Lys Arg Gly Ser Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 184
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R31S

<400> SEQUENCE: 184

Ser Leu Leu Val Thr Val Ala Phe Ile Ile Phe Trp Val Lys Arg Gly
1               5                   10                  15

Ser Lys Lys Leu Leu Tyr Ile Phe Lys Gln
            20                  25
```

MODIFIED CHIMERIC RECEPTORS AND RELATED COMPOSITIONS AND METHODS

CROSS-REFERENCE TO RELATED APPLICATIONS

This application is a U.S. National Stage of International Application No. PCT/US2016/064861 filed Dec. 2, 2016, which claims priority from U.S. provisional application No. 62/348,130 filed Jun. 9, 2016, entitled "Modified Chimeric Receptors and Related Compositions and Methods," and U.S. provisional application No. 62/262,911 filed Dec. 3, 2015, entitled "Modified Chimeric Receptors and Related Compositions and Methods," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042004700SeqList.txt, created May 30, 2018, which is 71,935 bytes in size. The information in electronic format of the Sequence Listing is incorporated by reference in its entirety.

FIELD

The present disclosure relates in some aspects to chimeric receptors for engineering cells for adoptive therapy, including T cells, and the genetically engineered cells. In some embodiments, the chimeric receptors, such as chimeric antigen receptors (CARs) are modified in a junction region by one or more amino acid modifications such that peptide fragments of such region exhibit a lower binding affinity for a human leukocyte antigen (HLA) and/or the region exhibits reduced immunogenicity, including following administration to a subject. In some aspects, the disclosure further relates to methods and compositions for engineering and producing cells expressing such chimeric receptors, compositions containing the cells, and method for their administration to subjects. In some embodiments, features of the chimeric receptors and engineered cells containing the chimeric receptors result in methods that provide for increased or improved activity, efficacy and/or persistence.

BACKGROUND

Various methods are available for adoptive cell therapy using engineered cells expressing recombinant receptors, such as chimeric antigen receptor (CARs). Such methods may benefit from enhanced expansion and/or persistence of the administered cells, reduction of the immune response to the receptors expressed on the cells or other unwanted outcomes. Provided are products, compositions, methods and articles of manufacture that meet such needs.

SUMMARY

Provided herein is a variant chimeric receptor that is modified compared to a reference chimeric receptor by one or more amino acid sequence modifications in a junction region, said junction region being a region containing a contiguous sequence of amino acids on each side of a junction between two domains, i.e. region spanning two domains. In some embodiments, provided herein is a variant chimeric receptor including a modified junction region having one or more amino acid sequence modifications compared to a junction region of the reference chimeric receptor, wherein the reference chimeric receptor includes a first domain and a second domain, joined in contiguous sequence at a junction, wherein the junction region of the reference chimeric receptor includes up to 15 contiguous amino acids directly C-terminal of the junction and/or up to 15 contiguous amino acids directly N-terminal of the junction; and a peptide fragment having the sequence of an 8-15 amino acid portion of the modified junction region has a binding affinity for a human leukocyte antigen (HLA) molecule that is lower than the binding affinity, for the same HLA molecule, of a peptide fragment having the sequence of the corresponding portion of the junction region of the reference chimeric receptor. In some embodiments, the peptide fragment of the corresponding portion of the junction region of the reference chimeric receptor has a binding affinity of less than 1000 nM, less than 500 nM or less than 50 nM.

In some embodiments, provided herein is a variant chimeric receptor including a modified junction region having one or more amino acid sequence modifications compared to a junction region of a reference chimeric receptor, wherein the reference chimeric receptor includes a first domain and a second domain, joined in contiguous sequence at a junction, wherein the junction region of the reference chimeric receptor includes up to 15 contiguous amino acids directly C-terminal of the junction and/or up to 15 contiguous amino acids directly N-terminal of the junction; and the average of the binding affinities of all 8-15 amino acid fragments, or of all 8, 9, 10, 11, 12, 13, 14, or 15 amino acid fragments, within the modified junction region for a human HLA molecule is lower than the average of the binding affinities of all 8-15 amino acid fragments, or of all 8, 9, 10, 11, 12, 13, 14, or 15 amino acid fragments, within the junction region of the reference chimeric receptor.

In some embodiments, the binding affinity or average of binding affinities is more than 2-fold, more than 5-fold, more than 10-fold, more than 25-fold, more than 50-fold or more than 100-fold lower.

In some embodiments, provided herein is a variant chimeric receptor including a modified junction region having one or more amino acid sequence modifications compared to a junction region of a reference chimeric receptor, wherein the reference chimeric receptor includes a first domain directly linked to a second domain joined in contiguous sequence at a junction, wherein the junction region of the reference chimeric receptor includes up to 15 contiguous amino acids directly C-terminal of the junction and/or up to 15 contiguous amino acids directly N-terminal of the junction; and the number of peptide fragments having the sequence of an 8-15 amino acid portion of the modified junction region that has a binding affinity for a human leukocyte antigen (HLA) of less than 1000 nM is reduced compared to the number of peptide fragments having the sequence of an 8-15 amino acid portion of the junction region of the reference chimeric receptor that has the same affinity for binding the same HLA.

In some embodiments, the number of peptide fragments within the modified junction region that exhibits a binding affinity for an HLA of less than 500 nM or less than 50 nM is reduced; or the binding affinity of less than 1000 nM is a binding affinity of less than 500 nM or less than 50 nm. In some embodiments, the binding affinity is an IC50 and the comparison of binding of peptide fragments of the modified junction regions and the peptide fragments of the junction region of the reference chimeric receptor is with reference to the same standard peptide.

In some embodiments, the first domain and/or second domain of the reference chimeric receptor includes a domain of a natural human protein; and/or the first domain and/or second domain includes an extracellular binding domain, a hinge domain, a transmembrane domain, or an intracellular signaling domain, which intracellular signaling domain is, optionally, a costimulatory signaling domain or an activating cytoplasmic signaling domain. In some embodiments, the first domain and second domain of the reference chimeric receptor are not present in the same molecule in vivo in a human subject.

In some embodiments, the first domain and second domain of the reference chimeric receptor are, respectively, an extracellular ligand binding domain and a hinge domain, a hinge domain and a transmembrane domain, a transmembrane domain and an intracellular costimulatory signaling domain, and an intracellular costimulatory signaling domain and an activating cytoplasmic signaling domain, which can include functional portions of such domains. In some embodiments, the first domain is a transmembrane domain or a functional portion thereof and the second domain is a costimulatory signaling domain or a functional portion thereof.

In some embodiments, the transmembrane domain is a CD28 transmembrane domain or a functional portion or variant thereof and the costimulatory signaling domain is a 4-1BB signaling domain or a functional portion or variant thereof.

In some embodiments, the junction region of the reference chimeric receptor includes up to 13 contiguous amino acids directly C-terminal of the junction and/or up to 15 contiguous amino acids directly N-terminal of the junction. In some embodiments, the peptide fragment(s) includes a sequence of amino acids between or between about 8 and 15 amino acids in length, or includes a sequence of amino acids that is at least or at least about or is or is about 8, 9, 10, 11, 12, 13, 14 or 15 amino acids in length.

In some embodiments, the variant chimeric receptor includes a domain of at least 95% sequence identity to the first domain and/or a domain of at least 95% sequence identity to the second domain, a domain identical in sequence to the first domain and a domain of at least 95% sequence identity to the second domain, or a domain of at least 95% sequence identity to the first domain and a domain identical in sequence to the second domain, wherein at least one or both of the domains present in the variant chimeric receptor is modified compared to the first domain and/or second domain of the reference chimeric receptor in the portion including the modified junction region.

In some embodiments, the variant chimeric receptor includes at least 85%, 86%, 87%, 88%, 89%, 90%, 91%, 92%, 93%, 94%, 95%, 96%, 97%, 98%, 99% or more sequence identity to the reference chimeric receptor; and/or the variant chimeric receptor includes up to 1, 2, 3, 4, 5, 6, 7, 8, 9, 10, 11, 12, 13, 14, 15, 16, 17, 18, 19 or 20 amino acid modifications compared to the reference chimeric receptor.

In some embodiments, the CD28 transmembrane domain includes the sequence of amino acids set forth in SEQ ID NO:2, 103 or 104 or a functional portion or variant thereof including a sequence that exhibits at least 95% sequence identity to SEQ ID NO:2, 103 or 104; and the 4-1BB costimulatory signaling domain includes the sequence of amino acids set forth in SEQ ID NO:3 or a functional portion or variant thereof including a sequence that exhibits at least 95% sequence identity to SEQ ID NO:3.

In some embodiments, the first domain and second domain together include the sequence of amino acids set forth in SEQ ID NO:5 or a functional portion or variant thereof including a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:5. In some embodiments, the first domain and second domain together include the sequence of amino acids set forth in SEQ ID NO:5. In some embodiments, the one or more modifications are within a portion between residue 13 and 42 or between amino acid residue 15 and 40, with reference to numbering set forth in SEQ ID NO:5. In some embodiments, the one or more modifications include an amino acid insertion, replacement or deletion and/or wherein each of the one or more modifications individually includes an amino acid insertion, replacement, or deletion.

In some embodiments, the first and/or second domain of the reference chimeric receptor includes a transmembrane domain, wherein the one or more modifications of the variant chimeric receptor is not or does not include a modification at or of a hydrophobic amino acid residue or within a hydrophobic portion in the transmembrane domain, which optionally is the CD28 transmembrane domain; or the one or more modifications include a modification of a hydrophobic amino acid residue within the transmembrane domain, which optionally is the CD28 transmembrane domain, wherein the modification is or includes a substitution of the hydrophobic amino acid with another different hydrophobic amino acid residue; or the one or more modifications is not or does not include a modification at or of a hydrophobic amino acid residue or within a hydrophobic portion in the transmembrane domain, which optionally is the CD28 transmembrane domain, other than a substitution with another hydrophobic amino acid residue.

In some embodiments, the one or more modifications include a modification at an amino acid residue corresponding to an amino acid residue between residues 28 and 42 with reference to numbering set forth in SEQ ID NO:5. In some embodiments, the amino acid modification is an insertion and the variant chimeric receptor includes an insertion between amino acid residues adjacent to the junction between the domains, which optionally corresponds to amino acid residues 27 and 28 with reference to numbering set forth SEQ ID NO:5. In some embodiments, the variant chimeric receptor includes insertion of 1, 2, 3, 4 or 5 amino acid residues. In some embodiments, the insertion is of any amino acid residue, which, optionally, is asparagine (N).

In some embodiments, the one or more modifications include an amino acid replacement(s) and the amino acid replacement(s) are at one or more residues selected from amino acid residue 28, 31 or 34 with reference to numbering set forth in SEQ ID NO:5. In some embodiments, the amino acid replacement(s) is to any other amino acid residue, which, optionally, is selected from among leucine (L), asparagine (N), glutamine (Q), alanine (A), serine(S) or histidine (H). In some embodiments, the amino acid replacement(s) is selected from among K28A, K28H, K28L, K28Q, K28S, R31A, R31H, R31L, R31N, R31S, L34A and L34S, with reference to numbering set forth in SEQ ID NO:5. In some embodiments, the amino acid replacement does not include the single amino acid replacement corresponding to L34A or L34S, with reference to numbering set forth in SEQ ID NO:5. In some embodiments, the amino acid replacements are selected from among K28Q/R31A, K28Q/R31N, K28Q/R31S, K28Q/L34A, K28Q/L34S, R31N/L34A, R31N/L34S, K28Q/R31N/L34A, K28Q/R31N/L34S.

In some embodiments, the variant chimeric receptor includes a modified junction region including less than 100% sequence identity to SEQ ID NO: 137 but greater than 85%, 86%, 87%, 88%, 89%, 90%, 91%, 92%, 93%, 94%, 95% or 96% to SEQ ID NO: 137 and includes the modification(s), such as any described herein; and/or the variant chimeric receptor includes a sequence including less than 100% sequence identity to SEQ ID NO:5 but greater than 85%, 86%, 87%, 88%, 89%, 90%, 91%, 92%, 93%, 94%, 95% or 96% to SEQ ID NO:5 and includes the modification(s), such as any described herein.

In some embodiments, the variant chimeric receptor includes a modified junction region selected from among: i) the sequence of amino acids set forth in any of SEQ ID NOS: 138-157 and 184; ii) a functional variant thereof including a sequence of amino acids that exhibits at least 95%, 96%, 97%, 98% or 99% sequence identity to the sequence of amino acids set forth in any of SEQ ID NOS: 138-157 and 184 and that include the modification(s); or iii) a functional portion of i) or ii) and includes the modification(s).

In some embodiments, the variant chimeric receptor includes i) the sequence of amino acids set forth in any of SEQ ID NOS: 114-134 and 183; ii) a functional variant thereof including a sequence of amino acids that exhibits at least 95%, 96%, 97%, 98%, or 99% sequence identity to the sequence of amino acids set forth in any of SEQ ID NOS: 114-134 and 183 and that include the modification(s): ii) or is a functional portion of i) or ii) and includes the modification(s).

In some embodiments, the modified junction region includes no more than 1, 2, 3, 4, 5, 6, 7, 8, 9 or 10 amino acid modifications compared to the junction region of the reference chimeric receptor.

In some embodiments, the first domain or second domain is a transmembrane domain and the corresponding domain in the variant chimeric receptor includes a substantially hydrophobic hydropathy profile and/or has a positive grand average of hydropathy (GRAVY) value. In some embodiments, the GRAVY value is greater than 0, 0.25, 0.5, 0.75, 1, 1.1, 1.2, 1.3, 1.4, 1.5, 1.6, 1.7, 1.8, 1.9, 2.0, 2.1, 2.2 or greater.

In some embodiments, the first domain or second domain includes an intracellular signaling domain and the corresponding domain in the variant chimeric receptor is capable of inducing the activation or cellular localization of a TRAF and/or is capable of inducing TRAF-mediated signaling. In some embodiments, the intracellular signaling domain is a 4-1BB co-stimulatory signaling domain and/or the TRAF is selected from among TRAF1, TRAF2 or TRAF3. In some embodiments, the variant chimeric receptor includes amino acids TTQE at positions corresponding to 49-52 and/or amino acids PEEE at positions corresponding to residues 60-63, each with reference to numbering set forth in SEQ ID NO:5.

In some embodiments, the HLA is an HLA class I and/or an HLA class II. In some embodiments, the HLA class I is selected from an HLA allele set forth in Table 1A and/or the HLA class II allele is selected from an HLA allele set forth in Table 1B. In some embodiments, the HLA class I allele is selected from among HLA-A*02:01, HLA-A*03:01, HLA-A*11:01 and HLA-B*08:01.

In some embodiments, the HLA includes a plurality of HLA molecules and average binding affinities to one or more of the plurality of HLA molecules is lower and/or the number of peptide fragments that individually bind to one or more of the plurality of HLA molecules is reduced. In some embodiments, the plurality of HLA molecules is selected from a plurality of HLA class I molecules that represent greater than 50%, greater than 60%, greater than 70%, greater than 80%, greater than 90%, greater than 95% or greater than 99% of the HLA class I molecules in the worldwide population or in the Caucasian population: a plurality of HLA class II molecules that represent greater than 50%, greater than 60%, greater than 70%, greater than 80%, greater than 90%, greater than 95% or greater than 99% of the HLA class II molecules in the worldwide population or in the Caucasian population; or a plurality of HLA class I molecules and HLA class II molecules that represent greater than 50%, greater than 60%, greater than 70%, greater than 80%, greater than 90%, greater than 95% or greater than 99% of the HLA class I molecules and HLA class II molecules in the worldwide population or in the Caucasian population.

In some embodiments, the binding affinity is as determined in vitro.

In some embodiments, the variant chimeric receptor exhibits reduced immunogenicity compared to the reference chimeric receptor upon administration to a human subject, optionally wherein the subject has received administration of the reference chimeric receptor. In some embodiments, the reduced immunogenicity includes a reduced CD4+ T cell immune response and/or a reduced CD8+ T cell immune response.

In some embodiments, the reference chimeric receptor further includes an extracellular ligand-binding domain; and/or the variant chimeric receptor further includes an extracellular ligand-binding domain. In some embodiments, the variant chimeric receptor is a chimeric antigen receptor (CAR), wherein the ligand-binding domain is an antigen-binding domain. In some embodiments, the antigen-binding domain is an antibody or an antibody fragment. In some embodiments, the antigen-binding domain is an antibody fragment that is a single chain fragment. In some embodiments, the fragment includes antibody variable regions joined by a flexible immunoglobulin linker. In some embodiments, the antibody fragment includes an scFv.

In some embodiments, the ligand-binding domain specifically binds an antigen that is associated with a disease or disorder. In some embodiments, the disease or disorder is an infectious disease or condition, an autoimmune disease, an inflammatory disease or a tumor or a cancer: the ligand-binding domain specifically binds to a tumor antigen; and/or the ligand-binding domain specifically binds to an antigen selected from the group including ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) and cyclin A1 (CCNA1).

In some embodiments, the reference chimeric receptor further includes an activating cytoplasmic signaling domain; and/or the variant chimeric receptor further includes an activating cytoplasmic domain. In some embodiments, the activating cytoplasmic domain includes a T cell receptor (TCR) component and/or includes an immunoreceptor tyrosine-based activation motif (ITAM). In some embodiments, the activating cytoplasmic signaling domain is or includes a cytoplasmic signaling domain of a zeta chain of a CD3-zeta (CD3ζ) chain or a functional variant or signaling portion thereof.

In some embodiments, the reference chimeric receptor includes from its N to C terminus in order: an extracellular ligand-binding domain, the first domain that is a transmembrane domain, the second domain that is an intracellular costimulatory domain and an activating cytoplasmic signaling domain; and/or the variant chimeric receptor includes from its N to C terminus in order: an extracellular ligand-binding domain, a transmembrane domain, a intracellular costimulatory domain and an activating cytoplasmic signaling domain, wherein the transmembrane domain and intracellular costimulatory domain are joined in contiguous sequence at a junction to form the modified junction region.

In some embodiments, provided herein is a nucleic acid molecule encoding any of the variant chimeric receptor described herein. In some embodiments, provided herein is a vector containing the nucleic acid molecule. In some embodiments, the vector is a viral vector. In some embodiments, the vector is a retroviral vector, which optionally is a lentiviral vector or a gammaretroviral vector.

In some embodiments, provided herein is an engineered cell including the nucleic acid or the vector of any of the embodiments described herein or expressing the chimeric receptor of any of chimeric receptors described herein. In some embodiments, the engineered cell is a T cell. In some embodiments, the engineered cell is a CD4+ T cell and/or a CD8+ T cell.

In some embodiments, provided herein is a composition including the engineered cells of any of the embodiments described herein, and optionally a pharmaceutically acceptable buffer.

In some embodiments, provided herein is a method of treatment including administering the cell or the composition of any of the embodiments described herein to a subject having a disease or condition. In some embodiments, the chimeric receptor specifically binds to a ligand or antigen associated with the disease or condition. In some embodiments, the disease or condition is a cancer, a tumor, an autoimmune disease or disorder, or an infectious disease.

In some embodiments, the genetically engineered T cells in the composition exhibit increased or longer expansion and/or persistence in the subject than in a subject administered the same or about the same dosage amount of a reference cell composition expressing the reference chimeric receptor. In some embodiments, the increase is at least 1.2-fold, 1.5-fold, 2-fold, 3-fold, 4-fold, or 5-fold. In some embodiments, the increase is observed or is present within a month, within two months, within six months or within one year of administering the cells.

BRIEF DESCRIPTION OF THE DRAWINGS

FIG. 6 depicts the amino acid sequence of an exemplary CD28-4-1BB sequence of SEQ ID NO: 5. Amino acids corresponding to the CD28 transmembrane domain are indicated by a solid line with arrows indicating the beginning and end positions: amino acids of the exemplary 4-1BB costimulatory domain are indicated by a dashed line with arrows indicating the beginning and end positions: amino acids of the exemplary junction region are indicated by a dashed and dotted line with arrows indicating the beginning and end positions and by italics. The two amino acids immediately flanking the junction site are indicated by a box. Exemplary amino acids that in some embodiments are targeted for modification, including K28. R31, and L34, are bolded and underlined. Regions of acidic residues that may be involved in 4-1BB-mediated TRAF-binding and signaling are indicated by a double underline.

DETAILED DESCRIPTION

Figure 1:
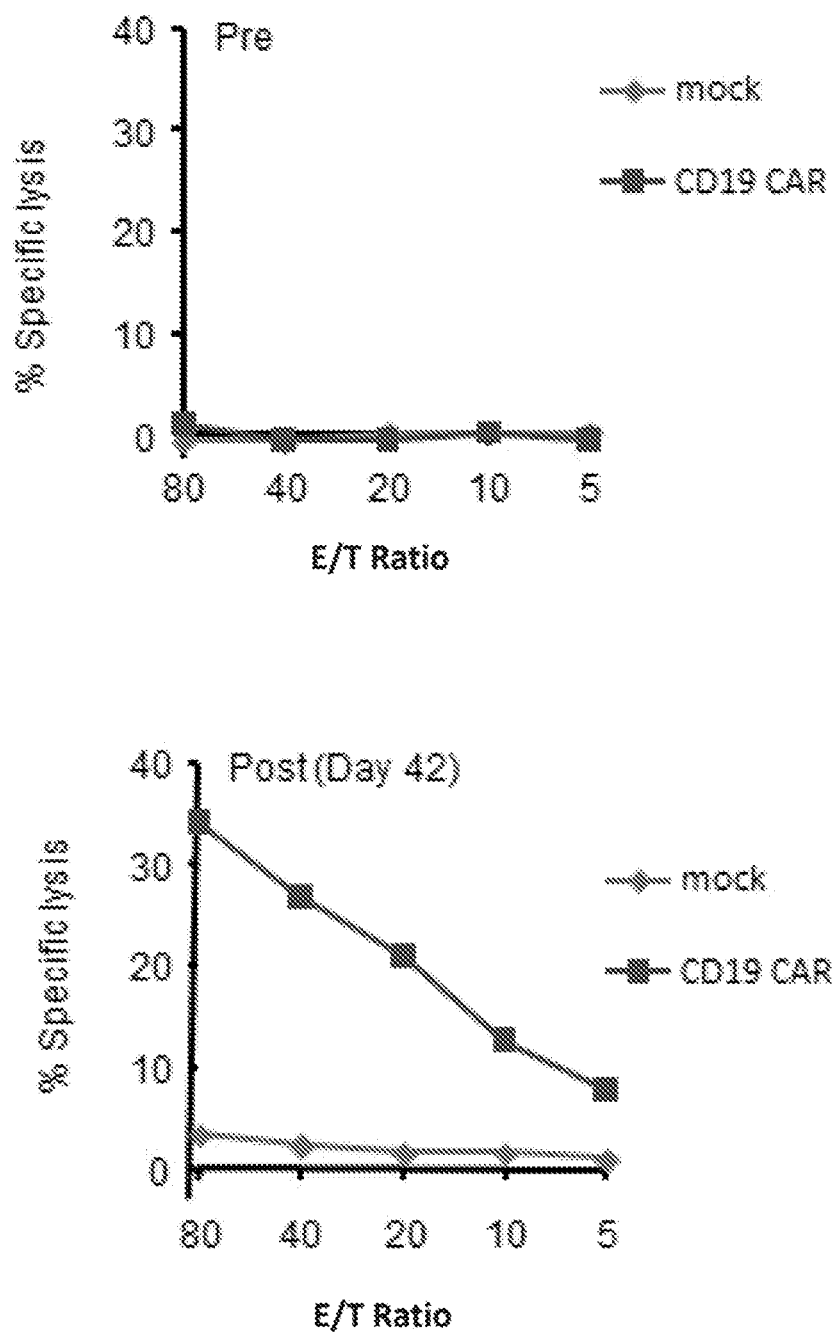
FIG. 1 shows results from an exemplary chromium release assay detecting the presence of a cytolytic immune response specific for CAR-expressing cells following administration of anti-CD19 CAR-expressing cells in a human subject. Results are shown for mixed-lymphocyte cultures containing peripheral blood mononuclear cells (PBMCs) derived from the subject pre-infusion (left panel) and post-infusion (right panel) with the CAR-expressing cells, in the presence of either CAR-expressing ("CD19-CAR") and non-CAR-expressing ("Mock"). "E/T"=effector to target cell ratio.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided are recombinant receptors, including chimeric receptors, e.g. chimeric antigen receptors, that exhibit one or more amino acid sequence differences compared to a reference chimeric receptor. In some embodiments, the provided variant chimeric receptors contain a modified junction region containing one or more modifications (e.g. amino acid insertions, deletions or amino acid replacements) compared to a junction region of a reference chimeric receptor such that peptide fragments (e.g. of 8 to 24 amino acids in length, e.g. 8 to 15 or 8 to 13 amino acids in length, such as about or 8, 9, 10, 11, 12, 13, 14, or 15 amino acids in length) derived from the modified junction region exhibit lower binding affinity for a human leukocyte antigen (HLA) compared to binding of corresponding peptide fragments derived from the reference junction region for the HLA. In some embodiments, a host immune response, e.g. humoral or cell-mediated, to the variant chimeric receptor following administration to the subject is reduced compared to the reference chimeric receptor. In some embodiments, the reduced immune response is a reduced detectable immune response against a region of the variant chimeric receptor containing the modified junction region.

In some embodiments, chimeric receptors, such as chimeric antigen receptor, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states (such as effector, long-lived memory, less-differentiated, and effector states), to provide effective and robust recall responses following clearance and re-exposure to target ligand or antigen, and avoid or reduce exhaustion, anergy, terminal differentiation, and/or differentiation into a suppressive state.

In some cases, adoptive therapy methods are not completely satisfactory in all of these respects. In some aspects, the provided embodiments are based on observations that the efficacy of adoptive cell therapy may be limited by the development of an immune response in the subject to the cells and/or construct administered. For example, in some cases, exposure to a chimeric receptor may be limited by host immune responses against the recombinant receptors expressed by the administered cells, which may prematurely eliminate the cells. It is observed that even in certain subjects having B cell malignancies, who often are immunocompromised, immune responses can be detected that are specific for regions of receptors expressed by cells administered in adoptive cell therapy. For example, as shown herein, subjects administered cells genetically engineered with a CAR developed a specific immune response to an immunogenic region of the chimeric region containing the junction between the transmembrane and costimulatory domain of the CAR.

In some aspects, the development of an immune response can reduce the exposure or persistence of T cells expressing the chimeric receptor in the course of adoptive therapy methods. Yet, observations indicate that, in some cases, increased exposure of the subject to administered cells expressing the recombinant receptors (e.g., increased number of cells or duration over time) may improve efficacy and therapeutic outcomes in adoptive cell therapy Preliminary analysis conducted following the administration of different CD19-targeting CAR-expressing T cells to subjects with various CD19-expressing cancers in multiple clinical trials revealed a correlation between greater and/or longer degree of exposure to the CAR-expressing cells and treatment outcomes. Such outcomes included patient survival and remission, even in individuals with severe or significant tumor burden.

Further, in some cases, once such a host immune response develops, either acquired or innate, it may not be feasible or effective to attempt to increase exposure or provide retreatment of subjects by administering a subsequent dose of cells expressing the same recombinant receptor. Once such an immune response has developed against the receptor, administration of such a second or subsequent dose of cells expressing the same receptor or one with similar immunogenic epitopes may result in rapid elimination of the cells before they have had a chance to expand and/or persist to an effective or substantial degree. Thus, it would be advantageous to minimize unwanted immune responses that may destroy or interfere with the activity of engineered cells used in adoptive cell therapy methods, thereby diminishing the effectiveness of the treatment.

Generally, chimeric receptors include a plurality of different domains, such as a plurality of domains present in molecules endogenous to a subject. For example, CARs are molecules that include an extracellular antigen-recognition domain that specifically binds to a target antigen and an intracellular signaling domain comprising an ITAM (e.g. CD3-zeta intracellular signaling domain). In some embodiments, the extracellular antigen-recognition domain comprises an antibody or antigen-binding fragment (e.g. scFv). A CAR also can contain a transmembrane domain and/or endodomain between the extracellular recognition domain and signaling domain, which can include transmembrane and/or intracellular signaling domains of a co-stimulatory molecule, such as a CD28 or 4-1BB co-stimulatory molecule. In some cases, such domains can be connected by linkers.

In some cases, the plurality of domains are not normally present adjacent to each other in sequence in an endogenous molecule in a subject. For example, in some embodiments, a first domain and a second domain of a chimeric receptor that are joined at a junction can create a contiguous sequence of amino acids that may not be present in a subject, particularly where such two domains do not naturally occur adjacent together in the same protein and/or are separated by a synthetic linker. In some cases, this can result in the presence of a non-native sequence that is not identical to a sequence present in an endogenous molecule of the host in the portion of the sequence of a chimeric receptor, such as a CAR, containing the junction between two domains.

In some cases, a junction region that contains potential peptide epitopes spanning the junction of the two domains can be immunogenic and result in the generation of an immune response upon administration to a subject of a chimeric receptor containing the junction region. In some embodiments, the junction region can include, e.g. once processed in connection with antigen presentation for display on an HLA molecule, a plurality of individual overlapping peptide fragments of contiguous sequence of about 8 to 24 amino (e.g. 8 to 15 amino acids or 8 to 13 amino acids, such as about or 8, 9, 10, 11, 12, 13, 14, 15 or more amino acids) directly C-terminal of the junction that joins a first domain and a second domain of the chimeric receptor and/or of about 8 to 24 amino acids (e.g. 8 to 15 amino acids or 8 to 13 amino acids, such as about or 8, 9, 10, 11, 12, 13, 14, 15 or more amino acids) directly N-terminal of the junction, which peptide fragments each can include or span the junction of the two domains. Thus, in some cases, the junction region can contain a plurality of potential peptide epitopes that may exhibit a binding affinity for an HLA molecule and/or be capable of inducing an immune response.

In some embodiments, the peptide fragment is recognized by the immune response to induce or initiate a detectable immune response, e.g. humoral or cell-mediated, against such peptide sequence. In some embodiments, the peptide fragment can associate or bind with an MHC molecule expressed on a cell for recognition by a T cell receptor (TCR). In some embodiments, the peptide epitope, under certain conditions, can elicit an immune response in an animal, such as a T cell response. For example, in some cases, T cells expressing a TCR that recognizes a T cell epitope in the context of an MHC molecule can become stimulated, thereby leading to T cell responses, such as T cell proliferation, lymphokine secretion, cytotoxic responses, local inflammatory reactions, recruitment of additional immune cells and/or activation of B cells leading to production of antibodies against the protein containing the peptide epitope, such as a chimeric receptor. It is within the level of a skilled artisan to identify a peptide epitope of any chimeric receptor.

In some embodiments, the provided methods reduce or lessen an immune response in a subject administered with cells expressing the variant chimeric receptor, such as CAR, compared to the immune response generated in the subject administered with cells expressing the reference (unmodified) chimeric receptor, such as reference or unmodified CAR. In some embodiments, the subject does not exhibit or exhibits a reduced immune response or a particular type or degree of immune response, against the variant chimeric receptor or a modified junction region of the chimeric receptor, such as following the administration of the cells expressing the receptor. The type of immune response may be a detectable immune response, a humoral immune response, and/or a cell-mediated immune response.

In some embodiments, the provided methods achieve increased persistence of genetically engineered T cells expressing the variant chimeric receptor, such as a variant CAR, when administered to a subject. In some embodiments, a genetically engineered cell with increased persistence exhibits better potency in a subject to which it is administered. In some embodiments, the persistence of genetically engineered cells expressing the variant chimeric receptor, such as variant CAR-expressing T cells, in the subject upon administration is greater as compared to that which would be achieved by alternative methods, such as those involving administration of genetically engineered cells expressing the reference or unmodified chimeric receptor. In some aspects, the persistence of administered cells is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the chimeric receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

Also provided are compositions containing the variant chimeric receptor or engineered cells expressing such variant chimeric receptor. Also provided are methods for administering such variant chimeric receptors and compositions to subjects, including cells expressing the variant chimeric receptors and compositions of such cells to subjects, such as for adoptive cell therapy.

II. Variant Chimeric Receptors

Provided herein are variant chimeric receptors that contain a modified junction region compared to a junction region of a reference chimeric receptor. In some embodiments, the junction region is a region containing a contiguous sequence of amino acids on each side of a junction between a first and second domain. In some embodiments, by virtue of one or more modifications present in the modified junction region, the variant chimeric receptor contains a domain corresponding to the first domain of the reference chimeric receptor and/or a domain corresponding to the second domain of the reference chimeric receptor that is modified by one or more amino acid differences (e.g. mutations).

In some embodiments, the variant chimeric receptor contains a modified junction region compared to a junction region of a reference chimeric receptor in which one or more amino acid residues at a position 8 to 24 amino acids (e.g. 8 to 15 amino acids or 8 to 13 amino acids, such as about or 8, 9, 10, 11, 12, 13, 14, 15 or more amino acids) directly C-terminal of the junction that joins a first domain and a second domain of the reference chimeric receptor and/or at a position 8 to 24 amino acids (e.g. 8 to 15 amino acids or 8 to 13 amino acids, such as about or 8, 9, 10, 11, 12, 13, 14, 15 or more amino acids) directly N-terminal of the junction are modified, such as by insertion, deletion or amino acid replacement. In some embodiments, the variant chimeric receptor contains up to 1, 2, 3, 4, 5, 6, 7, 8, 9, 10, 11, 12, 13, 14, 15, 16, 17, 18, 19 or 20 amino acid differences or modifications in the modified junction region compared to the junction region in the reference chimeric receptor.

In some embodiments, the variant chimeric receptor contains a domain of at least 85%, 86%, 87%, 88%, 89%, 90%, 91%, 92%, 93%, 94%, 95%, 96%, 97%, 98%, 99% or more sequence identity to the first domain of the reference chimeric receptor and/or contains a domain of at least 85%, 86%, 87%, 88%, 89%, 90%, 91%, 92%, 93%, 94%, 95%, 96%, 97%, 98%, 99% or more sequence identity to the second domain of the reference chimeric receptor. In some embodiments, the variant chimeric receptor contains a domain that is identical in sequence to the first domain of the reference chimeric receptor and contains a domain of at least 85%, 86%, 87%, 88%, 89%, 90%, 91%, 92%, 93%, 94%, 95%, 96%, 97%, 98%, 99% or more sequence identity to the second domain of the reference chimeric receptor. In some embodiments, the variant chimeric receptor contains a domain of at least 85%, 86%, 87%, 88%, 89%, 90%, 91%, 92%, 93%, 94%, 95%, 96%, 97%, 98%, 99% or more sequence identity to the first domain of the reference chimeric receptor and contains a domain that is identical in sequence to the second domain of the reference chimeric receptor. In some embodiments, at least one or both of the domains present in the variant chimeric receptor is modified compared to the first domain and/or the second domain of the reference chimeric receptor in the portion containing the modified junction region.

In some embodiments, the variant chimeric receptor has at least 85%, 86%, 87%, 88%, 89%, 90%, 91%, 92%, 93%, 94%, 95%, 96%, 97%, 98%, 99% or more sequence identity to the reference chimeric receptor. In some embodiments, the variant chimeric receptor contains up to 1, 2, 3, 4, 5, 6, 7, 8, 9, 10, 11, 12, 13, 14, 15, 16, 17, 18, 19 or 20 amino acid differences or modifications (e.g. amino acid insertions, deletions or replacements) compared to the reference chimeric receptor.

In some embodiments, the first and/or second domain of the reference chimeric receptor (e.g. reference CAR) is a domain of a natural endogenous human protein or a domain having 100% identity with a domain or function portion thereof of a natural or endogenous protein. In some embodiments, the first domain and second domain are not present in the same molecule in vivo in a human subject. In some embodiments, the first domain and second domain are not present in a single natural or endogenous human protein or polypeptide.

In some embodiments, the first and/or second domain is or comprises an extracellular binding domain, a hinge domain, a transmembrane domain, or an intracellular signaling domain or functional portions thereof. In some embodiments, the intracellular signaling domain is or comprises a costimulatory signaling domain, such as a CD28, 4-1BB, or ICOS co-stimulatory signaling domain. In some embodiments, the intracellular signaling domain is or comprises an activating cytoplasmic signaling domain, such as a domain that is or includes a T cell receptor (TCR) component and/or that contains an immunoreceptor tyrosine-based activation motif (ITAM). In some cases, the activating cytoplasmic domain is or comprises a cytoplasmic signaling domain of a zeta chain of a CD3-zeta (CD3ζ) chain or a functional variant or signaling portion thereof.

In some embodiments, the reference chimeric receptor is a CAR. In some embodiments, the chimeric receptors, such as a CAR, contains from its N-terminus to C-terminus in order: an extracellular ligand-binding domain, a transmembrane domain and an intracellular signaling domain. In some embodiments, the intracellular signaling domain is or includes an activating signaling domain (e.g. a components of TCR and/or containing an ITAM, for example a CD3-zeta signaling domain). In some embodiments, the intracellular signaling domain is or includes a costimulatory signaling domain (e.g. a CD28, 4-1BB or ICOS signaling domain). In some embodiments, the intracellular signaling domain contains only one of the costimulatory signaling domain or activating signaling domain or contains both domains in either order. In some embodiments, the intracellular signaling domain contains both the costimulatory signaling domain and activating signaling domain.

In some embodiments, the reference chimeric receptor contains a junction region of a first and second domain that is immunogenic. In some embodiments, the immunogenic region includes one or more peptide epitopes (also called a T cell epitope). In some cases, a junction region that contains potential peptide epitopes spanning the junction of the two domains can be immunogenic and result in the generation of an immune response upon administration to a subject of a chimeric receptor containing the junction region. In some embodiments, the junction region can include, e.g. once processed in connection with antigen presentation for display on an HLA molecule, a plurality of individual overlapping peptide fragments of contiguous sequence of about 8 to 24 amino (e.g. 8 to 15 amino acids or 8 to 13 amino acids, such as about or 8, 9, 10, 11, 12, 13, 14, 15 or more amino acids) directly C-terminal of the junction that joins a first domain and a second domain of the chimeric receptor and/or of about 8 to 24 amino acids (e.g. 8 to 15 amino acids or 8 to 13 amino acids, such as about or 8, 9, 10, 11, 12, 13, 14, 15 or more amino acids) directly N-terminal of the junction, which peptide fragments each can include or span the junction of the two domains. Thus, in some cases, the junction region can contain a plurality of potential peptide epitopes that may exhibit a binding affinity for an HLA molecule and/or be capable of inducing an immune response.

In some embodiments, an immunogenic region, such as a junction region, of a chimeric receptor can be identified. In some embodiments, the immunogenic region can be identified by its ability to bind to an MHC molecule or by its ability to elicit an immune response under certain conditions. In some embodiments, overlapping peptides of a chimeric receptor, such as overlapping 8mer to 20 mer peptides, such as 9mers, 10mers, 11mers, 12mers, 13mers, 14mers or 15mers can be assessed for MHC binding using algorithmic or other computational methods, such as described below. In some embodiments, a chimeric receptor can be assessed to determine if it is immunogenic by assessing an immune response in a subject to which it has been administered, such as a subject administered cells genetically engineered with the chimeric receptor (e.g. CAR). Exemplary methods of assessing immune responses are described below.

In some embodiments, the at least one peptide epitope is capable of binding to a major histocompatibility complex (MHC) molecule, such as a class I or class II protein, which are molecules that contain a polymorphic peptide binding site or binding groove that can, in some cases, complex with peptide fragments of polypeptides, including peptides processed by the cell machinery. In some embodiments, the peptide epitope is capable of binding to an MHC molecule that is a human MHC molecule. In some embodiments, the MHC molecule is a human leukocyte antigen (HLA) molecule. In some embodiments, the at least one peptide epitope exhibits a binding affinity (e.g. IC50) for an HLA molecule, such as an HLA class I molecule or an HLA class II molecule. In some embodiments, the junction region of the reference chimeric receptor contains a peptide epitope that exhibits a binding affinity of less than 1000 nM, less than 500 nM or less than 50 nM.

In some embodiments, at least one or more peptide epitopes of a junction region of a reference chimeric receptor is an MHC class II epitope. In some embodiments, peptides that bind to MHC class II molecules can be between 8 and 20 amino acids in length, including between 10) and 17 amino acids in length, such as or about at least or at least or about 10, 11, 12, 13, 14, 15, 16 or 17 amino acids in length, for example about 15 amino acids in length. In some embodiments, the peptides that bind to MHC class II molecules can be longer than 20 amino acids. In some embodiments, the peptide lies in an extended conformation along the MHC II peptide-binding groove. In some embodiments, the MHC II peptide-binding groove is open at both ends. In some embodiments, the peptide is held in place at least in part by main-chain atom contacts with conserved residues that line the peptide-binding groove. In some embodiments, the MHC class II is an αβ dimer that can be or include any MHC class II allelic protein known to be present in a subject, such as a human subject. In some embodiments, the MHC allele can be, but is not limited to, DR1, DR3, DR4, DR7, DR52, DQ1, DQ2, DQ4, DQ8 and DPI. In some embodiments, the MHC class II allele can be any set forth in Tables 1B, including isotype matched alpha and beta associations or mixed-isotype heterodimers combining alpha and beta chains of different alleles. In some embodiments, the MHC class II can be a dimer that is or includes an alpha and/or beta allele from among HLA-DPA1*0103, HLA-DPA1*0201, HLA-DPB1*0101, HLA-DPB1*0301, HLA-DPB1*0401, HLA-DPB*0402, HLA-DPB1*1501, HLA-DRA*0101, HLA-DRB1*0) 101, HLA-DRB1*0102, HLA-DRB*0) 301, HLA-DRB*0) 701, HLA-DRB*0401, HLA-DRB1*1101, HLA-DRB1*1104, HLA-DRB*1501, and/or HLA-DQB1*0201.

In some embodiments, the at least one peptide epitope of a junction region of a reference chimeric receptor is an MHC class I epitope. In some embodiments, peptides that bind to MHC class I molecules can be between 7 to 15 amino acids in length. In some embodiments, peptides that bind to MHC class I molecule can be between 8 to 13 amino acids in length. In some embodiments, the binding of the peptide is stabilized at its two ends by contacts between atoms in the main chain of the peptide and invariant sites in the peptide-binding groove of all MHC class I molecules. In some embodiments, there are invariant sites at both ends of the groove which bind the amino and carboxy termini of the peptide. In some embodiments, variations in peptide length can be accommodated by a kink in the peptide backbone. In some embodiments, the kink includes proline or glycine residues, which may allow flexibility. In some embodiments, the MHC class I allele can be any known to be present in a subject, such as a human subject. In some embodiments, the MHC class I allele is an HLA-A2, HLA-A1, HLA-A3, HLA-A24, HLA-A28, HLA-A31, HLA-A33, HLA-A34, HLA-B7, HLA-B45 or HLA-Cw8 allele. In some embodiments, the MHC class I allele can be any set forth in Tables 1A, which are among the most frequent MHC class I alleles (Solberg et al., (2008) *Hum Immunol.* 2008 July: 69 (7): 443-6). In some embodiments, the HLA class I allele is HLA-A*02:01, HLA-A*03:01, HLA-A*11:01 or HLA-B*08:01.

In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23%

HLA-A*0201, 45% HLA-A*0207, 8% HLA-A*0206 and 23% HLA-A*0203. In some embodiments, the MHC molecule is HLA-A*0201.

In some embodiments, the variant chimeric receptor can contain from its N-terminus to C-terminus in order: an extracellular ligand-binding domain, a transmembrane domain and an intracellular signaling domain, which optionally can include a costimulatory signaling domain (e.g. CD28, 4-1BB or ICOS) and/or an activating signaling domain (e.g. a components of TCR and/or containing an ITAM, for example a CD3-zeta signaling domain) each alone as part of the intracellular signaling domain or in either order, in which the variant chimeric receptor contains a modification at one or more amino acid residues within a contiguous portion of 8 to 24 amino acids (e.g. 8 to 15 amino acids or 8 to 13 amino acids, such as about or 8, 9, 10, 11, 12, 13, 14, 15 or more amino acids) on either side (N-terminal and/or C-terminal) of the junction.

In some embodiments, the features of a reference chimeric receptor can be any described in subsection 1 below. In some embodiments, the features of a variant chimeric receptor also can be any as described in subsection 1 below, except that the variant chimeric receptor contains one or more modifications (e.g. insertions, deletions or replacements) in a modified junction region as described.

1 Chimeric Receptors

Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446, 179, 6,410,319, 7,070,995, 7,265,209, 7,354,762, 7,446, 191, 8,324,353, and 8,479,118, and European patent application number EP2537416, and/or those described by Sadelain et al., Cancer Discov. 2013 April; 3 (4): 388-398; Davila et al. (2013) *PLOS ONE* 8 (4): e61338: Turtle et al., *Curr. Opin. Immunol.*, 2012 October; 24 (5): 633-39; Wu et al., *Cancer,* 2012 Mar. 18 (2): 160-75. In some embodiments, the genetically engineered antigen receptors include a CAR as described in U.S. Pat. No. 7,446,190, and those described in International Patent Application Publication No.: WO/2014055668 A1. In some embodiments, similar methods for the construction and introduction or transfer into immune cells can be employed for the provided chimeric receptors.

In some embodiments, the chimeric receptor includes a ligand-binding domain that binds, such as specifically binds, to an antigen (or a ligand). Among the antigens targeted by chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells. In some embodiments, the antigen (or a ligand) is a tumor antigen or cancer marker. In some embodiments, the antigen (or a ligand) is or includes orphan tyrosine kinase receptor ROR1, tEGFR, Her2, L1-CAM, CD19, CD20, CD22, BCMA, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. In some embodiments, the antigen is a pathogen-specific antigen. In some embodiments, the antigen is a viral antigen (such as a viral antigen from HIV, HCV, HBV, etc.), bacterial antigens, and/or parasitic antigens.

In some embodiments, the chimeric receptor is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the chimeric receptor typically includes in its extracellular potion on or more ligand binding domains.

In some embodiments, the chimeric receptor is a CAR. In some embodiments, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The term "antibody" herein is used in the broadest sense and includes polyclonal and monoclonal antibodies, including intact antibodies and functional (antigen-binding) antibody fragments, including fragment antigen binding (Fab) fragments, F(ab') 2 fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab) 2. Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2. IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the CAR contains an antibody or an antigen-binding fragment (e.g. scFv) that specifically recognizes an antigen, such as an intact antigen, expressed on the surface of a cell.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFV or other antibody forms can be generated, for example, in which members of the library are mutated at one or more residues of a CDR or CDRs. Exemplary of such methods are known in the art (see e.g. US published application No. US20020150914, US2014/0294841; and Cohen C J. et al. (2003) J Mol. Recogn. 16:324-332).

In some embodiments, the extracellular portion of the CAR, such as an antibody portion thereof, further includes a spacer, such as a spacer region between the antigen-recognition component, e.g. scFv, and a transmembrane domain. The spacer may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153. international patent application publication number WO2014031687, or U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 158. In some embodiments, the spacer has the sequence set forth in SEQ ID NO: 107. In some embodiments, the spacer has the sequence set forth in SEQ ID NO: 108. In some embodiments, the constant region or portion is of IgD. In some embodiments, the spacer has the sequence set forth in SEQ ID NO: 109. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 107, 108 or 109.

The extracellular ligand binding, such as antigen recognition domain, generally is linked to one or more intracellular signaling components, such as signaling components that mimic activation through an antigen receptor complex, such as a TCR complex, in the case of a CAR, and/or signal via another cell surface receptor. In some embodiments, a transmembrane domain links the extracellular ligand binding and intracellular signaling domains. In some embodiments, the CAR includes a transmembrane domain fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5 (215) (December 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR ((EGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 111 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 111. An exemplary T2A linker sequence comprises the sequence of amino acids set forth in SEQ ID NO: 110 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 110.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding: in some aspects, a second-generation CARs is one that provides such a signal and costimulatory signal, such as one including an intracellular signaling domain from a costimulatory receptor such as CD28 or CD137: in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD32) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the transmembrane domain of the receptor, e.g., the CAR is a transmembrane domain of human CD28 or variant thereof, e.g., a 27-amino acid transmembrane domain of a human CD28 (Accession No.: P10747.1). In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 2 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 2: in some embodiments, the transmembrane-domain containing portion of the recombinant receptor comprises the sequence of amino acids set forth in SEQ ID NO: 104 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 41BB.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 112 or 113 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 112 or 113. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 3 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 3.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 4, 105 or 159 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 4, 105 or 159.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 108. In some embodiments, the spacer is an Ig hinge, e.g., an IgG4 hinge, linked to a CH3 domain only, such as set forth in SEQ ID NO: 107. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes: an extracellular ligand-binding portion, such as an antigen-binding portion, such as an antibody or fragment thereof, including sdAbs and scFvs, that specifically binds an antigen, e.g. an antigen described herein: a spacer such as any of the Ig-hinge containing spacers; a transmembrane domain that is a portion of CD28 or a variant thereof; an intracellular signaling domain containing a signaling portion of 4-1BB or functional variant thereof; and a signaling portion of CD3 zeta signaling domain or functional variant thereof.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element and/or a tEGFR sequence set forth in SEQ ID NO: 110 and/or 111, respectively, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 110 and/or 111. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802, 374).

2. Exemplary Modifications of a Chimeric Receptor

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises an extracellular ligand binding domain or a portion thereof and a second domain that is or comprises a hinge domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a hinge domain or a portion thereof and a second domain that is or comprises a transmembrane domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a transmembrane domain or a portion thereof and a second domain that is or comprises a costimulatory signaling domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a costimulatory signaling domain or a portion thereof and a second domain that is or comprises an activating cytoplasmic signaling domain or a portion thereof, joined in contiguous sequence at a junction.

In some embodiments, the first domain of the reference chimeric receptor is or comprises a transmembrane domain or a portion thereof. In some embodiments, the transmembrane domain include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. In some embodiments, the transmembrane domain is derived from a human protein or is human. In some embodiments, the second domain of the reference chimeric receptor is or comprises a costimulatory signaling domain, which is directly linked or joined to the transmembrane domain. In some embodiments, the costimulatory signaling domain is or comprises a signaling domain of CD28, 4-1BB, OX40, DAP10, and ICOS. In some embodiments, the costimulatory domain is derived from a human protein or is human.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a CD28 transmembrane domain or a portion thereof and a second domain that is or comprises a 4-1BB costimulatory signaling domain or a portion thereof, joined in contiguous sequence at a junction. In some embodiments, the CD28 transmembrane domain is or comprises the sequence of amino acids set forth in SEQ ID NO:2, 103 or 104 or is a functional portion or variant thereof comprising a sequence that exhibits at least 85%, 86%, 87%, 88%, 89%, 90%, 91%, 92%, 93%, 94%, 95%, 96%, 97%, 98%, 99% or more sequence identity to SEQ ID NO:2, 103 or 104. In some embodiments the 4-1BB signaling domain is or comprises the sequence of amino acids set forth in SEQ ID NO:3 or a functional portion or variant thereof comprising a sequence that exhibits at least 85%, 86%, 87%, 88%, 89%, 90%, 91%, 92%, 93%, 94%, 95%, 96%, 97%, 98%, 99% sequence identity to SEQ ID NO:3. In some embodiments, the first domain and second domain together comprise or have the sequence of amino acids set forth in SEQ ID NO:5 or a functional portion or variant thereof comprising a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:5. In some embodiments, the first domain and second domain of the reference chimeric receptor together have or comprise the sequence of amino acids set forth in SEQ ID NO:5.

In some embodiments, the variant chimeric receptor comprises a modified junction region that is less than 100% identical in sequence to SEQ ID NO: 137 but greater than 85%, 86%, 87%, 88%, 89%, 90%, 91%, 92%, 93%, 94%, 95% or 96% identical to SEQ ID NO:137 and includes the modification(s), such as any as described. In some embodiments, the variant chimeric receptor has or comprises a sequence of amino acids that is less than 100% sequence identity to SEQ ID NO:5 but greater than 85%, 86%, 87%, 88%, 89%, 90%, 91%, 92%, 93%, 94%, 95% or 96% identical to SEQ ID NO:5 and includes the modification(s), such as any as described. In some embodiments, the variant chimeric receptor has or comprises a sequence of amino acids that is less than 100% identical in sequence to SEQ ID NO: 160 but greater than 85%, 86%, 87%, 88%, 89%, 90%, 91%, 92%, 93%, 94%, 95% or 96% identical to SEQ ID NO: 160 and includes the modification(s), such as any as described. In some embodiments, the variant chimeric receptor has or comprises a modified junction region comprising the sequence of amino acids set forth in any of SEQ ID NOS: 138-157 and 184, a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 138-157 and 184, or a functional portion thereof, each that include the modification(s), such as any as described.

In some embodiments, the variant chimeric receptor does not contain a modification at or of a hydrophobic amino acid residue or within a hydrophobic portion in the transmembrane domain, such as the CD28 transmembrane domain. In some embodiments, the variant chimeric receptor contains one or more modifications at or of a hydrophobic amino acid residues or within a hydrophobic portion in the transmembrane domain, such as the CD28 transmembrane domain. In some embodiments, the one or more modifications is or comprises a substitution of the hydrophobic amino acid with another different hydrophobic amino acid residue. In some embodiments, the one or more modifications is not or does not comprise a modification at or of a hydrophobic amino acid residue or within a hydrophobic portion in the transmembrane domain other than a substitution with another hydrophobic amino acid residue.

In some cases, transmembrane domains contain one or more tryptophan residues that interact with the lipid bilayers of a membrane. In some cases, the one or more tryptophan residues can be located near the lipid-water interface. In some cases, the one or more tryptophan residues anchor or assist in anchoring the transmembrane domain within the membrane. See e.g. de Jesus and Allen, *Biochim Biophys Acta.* 2013 February; 1828 (2): 864-76. In some embodiments, the variant chimeric receptor does not contain a modification at one or both of a tryptophan residue in the transmembrane domain, such as the CD28 transmembrane domain. In some embodiments, the chimeric receptor does not contain a modification at an amino acid position corresponding to position 2 and/or position 26 with reference to numbering of SEQ ID NO: 5, each of which corresponds to a tryptophan in the reference chimeric receptor.

In some aspects, the hydrophobic character of a chimeric receptor, or a portion thereof, is assessed. In some embodiments, programs such as grand average of hydropathy (GRAVY) are used to assess global hydrophobicity of the chimeric receptor (e.g. variant chimeric receptor), or a portion thereof. In some embodiments, programs are used such as those available via ExPASy (Switzerland) to determine the global hydrophobicity score for a chimeric receptor, or portion thereof. In some aspects, the chimeric receptor comprises a transmembrane domain, which may have a hydrophobicity score indicating that the global character of this domain is hydrophobic. In some aspects, the chimeric receptor comprises one or more domains other than a transmembrane domain, which may have hydrophobicity scores indicating that the one or more other domains are globally hydrophilic. In some aspects, the hydrophobicity for each individual amino acid residue of a given protein sequence (e.g. chimeric receptor or portion thereof) is calculated based upon a hydrophobicity scale. Exemplary amino acid hydrophobicity scales include, but are not limited to, those calculated and/or reported by Kyte and Doolittle (1982), Engelman et al. (1986), Nozaki and Tanford (1971), Miyazawa and Jernigan (1996), Miyazawa and Jernigan (1999), and Black and Mould (1991). In some embodiments, hydrophobicity scales are reported or normalized such that hydrophilic residues, or peptides, are accorded a score below 0 and hydrophobic residues, or peptides, are accorded a score above 0. Thus, in some aspects, a transmembrane domain may have a global hydrophobicity score above 0, or may be comprised of individual residues with hydrophobicity scores above 0. In some embodiments, mutations or modifications to a residue, peptide, chimeric receptor, or portion thereof, are conservative with regard to the unmodified residue or peptide's hydrophobicity score.

In some embodiments, the variant chimeric receptor or a portion thereof, e.g. a portion containing the modified junction region and/or containing a domain in the variant chimeric receptor that corresponds to the transmembrane domain of the reference chimeric receptor, has a substantially hydrophobic hydropathy profile and/or has a positive grand average of hydropathy (GRAVY) value. In some embodiments, the GRAVY value is greater than 0, 0.25, 0.5, 0.75, 1, 1.1, 1.2, 1.3, 1.4, 1.5, 1.6, 1.7, 1.8, 1.9, 2.0, 2.1, 2.2 or greater.

In some embodiments, the variant chimeric receptor does not contain a modification at or of an amino acid residue involved in or necessary for the signaling of the costimulatory signaling domain, such as at or of an amino acid residue involved in or necessary for 4-1BB signaling. In general, costimulatory signaling involves interactions with TRAF molecules. In some embodiments, the variant chimeric receptor does not contain a modification at or of an amino acid residue that interacts with or is part of a binding motif for binding to a TRAF molecule. In some embodiments, the variant chimeric receptor does not contain a modification at or of an amino acid residue in the costimulatory signaling domain of the reference chimeric receptor that comprises the motif (P/S/A/T)X(Q/E)E. In some embodiments, the TRAF molecule is TRAF 1, TRAF2 and/or TRAF3. In some embodiments, the domain in the variant chimeric receptor that corresponds to the costimulatory signaling domain of the reference chimeric receptor is capable of inducing the activation or cellular localization of a TRAF and/or is capable of inducing TRAF-mediated signaling. In some embodiments, the variant chimeric receptor contains amino acids TTQE at positions corresponding to 49-52 and/or amino acids PEEE at positions corresponding to residues 60-63, each with reference to numbering set forth in SEQ ID NO:5.

In some embodiments, the variant chimeric receptor contains one or more amino acid modification within a portion between residue 13 and 42 or between amino acid residue 15 and 40, with reference to numbering set forth in SEQ ID NO:5.

In some embodiments, the modification is or includes insertion of one or more amino acid residues. In some embodiments, the one or more insertion is between amino acid residues adjacent to the junction between the domains. In some embodiments, the one or more amino acid insertions is between amino acid residues 27 and 28 with reference to numbering set forth in SEQ ID NO:5. In some embodiments, the one or more insertions can include insertion of up to 1, 2, 3, 4, 5, 6, 7, 8, 9, 10, 11, 12, 13, 14 or 15 amino acid residues. In some embodiments, the insertion is of 1, 2, 3, 4, or 5 amino acid residues. In some embodiments, the insertion is to any amino acid residues. In some embodiments, the insertion of is insertion of an asparagine (N).

In some embodiments, the modification is or includes one or more amino acid replacements at a residue corresponding to residue 28, 31 or 34 with reference to numbering set forth in SEQ ID NO:5. In some embodiments, the amino acid replacement can be to any other amino acid. In some embodiments, the amino acid replacement is to an amino acid residue that is leucine (L), asparagine (N), glutamine (Q), alanine (A), serine(S) or histidine (H). In some embodiments, the amino acid replacement is or corresponds to one or more of K28A, K28H, K28L, K28Q, K28S, R31A, R31H, R31L, R31N, R31S, L34A and L34S, with reference to numbering set forth in SEQ ID NO:5.

In some embodiments, the variant chimeric receptor contains a modified junction region with two or more, such as up to 2, 3, 4, 5, 6, 7, 8, 9, 10 or more amino acid modifications compared to a junction region of a reference chimeric receptor. In some embodiments, the amino acid modification includes amino acid replacements corresponding to two or more of K28A, K28H, K28L, K28Q, K28S, R31A, R31H, R31L, R31N, R31S, L34A and L34S, with reference to numbering set forth in SEQ ID NO:5. In some embodiments, the amino acid replacements are or correspond to amino acid replacements selected from among K28Q/R31A, K28Q/R31N, K28Q/R31S, K28Q/L34A, K28Q/L34S, R31N/L34A, R31N/L34S, K28Q/R31N/L34A, K28Q/R31N/L34S.

In some embodiments, the variant chimeric receptor has or comprises a modified junction region that has the sequence of amino acids set forth in any of SEQ ID NOS: 138-157 and 184, or a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 138-157 and 184, or a functional portion thereof, each that includes the modification(s).

In some embodiments, the variant chimeric receptor has or comprises the sequence of amino acids set forth in any of SEQ ID NOS: 114-134 and 183, a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 114-134 and 183, or a functional portion thereof, each that includes the modification(s).

3. Features of Variant Chimeric Receptors

In some embodiments, the variant chimeric receptor contains a modified junction region such that peptide fragments of or derived from such region exhibit a lower binding affinity for a human leukocyte antigen (HLA) and/or the region exhibits reduced immunogenicity, including following administration to a subject.

In some embodiments, a peptide fragment having the sequence of an 8-15 amino acid portion of the modified junction region has a binding affinity for a human leukocyte antigen (HLA) molecule that is lower than the binding affinity, for the same HLA molecule, of a peptide fragment having the sequence of the corresponding portion of the junction region of the reference chimeric receptor. In some embodiments, the peptide fragment of the corresponding portion of the junction region of the reference chimeric receptor has a binding affinity of less than 1000 nM, less than 500 nM or less than 50 nM.

In some embodiments, the average of the binding affinities of all 8-15 amino acid fragments, or of all 8, 9, 10, 11, 12, 13, 14, or 15 amino acid fragments, within the modified junction region for a human HLA molecule is lower than the average of the binding affinities of all 8-15 amino acid fragments, or of all 8, 9, 10, 11, 12, 13, 14, or 15 amino acid fragments, within the junction region of the reference chimeric receptor. In some embodiments, the binding affinity or average of binding affinities is more than 2-fold, more than 5-fold, more than 10-fold, more than 25-fold, more than 50-fold or more than 100-fold lower.

In some embodiments, the number of peptide fragments having the sequence of an 8-15 amino acid portion of the modified junction region that has a binding affinity for a human leukocyte antigen (HLA) of less than 1000 nM is reduced compared to the number of peptide fragments having the sequence of an 8-15 amino acid portion of the junction region of the reference chimeric receptor that has the same affinity for binding the same HLA. In some embodiments, the number of peptide fragments having the sequence of an 8-15 amino acid portion of the modified junction region that has a binding affinity for a human leukocyte antigen (HLA) of less than 500 nM is reduced compared to the number of peptide fragments having the sequence of an 8-15 amino acid portion of the junction region of the reference chimeric receptor that has the same affinity for binding the same HLA. In some embodiments, the number of peptide fragments having the sequence of an 8-15 amino acid portion of the modified junction region that has a binding affinity for a human leukocyte antigen (HLA) of less than 50 nM is reduced compared to the number of peptide fragments having the sequence of an 8-15 amino acid portion of the junction region of the reference chimeric receptor that has the same affinity for binding the same HLA.

In some embodiments, the binding affinity can be determined experimentally or algorithmically. In some embodiments, a peptide binding affinity for an MHC can be determined computationally, such as by using algorithms based on quantitative binding affinity models (Lafuente and Reche (2009) Current Pharmaceutical Design, 15:3209-3220). In some embodiments, the binding affinity can be determined in an in vitro assay.

In some embodiments, determining a peptide's binding affinity to an MHC molecule involves radioactivity or fluorescence competition binding assays. See, e.g. Ettinger et al., *J. Immunol.* 160:2365 (1998). In some embodiments, the competition assay yield a comparison of binding affinities of different peptides. Some MHC binding studies utilize detergent solubilized class I molecules from EBV transformed cell lines (see, e.g. Sette, A., et al., *Mol Immunol,* 31 (11): 813-22 (1994). In some embodiments, the competitive assay involves naturally loaded MHC, and the MHC molecule of interest can be purified away from other MHC molecules in the detergent lysate or be used in a mixture with other MHC molecules. In some embodiments, radiolabeled peptides can be identified that have a high affinity for the MHC molecule in question. In some embodiments, the affinity of additional "test" peptides for the MHC molecule in question is then determined by their ability to compete with the high affinity radiolabeled peptide.

In some embodiments, determining peptide affinity can involve a reconstitution assay, e.g. using "T2" cells, in which cells expressing an appropriate MHC allele are "stripped" of a native binding peptide by incubating at pH 2-3 for a short period of time. In some embodiments, to determine the binding affinity of a putative MHC-binding peptide for the same MHC allele, the stripped MHC monomer can be combined in solution with the putative MHC-binding peptide, beta2-microglobulin and a conformation-dependent monoclonal antibody. In some embodiments, the difference in fluorescence intensity determined between cells incubated with and without the test binding peptide after labeling, for example, either directly with the labeled monoclonal antibody or a fluorescence-labeled secondary antibody, can be used to determine binding of the test peptide.

In some embodiments, the binding affinity for an MHC (e.g. HLA) molecule is represented by an IC50, which is the concentration of peptide in a binding assay at which 50% inhibition of binding of a reference peptide is observed. In some cases, such assays can be run under conditions in which IC50 values approximate $K_D$ values (i. e., limiting HLA proteins and labeled peptide concentrations). In some embodiments, binding can be expressed relative to a reference peptide.

In some embodiments, the binding affinity can be predicted using in silico methods. Exemplary in silico methods for predicting binding affinity for MHC binding using algorithmic or other computational methods are known in the art, See, for example, Marsh, et al., *The HLA Factsbook* (Academic Press, 2000). In some embodiments, an algorithm can be used to predict if a peptide of interest should bind to a given MHC molecule. See, e.g., Southwood, et al., *J. Immunol.* 160:3363 (1998); Honeyman, et al., *Nat. Biotechnol.* 16:966-969 (1998); Breisie, et al., *Bioinformatics* 14:121-131 (1998), as well as the "SYFPEITHI" algorithm (Hans-Georg Rammensee, et al., *Immunogenetics* (1999) 50:213-219), Zhang et al., *PLOS ONE* 7 (2): e30483. doi: 10.1371/journal.pone.0030483, the Immune Epitope and Analysis Resource (IEDB) (Peters B, et al. *PLOS Biology* 3:379 (2005)), and the "BIMAS" algorithm (Parker, K. C., M. A. Bednarek, and J. E. Coligan. *J. Immunol.* 152:163 (1994).

In some embodiments, algorithm prediction tools, including those available from IEDB, use one or more predictions using ANN (Nielsen et al. (2003) *Protein Sci.,* 12:1007-1017 and Lundegaard et al. (2008) NAR, 36: W509-512), SMM (Peters and Sette (2005) *BMC Bioinformatics,* 6:132) and comblib (Sidney et al. (2008) *Immunome Res.* 4:2), or the Consensus tool (see Kim, et al. (2012) Immune epitope database analysis resource, NAR, combining predictions from any of the foregoing).

In some embodiments, prediction of antigen processing can be accomplished using an algorithm for proteasomal cleavage (PaProC). See Kuttler et al., *J. Mol. Biol.* 298 (2000), 417-429 and Nussbaum et al., *Immunogenetics* 53 (2001), 87-94.

In some embodiments, a chimeric receptor (e.g. a CAR), including a variant chimeric receptor (e.g. a variant CAR) can be assessed to determine if a detectable immune response to the molecule is induced following administration to a subject. In some embodiments, a subject can be treated with a chimeric receptor, such as a CAR, for example, by administering cells genetically engineered with the chimeric receptor or CAR. The presence of a humoral or cell-mediated human response can be assessed. In some embodiments, the presence of antibodies that specifically bind to and/or neutralize binding epitopes of the chimeric receptor (e.g. CAR) can be identified by methods such as ELISpot, intracellular cytokine staining, ELISAs (e.g. for cytokines), or cell-based antibody detection methods, for example, by flow cytometry, on serum from the subject. In some embodiments, a cell-mediated immune response to the chimeric receptor, such as a chimeric receptor expressed on engineered cells, can be assessed using a cytotoxic T-lymphocyte (CTL) assay for detection of CD8+ T cells that specifically bind to and induce cytotoxicity and/or a mixed lymphocyte reaction, using cells, e.g., irradiated cells, expressing the chimeric receptor, as stimulator cells.

In some embodiments, an immune response can be assessed in an in vitro assay by stimulating isolated immune cells (e.g. PBMCs) from a subject administered with a chimeric receptor (e.g. CAR) with a synthetic library of peptides which overlap and span the length of the particular antigen. The immune response in stimulated cells can be assessed using methods that include, but are not limited to, ELISpot, intracellular cytokine staining, cytotoxic T-lymphocyte assay's and/or mixed lymphocyte reactions. In some embodiments, T cell activation is measured via T cell proliferation (for example using 3H-thymidine incorporation) or cytokine production. Activation of TH1-type CD4+ T cells can, for example, may be detected via IFNγ production which may be detected by standard techniques, such as an ELISPOT assay.

In some embodiments, an enzyme-linked immunospot (ELISpot) assay can be employed to assess an immune response to a chimeric receptor. In some aspects, an ELISpot can be adapted for the detection of individual cells secreting specific cytokines or other effector molecules by attachment of a monoclonal antibody specific for a cytokine or effector molecule on a microplate. Cells stimulated by an antigen can be contacted with the immobilized antibody. After washing away cells and any unbound substances, a tagged polyclonal antibody or more often, a monoclonal antibody, specific for the same cytokine or other effector molecule can be added to the wells. Following a wash, a colorant that binds to the tagged antibody can be added such that a blue-black colored precipitate (or spot) forms at the sites of cytokine localization. The spots can be counted manually or with automated ELISpot reader system to quantitated the response.

In some embodiments, CD8+ T cell-mediated cytotoxic activity can be employed to assess an immune response to the chimeric receptor. In some embodiments, cells stimulated with an antigen (e.g. splenocytes) can be analyzed by chromium release assay for cytotoxicity against $^{51}$Cr-labeled cells. This assay can measure the release of (biological) radioactive chromium from cells as a result of killer cell activity. The cells can be re-stimulated with an antigen in vitro, for example, cells genetically engineered with a chimeric receptor (e.g. CAR-expressing cells), including T cells, peptide-loaded T cells and/or non-transduced ("Mock") T cells (targets) at various effector-to-target (E/T) ratios. Following co-incubation, release of chromium can be quantified and the percentage of maximum achievable lysis in each sample determined. Conditions in which no cytolytic activity specific is detected indicates that a specific immune responses to the chimeric receptor did not develop following co-administration with the tolerogenic peptide. This result may indicate a potential hit for administration of a specific peptide under conditions capable of inducing immunogenic tolerance to the chimeric receptor.

In some embodiments, intracellular cytokine staining is employed to assess an immune response to the chimeric receptor, such as in the presence or absence of co-administration with the tolerogenic peptide. Immune cells, such as splenocytes, can be isolated from the mice and stained with antibodies to detect CD8 and CD4 surface expression and intracellular expression of cytokine, including, for example, IFNγ. Conditions in which intracellular cytokine staining indicates T cells did not generate a specific immune response to the chimeric receptor may indicate a potential hit for administration of a specific peptide under conditions capable of inducing immunogenic tolerance to the chimeric receptor.

In some embodiments, clonal sequencing is employed to assess an immune response to the chimeric receptor. T cell receptors from T cells isolated from challenged mice or patients can be sequenced (see Arstila et al. (1999) Science 286, 958-961: WO 2012/083069). The absence of clonal TCR expansion indicates T cells did not generate a specific immune response to the chimeric receptor. This may indicate a potential hit for administration of a specific peptide under conditions capable of inducing immunogenic tolerance to the chimeric receptor.

In some embodiments, the variant chimeric receptor exhibits a reduced detectable immune response compared to the immune response generated to the reference chimeric receptor. In some embodiments, the immune response is a humoral immune response. In some embodiments, the immune response is a cell-mediated immune response. In some embodiments, the immune response is reduced greater than 1.2-fold, 1.5-fold, 2-fold, 3-fold, 4-fold, 5-fold, 6-fold, 7-fold, 8-fold, 9-fold, 10-fold, 50-fold, 100-fold or more.

In some embodiments, the variant chimeric receptor exhibits reduced immunogenicity compared to the reference chimeric receptor (e.g. unmodified or parent chimeric receptor) upon administration to a human subject, optionally wherein the subject has received administration of the reference chimeric receptor. In some embodiments, the reduced immunogenicity comprises a reduced CD4+ T cell immune response and/or a reduced CD8+ T cell immune response. In some embodiments, immunogenicity is reduced greater than 1.2-fold, 1.5-fold, 2-fold, 3-fold, 4-fold, 5-fold, 6-fold, 7-fold, 8-fold, 9-fold, 10-fold, 50-fold, 100-fold or more.

In some embodiments, the maximum number of variant chimeric receptor (e.g. CAR)-expressing cells, the area under the curve (AUC) for variant chimeric receptor-expressing cells over time, and/or the duration of detectable variant chimeric receptor-expressing cells in the subject following the administration of cells expressing the variant chimeric receptor is greater as compared to that achieved via a method comprising administration of cells expressing the reference chimeric receptor. In some embodiments, the method results in a maximum concentration or number of variant chimer receptor-expressing cells in the blood of the subject of at least at or about 10 chimeric-expressing cells per microliter, at least 50% of the total number of peripheral blood mononuclear cells (PBMCs), at least at least about $1 \times 10^5$ chimeric receptor-expressing cells, or at least 1,000, or at least 2,000, or at least 3,000, or at least 4,000, or at least 5,000 copies of CAR-encoding DNA per micrograms DNA.

In some embodiments, at day 30, at day 60, or at day 90 following the initiation of the administration of cells expressing the variant chimer receptor, variant chimeric receptor-expressing cells are detectable in the blood or serum of the subject.

In some embodiments, the variant chimeric receptor exhibits reduced immunogenicity as described while also retaining the biological activity or function, such as cytotoxic activity, as compared to the reference chimeric receptor (unmodified or parent chimeric receptor not containing the amino acid replacement(s)). In some embodiments, the biologic activity, such as cytotoxic activity, is present in an antigen-specific manner. In some embodiments, the biological or functional activity, such as cytotoxic activity, of the variant chimeric receptor is at least 40%, 50%, 60%, 70%, such as typically at least 75%, 80%, 85%, 90%, 95% of the biological activity or functional activity (e.g. cytotoxic activity) of the unmodified or parent chimeric receptor not containing the amino acid replacement(s).

In some embodiments, biological activity or functional activity of a chimeric receptor, such as cytotoxic activity, can be measured using any of a number of known methods. The activity can be assessed or determined either in vitro or in vivo. In some embodiments, activity can be assessed once the cells are administered to the subject (e.g., human). Parameters to assess include specific binding of an engineered or natural T cell or other immune cell to antigen, e.g., in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

III. Nucleic Acids, Vectors and Engineered Cells

Provided are methods, nucleic acids, compositions, and kits for producing the genetically engineered cells. The genetic engineering generally involves introduction of a nucleic acid encoding the chimeric receptor into a composition containing the cultured cells, such as by retroviral transduction, transfection, or transformation.

In some embodiments, the nucleic acid molecule encodes the recombinant receptors, e.g., chimeric receptor, such as any described above. Also provided are vectors or constructs containing such nucleic acid molecules. In some embodiments, the vectors or constructs contain one or more promoters operatively linked to the nucleotide encoding the receptor to drive expression thereof. In some embodiments, the promoter is operatively linked to one or more than one nucleic acid molecule.

In some embodiments, the vector or construct can contain a single promoter that drives the expression of one or more nucleic acid molecules. In some embodiments, such promoters can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding a first and second chimeric receptor) by a message from a single promoter. Alternatively, in some cases, a single promoter may direct expression of an RNA that contains, in a single open reading frame (ORF), two or three genes (e.g. encoding a first and second chimeric receptor) separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream. Examples of 2A cleavage peptides, including those that can induce ribosome skipping, are T2A, P2A, E2A and F2A.

Also provided are cells such as cells that contain an engineered chimeric receptor, such as described herein. Also provided are populations of such cells, compositions containing such cells and/or enriched for such cells, such as in which cells expressing the chimeric receptor make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the chimeric receptors e.g., cells containing the CARs. The cells generally are eukaryotic cells, such as mammalian cells, and typically are human cells. In some embodiments, the cells are derived from the blood, bone marrow; lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg)

cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Preparation of Cells for Engineering

In some embodiments, preparation of the engineered cells includes one or more culture and/or preparation steps. The cells for introduction of the chimeric receptor, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS®; M-450) CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82: Wang et al. (2012) *J Immunother.* 35 (9): 689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127: in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher (Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained: for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered: in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35 (9): 651-660, Terakura et al. (2012) Blood. 1:72-82, and Wang et al. (2012) *J Immunother.* 35 (9): 689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1 (5): 355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35 (9): 651-660, Terakura et al. (2012) Blood. 1:72-82, and/or Wang et al. (2012) J Immunother. 35 (9): 689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

Vectors and Methods for Genetic Engineering

Various methods for the introduction of genetically engineered components, e.g., antigen receptors, e.g., CARs or TCRs, are well known and may be used with the provided methods and compositions. Exemplary methods include those for transfer of nucleic acids encoding the receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity: the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990: Miller, A. D. (1990) Human Gene Therapy 1:5-14: Scarpa et al. (1991) Virology 180:849-852: Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35 (9): 689-701: Cooper et al. (2003) Blood. 101: 1637-1644: Verhoeven et al. (2009) Methods Mol Biol. 506:97-114; and Cavalieri et al. (2003) Blood. 102 (2): 497-505.

In some embodiments, recombinant nucleic acids are transferred into T cells via electroporation (see, e.g., Chicaybam et al, (2013) PLOS ONE 8 (3): e60298 and Van Tedeloo et al. (2000) Gene Therapy 7 (16): 1431-1437). In some embodiments, recombinant nucleic acids are transferred into T cells via transposition (see, e.g., Manuri et al. (2010) Hum Gene Ther 21 (4): 427-437; Sharma et al. (2013) Molec Ther Nucl Acids 2, e74; and Huang et al. (2009) Methods Mol Biol 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection: tungsten particle-facilitated microparticle bombardment (Johnston, Nature, 346:776-777 (1990)); and strontium phosphate DNA co-precipitation (Brash et al., Mol. Cell Biol., 7:2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012:907:645-66 or Barrett et al., Chimeric Antigen Receptor Therapy for Cancer Annual Review of Medicine Vol. 65:333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization: genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

IV. Compositions, Formulations and Methods of Administration

Also provided are compositions containing the chimeric receptor, such as CAR, and compositions containing the engineered cells, including pharmaceutical compositions and formulations. Also provided are methods of using and uses of the compositions, such as in the treatment of diseases, conditions, and disorders in which the antigen is expressed, or in detection, diagnostic, and prognostic methods.

1. Compositions Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10) residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins: 21st ed. (May 1, 2005).

The formulation or composition may also contain more than one active ingredients useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

2. Methods of Administration

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, provided cells and compositions are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al: U.S. Pat. No. 4,690,915 to Rosenberg; Rosenberg (2011) Nat Rev Clin Oncol. 8 (10): 577-85). See, e.g., Themeli et al. (2013) *Nat Biotechnol.* 31 (10): 928-933; Tsukahara et al. (2013) *Biochem Biophys Res Commun* 438 (1): 84-9; Davila et al. (2013) *PLOS ONE* 8 (4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super type as the first subject. The cells can be administered by any suitable means. Dosing and administration may depend in part on whether the administration is brief or chronic. Various dosing schedules include but are not limited to single or multiple administrations over various time-points, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo. e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3:1 1 1 (1995), and U.S. Pat. No. 5,087,616.

V. Exemplary Embodiments

Among the provided embodiments are:

1. A variant chimeric receptor, comprising a modified junction region having one or more amino acid sequence modifications compared to a junction region of a reference chimeric receptor, wherein:
the reference chimeric receptor comprises a first domain and a second domain, joined in contiguous sequence at a junction, wherein the junction region of the reference chimeric receptor comprises up to 15 contiguous amino acids directly C-terminal of the junction and/or up to 15 contiguous amino acids directly N-terminal of the junction; and
a peptide fragment having the sequence of an 8-15 amino acid portion of the modified junction region has a binding affinity for a human leukocyte antigen (HLA) molecule that is lower than the binding affinity, for the same HLA molecule, of a peptide fragment having the sequence of the corresponding portion of the junction region of the reference chimeric receptor.

2. The variant chimeric receptor of embodiment 1, wherein the peptide fragment of the corresponding portion of the junction region of the reference chimeric receptor has a binding affinity of less than 1000 nM, less than 500 nM or less than 50 nM.

3. A variant chimeric receptor, comprising a modified junction region having one or more amino acid sequence modifications compared to a junction region of a reference chimeric receptor, wherein:
the reference chimeric receptor comprises a first domain and a second domain, joined in contiguous sequence at a junction, wherein the junction region of the reference chimeric receptor comprises up to 15 contiguous amino acids directly C-terminal of the junction and/or up to 15 contiguous amino acids directly N-terminal of the junction; and
the average of the binding affinities of all 8-15 amino acid fragments, or of all 8, 9, 10, 11, 12, 13, 14, or 15 amino acid fragments, within the modified junction region for a human HLA molecule is lower than the average of the binding affinities of all 8-15 amino acid fragments, or of all 8, 9, 10, 11, 12, 13, 14, or 15 amino acid fragments, within the junction region of the reference chimeric receptor.

4. The variant chimeric receptor of any of embodiments 1-3, wherein the binding affinity or average of binding affinities is more than 2-fold, more than 5-fold, more than 10-fold, more than 25-fold, more than 50-fold or more than 100-fold lower.

5. A variant chimeric receptor, comprising a modified junction region having one or more amino acid sequence modifications compared to a junction region of a reference chimeric receptor, wherein:
the reference chimeric receptor comprises a first domain directly linked to a second domain joined in contiguous sequence at a junction, wherein;
the junction region of the reference chimeric receptor comprises up to 15 contiguous amino acids directly C-terminal of the junction and/or up to 15 contiguous amino acids directly N-terminal of the junction; and
the number of peptide fragments having the sequence of an 8-15 amino acid portion of the modified junction region that has a binding affinity for a human leukocyte antigen (HLA) of less than 1000 nM is reduced compared to the number of peptide fragments having the sequence of an 8-15 amino acid portion of the junction region of the reference chimeric receptor that has the same affinity for binding the same HLA.

6. The variant chimeric receptor of embodiment 5, wherein:
the number of peptide fragments within the modified junction region that exhibits a binding affinity for an HLA of less than 500 nM or less than 50 nM is reduced; or
the binding affinity of less than 1000 nM is a binding affinity of less than 500 nM or less than 50 nm.

7. The variant chimeric receptor of any of embodiments 1-6, wherein the binding affinity is an IC50 and the comparison of binding of peptide fragments of the modified junction regions and the peptide fragments of the junction region of the reference chimeric receptor is with reference to the same standard peptide.

8. The variant chimeric receptor of any of embodiments 1-7, wherein:
the first domain and/or second domain comprises a domain of a natural human protein; and/or
the first domain and/or second domain comprises an extracellular binding domain, a hinge domain, a transmembrane domain, or an intracellular signaling domain, which intracellular signaling domain is, optionally, a costimulatory signaling domain or an activating cytoplasmic signaling domain.

9. The variant chimeric receptor of any of embodiments 1-8, wherein the first domain and second domain are not present in the same molecule in vivo in a human subject.

10. The variant chimeric receptor of any of embodiments 1-9, wherein the first domain and second domain are, respectively, an extracellular ligand binding domain and a hinge domain, a hinge domain and a transmembrane domain, a transmembrane domain and an intracellular costimulatory signaling domain, and an intracellular costimulatory signaling domain and an activating cytoplasmic signaling domain, which can include functional portions of such domains.

11. The variant chimeric receptor of any of embodiments 1-10, wherein the first domain is a transmembrane domain or a functional portion thereof and the second domain is a costimulatory signaling domain or a functional portion thereof.

12. The variant chimeric receptor of embodiment 11, wherein the transmembrane domain is a CD28 transmembrane domain or a functional portion or variant thereof and the costimulatory signaling domain is a 4-1BB signaling domain or a functional portion or variant thereof.

13. The variant chimeric receptor of any of embodiments 1-12, wherein the junction region of the reference chimeric receptor comprises up to 13 contiguous amino acids directly C-terminal of the junction and/or up to 15 contiguous amino acids directly N-terminal of the junction.

14. The variant chimeric receptor of any of embodiments 1-13, wherein the peptide fragment(s) comprises a sequence of amino acids between or between about 8 and 15 amino acids in length, or comprises a sequence of amino acids that is at least or at least about or is or is about 8, 9, 10, 11, 12, 13, 14 or 15 amino acids in length.

15. The variant chimeric receptor of any of embodiments 1-14, comprising:
a domain of at least 95% sequence identity to the first domain and/or a domain of at least 95% sequence identity to the second domain;
a domain identical in sequence to the first domain and a domain of at least 95% sequence identity to the second domain; or
a domain of at least 95% sequence identity to the first domain and a domain identical in sequence to the second domain,
wherein at least one or both of the domains present in the variant chimeric receptor is modified compared to the first domain and/or second domain of the reference chimeric receptor in the portion comprising the modified junction region.

16. The variant chimeric receptor of any of embodiments 1-15, wherein:
the variant chimeric receptor comprises at least 85%, 86%, 87%, 88%, 89%, 90%, 91%, 92%, 93%, 94%, 95%, 96%, 97%, 98%, 99% or more sequence identity to the reference chimeric receptor; and/or
the variant chimeric receptor comprises up to 1, 2, 3, 4, 5, 6, 7, 8, 9, 10, 11, 12, 13, 14, 15, 16, 17, 18, 19 or 20 amino acid modifications compared to the reference chimeric receptor.

17. The variant chimeric receptor of any of embodiments 12-16, wherein
the CD28 transmembrane domain comprises the sequence of amino acids set forth in SEQ ID NO:2, 103 or 104 or a functional portion or variant thereof comprising a sequence that exhibits at least 95% sequence identity to SEQ ID NO:2, 103 or 104; and
the 4-1BB costimulatory signaling domain comprises the sequence of amino acids set forth in SEQ ID NO:3 or a functional portion or variant thereof comprising a sequence that exhibits at least 95% sequence identity to SEQ ID NO:3.

18. The variant chimeric receptor of any of embodiments 12-17, wherein the first domain and second domain together comprise the sequence of amino acids set forth in SEQ ID NO: 5 or a functional portion or variant thereof comprising a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:5.

19. The variant chimeric receptor of any of embodiments 12-18, wherein the first domain and second domain together comprise the sequence of amino acids set forth in SEQ ID NO: 5.

20. The variant chimeric receptor of any of embodiments 12-19, wherein the one or more modifications are within a portion between residue 13 and 42 or between amino acid residue 15 and 40, with reference to numbering set forth in SEQ ID NO:5.

21. The variant chimeric receptor of any of embodiments 1-20, wherein the one or more modifications comprises an amino acid insertion, replacement or deletion and/or wherein each of the one or more modifications individually comprises an amino acid insertion, replacement, or deletion.

22. The variant chimeric receptor of any of embodiments 1-21, wherein the first and/or second domain comprises a transmembrane domain, wherein
the one or more modifications is not or does not comprise a modification at or of a hydrophobic amino acid residue or within a hydrophobic portion in the transmembrane domain, which optionally is the CD28 transmembrane domain; or
the one or more modifications comprises a modification of a hydrophobic amino acid residue within the transmembrane domain, which optionally is the CD28 transmembrane domain, wherein the modification is or comprises a substitution of the hydrophobic amino acid with another different hydrophobic amino acid residue; or
the one or more modifications is not or does not comprise a modification at or of a hydrophobic amino acid residue or within a hydrophobic portion in the transmembrane domain, which optionally is the CD28 transmembrane domain, other than a substitution with another hydrophobic amino acid residue.

23. The variant chimeric receptor of any of embodiments 12-22, wherein the one or more modifications comprise a modification at an amino acid residue corresponding to an amino acid residue between residues 28 and 42 with reference to numbering set forth in SEQ ID NO:5.

24. The variant chimeric receptor of any of embodiments 1-23, wherein the amino acid modification is an insertion and the variant chimeric receptor comprises an insertion between amino acid residues adjacent to the junction between the domains, which optionally corresponds to amino acid residues 27 and 28 with reference to numbering set forth SEQ ID NO: 5.

25. The variant chimeric receptor of embodiment 24, comprising insertion of 1, 2, 3, 4 or 5 amino acid residues.

26. The variant chimeric receptor of embodiment 24 or embodiment 25, wherein the insertion is of any amino acid residue, which, optionally, is asparagine (N).

27. The variant chimeric receptor of any of embodiments 12-26, wherein the one or more modifications comprises an amino acid replacement(s) and the amino acid replacement(s) are at one or more residues corresponding to a residue selected from 28, 31 or 34 with reference to numbering set forth in SEQ ID NO:5.

28. The variant chimeric receptor of embodiment 27, wherein the amino acid replacement(s) is to any other amino acid residue, which, optionally, is selected from among leucine (L), asparagine (N), glutamine (Q), alanine (A), serine(S) or histidine (H).

29. The variant chimeric receptor of embodiment 27 or embodiment 28, wherein the amino acid replacement(s) corresponds to or is a replacement selected from among K28A, K28H, K28L, K28Q, K28S, R31A, R31H, R31L, R31N, R31S, L34A and L34S, with reference to numbering set forth in SEQ ID NO:5.

30. The variant chimeric receptor of any of embodiments 27-29, wherein the amino acid replacement does not comprise the single amino acid replacement corresponding to L34A or L34S, with reference to numbering set forth in SEQ ID NO:5.

31. The variant chimeric receptor of any of embodiments 27-30, wherein the amino acid replacements are or correspond to amino acid replacements selected from among K28Q/R31A, K28Q/R31N, K28Q/R31S, K28Q/L34A, K28Q/L34S, R31N/L34A, R31N/L34S, K28Q/R31N/L34A, K28Q/R31N/L34S.

32. The variant chimeric receptor of any of embodiments 1-31, wherein:
the variant chimeric receptor comprises a modified junction region comprising less than 100% sequence identity to SEQ ID NO: 137 but greater than 85%, 86%, 87%, 88%, 89%, 90%, 91%, 92%, 93%, 94%, 95% or 96% to SEQ ID NO: 137 and comprises the modifications; and/or
the variant chimeric receptor comprises a sequence comprising less than 100% sequence identity to SEQ ID NO:5 but greater than 85%, 86%, 87%, 88%, 89%, 90%, 91%, 92%, 93%, 94%, 95% or 96% to SEQ ID NO:5 and comprises the modifications.

33. The variant chimeric receptor of any of embodiments 1-32, wherein the variant chimeric receptor comprises a modified junction region selected from among:
   i) the sequence of amino acids set forth in any of SEQ ID NOS: 138-157 and 184;
   ii) a functional variant thereof comprising a sequence of amino acids that exhibits at least 95% sequence identity to the sequence of amino acids set forth in any of SEQ ID NOS: 138-157 and 184 and that comprise the modification(s); or
   iii) a functional portion of i) or ii) and comprises the modification(s).

34. The variant chimeric receptor of any of embodiments 1-33, wherein the variant chimeric receptor comprises:
   i) the sequence of amino acids set forth in any of SEQ ID NOS: 114-134 and 183;
   ii) a functional variant thereof comprising a sequence of amino acids that exhibits at least 95% sequence identity to the sequence of amino acids set forth in any of SEQ ID NOS: 114-134 and 183 and that comprise the modification(s);
   ii) or is a functional portion of i) or ii) and comprises the modification(s).

35. The variant chimeric receptor of any of embodiments 1-34, wherein the modified junction region comprises no more than 1, 2, 3, 4, 5, 6, 7, 8, 9 or 10 amino acid modifications compared to the junction region of the reference chimeric receptor.

36. The variant chimeric receptor of any of embodiments 1-35, wherein the first domain or second domain is a transmembrane domain and the corresponding domain in the variant chimeric receptor comprises a substantially hydrophobic hydropathy profile and/or comprises a grand average of hydropathy (GRAVY) value of greater than 0, 0.25, 0.5, 0.75, 1, 1.1, 1.2, 1.3, 1.4, 1.5, 1.6, 1.7, 1.8, 1.9, 2.0, 2.1, 2.2 or greater.

37. The variant chimeric receptor of any of embodiments 1-36, wherein first domain or second domain comprises an intracellular signaling domain and the corresponding domain in the variant chimeric receptor is capable of inducing the activation or cellular localization of a TRAF and/or is capable of inducing TRAF-mediated signaling.

38. The variant chimeric receptor of embodiment 37, wherein the intracellular signaling domain is a 4-1BB costimulatory signaling domain and/or the TRAF is selected from among TRAF1, TRAF2 or TRAF3.

39. The variant chimeric receptor of any of embodiments 12-38, wherein the variant chimeric receptor comprises amino acids TTQE at positions corresponding to 49-52 and/or amino acids PEEE at positions corresponding to residues 60-63, each with reference to numbering set forth in SEQ ID NO:5.

40. The variant chimeric receptor of any of embodiments 1-39, wherein the HLA is an HLA class I and/or an HLA class II.

41. The variant chimeric receptor of any of embodiments 1-40, wherein the HLA class I is selected from an HLA allele set forth in Table 1A and/or the HLA class II allele is selected from an HLA allele set forth in Table 1B.

42. The variant chimeric receptor of any of embodiments 1-41, wherein the HLA class I allele is selected from among HLA-A*02:01, HLA-A*03:01, HLA-A*11:01 and HLA-B*08:01.

43. The variant chimeric receptor of any of embodiments 3-42, wherein the HLA comprises a plurality of HLA molecules and average binding affinities to one or more of the plurality of HLA molecules is lower and/or the number of peptide fragments that individually bind to one or more of the plurality of HLA molecules is reduced.

44. The variant chimeric receptor of embodiment 43, wherein the plurality of HLA molecules is selected from:
   a plurality of HLA class I molecules that represent greater than 50%, greater than 60%, greater than 70%, greater than 80%, greater than 90%, greater than 95% or greater than 99% of the HLA class I molecules in the worldwide population or in the Caucasian population;
   a plurality of HLA class II molecules that represent greater than 50%, greater than 60%, greater than 70%, greater than 80%, greater than 90%, greater than 95% or greater than 99% of the HLA class II molecules in the worldwide population or in the Caucasian population; or
   a plurality of HLA class I molecules and HLA class II molecules that represent greater than 50%, greater than 60%, greater than 70%, greater than 80%, greater than 90%, greater than 95% or greater than 99% of the HLA class I molecules and HLA class II molecules in the worldwide population or in the Caucasian population;

45. The variant chimeric receptor of any of embodiments 1-44, wherein the binding affinity is as determined in vitro.

46. The variant chimeric receptor of any of embodiments 1-45 that exhibits reduced immunogenicity compared to the reference chimeric receptor upon administration to a human subject, optionally wherein the subject has received administration of the reference chimeric receptor.

47. The variant chimeric receptor of embodiment 46, wherein the reduced immunogenicity comprises a reduced CD4+ T cell immune response and/or a reduced CD8+ T cell immune response.

48. The variant chimeric receptor of any of embodiments 11-47, wherein:
   the reference chimeric receptor further comprises an extracellular ligand-binding domain; and/or
   the variant chimeric receptor further comprises an extracellular ligand-binding domain.

49. The variant chimeric receptor of embodiment 48 that is a chimeric antigen receptor (CAR), wherein the ligand-binding domain is an antigen-binding domain.

50. The variant chimeric receptor of embodiment 49, wherein the antigen-binding domain is an antibody or an antibody fragment.

51. The variant chimeric receptor of embodiment 50, wherein the antigen-binding domain is an antibody fragment that is a single chain fragment.

52. The variant chimeric receptor of embodiment 50 or embodiment 51, wherein the fragment comprises antibody variable regions joined by a flexible immunoglobulin linker.

53. The variant chimeric receptor of any of embodiments 50-52, wherein the antibody fragment comprises an scFv.

54. The variant chimeric receptor of any of embodiments 48-52, wherein the ligand-binding domain specifically binds an antigen that is associated with a disease or disorder.

55. The variant chimeric receptor of embodiment 54, wherein:
   the disease or disorder is an infectious disease or condition, an autoimmune disease, an inflammatory disease or a tumor or a cancer;
   the ligand-binding domain specifically binds to a tumor antigen; and/or the ligand-binding domain specifically binds to an antigen selected from the group consisting of ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1) and cyclin A1 (CCNA1).

56. The variant chimeric receptor of any of embodiments 11-55, wherein:
the reference chimeric receptor further comprises an activating cytoplasmic signaling domain; and/or
the variant chimeric receptor further comprises an activating cytoplasmic domain.

57. The variant chimeric receptor of embodiment 56, wherein the activating cytoplasmic domain comprises a T cell receptor (TCR) component and/or comprise an immunoreceptor tyrosine-based activation motif (ITAM).

58. The variant chimeric receptor of embodiment 56 or embodiment 57, wherein the activating cytoplasmic signaling domain is or comprises a cytoplasmic signaling domain of a zeta chain of a CD3-zeta (CD3ζ) chain or a functional variant or signaling portion thereof.

59. The variant chimeric receptor of any of embodiments 11-58, wherein:
the reference chimeric receptor comprises form its N to C terminus in order: an extracellular ligand-binding domain, the first domain that is a transmembrane domain, the second domain that is an intracellular costimulatory domain and an activating cytoplasmic signaling domain; and/or
the variant chimeric receptor comprises from its N to C terminus in order: an extracellular ligand-binding domain, a transmembrane domain, a intracellular costimulatory domain and an activating cytoplasmic signaling domain, wherein the transmembrane domain and intracellular costimulatory domain are joined in contiguous sequence at a junction to form the modified junction region.

60. A nucleic acid molecule encoding the variant chimeric receptor of any of embodiments 1-59.

61. A vector, comprising the nucleic acid molecule of embodiment 60.

62. The vector of embodiment 61 that is a viral vector.

63. The vector of embodiment 61 or embodiment 62 that is a retroviral vector, which optionally is a lentiviral vector or a gammaretroviral vector.

64. An engineered cell, comprising the nucleic acid of embodiment 60 or the vector of any of embodiments 61-63 or expressing the chimeric receptor of any of embodiments 1-59.

65. The engineered cell of embodiment 64, which is a T cell.

66. The engineered cell of embodiment 64 or embodiment 65 that is a CD4+ T cell and/or a CD8+ T cell.

67. A composition, comprising the engineered cells of any of embodiments 64-66, and optionally a pharmaceutically acceptable buffer.

68. A method of treatment, comprising administering the cell of any of embodiments 64-66 or the composition of embodiment 67 to a subject having a disease or condition.

69. The method of embodiment 68, wherein the chimeric receptor specifically binds to a ligand or antigen associated with the disease or condition.

70. The method of embodiment 68 or embodiment 69, wherein the disease or condition is a cancer, a tumor, an autoimmune disease or disorder, or an infectious disease.

71. The method of any of embodiments 68-70, wherein the genetically engineered T cells in the composition exhibit increased or longer expansion and/or persistence in the subject than in a subject administered the same or about the same dosage amount of a reference cell composition expressing the reference chimeric receptor.

72. The method of embodiment 71, wherein the increase is at least 1.2-fold, 1.5-fold, 2-fold, 3-fold, 4-fold, or 5-fold.

73. The method of embodiment 71 or embodiment 72, wherein the increase is observed or is present within a month, within two months, within six months or within one year of administering the cells.

VI. Definitions

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) sequence identity" and "percent identity" when used with respect to a nucleotide sequence (reference nucleotide sequence) is defined as the percentage of nucleotide residues in a candidate sequence (e.g., the subject chimeric receptor, such as a variant chimeric receptor) that are identical with the nucleotide residues in the reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, "corresponding" with reference to a position of a region, such as "at a position corresponding to" or recitation that a region or amino acid positions "correspond to" a region or amino acid positions in a disclosed sequence, such as set forth in the Sequence listing, refers to amino acid positions identified upon alignment with the disclosed sequence to maximize identity using a standard alignment algorithm, such as the GAP algorithm. Exemplary described corresponding residues can be identified by alignment of a sequence with an exemplary reference junction region sequence set forth in SEQ ID NO:5. By aligning the sequences, one skilled in the art can identify corresponding residues or regions, for example, using conserved and identical amino acid residues as guides. In general, to identify corresponding positions or regions, the sequences of amino acids are aligned so that the highest order match is obtained (see, e.g.: Computational Molecular Biology, Lesk, A. M., ed., Oxford University Press, New York, 1988: Biocomputing: Informatics and Genome Projects, Smith, D. W., ed., Academic Press, New York, 1993: Computer Analysis of Sequence Data, Part I, Griffin, A. M., and Griffin, H. G., eds., Humana Press, New Jersey, 1994: Sequence Analysis in Molecular Biology, von Heinje, G., Academic Press, 1987; and Sequence Analysis Primer, Gribskov, M. and Devereux, J., eds., M Stockton Press, New York, 1991: Carrillo et al. (1988) SIAM J Applied Math 48:1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

VII. Examples

The following examples are included for illustrative purposes only and are not intended to limit the scope of the invention.

Example 1: Analysis of Transgene Product-Specific Host Immune Responses

Pre- and post-treatment peripheral blood mononuclear cells (PBMC) samples were obtained from four (4) subjects with B cell malignancies treated with autologous T cells expressing a CD19-specific CAR. The CAR included an anti-CD19 scFv derived from murine antibody, a hinge domain, a CD28 transmembrane domain, a 4-1BB intracellular signaling domain, and a CD3-zeta intracellular signaling domain. The CAR-expressing T cells also expressed a truncated EGFR (EGFRt) as a surrogate marker by transducing cells with a lentiviral vector containing a nucleic acid encoding the CAR and a nucleic acid encoding the EGFRt surrogate marker, separated by a T2A ribosome switch domain.

Pre- and post (day 42)-infusion PBMCs obtained from the subjects were assessed to detect the presence or absence of specific anti-CAR immune responses essentially as described by Berger et al. *Blood.* 2006 March; 107 (6): 2294-2302, Berger et al. *J Virol.* 2001 January 75 (2): 799-808, Riddell et al. *Nature Medicine.* 1996 Feb. 2 (2): 216-223, Berger et al. *Blood.* 2005 February 105 (4): 1640-1647. Briefly, PBMCs (responders) were stimulated in vitro with autologous gamma-irradiated cells transduced with the CAR expressed by the administered cells (stimulators at a 1:1 or 2:1 responder-to-stimulator ratio). The cultures then were assessed in a chromium release assay for cytotoxicity against autologous $^{51}$Cr-labeled CAR-transduced ("CD19 CAR") and non-transduced ("Mock") T cells (targets) at various effector-to-target (E/T) ratios. Following co-incubation, release of chromium was quantified and the percentage of maximum achievable lysis in each sample determined.

The results for samples derived from one exemplary patient are shown in FIG. 1, which depicts the cytolytic activity of PBMCs pre-infusion and post-infusion at day 42. Whereas no cytolytic activity specific for CAR-transduced target cells was detected in any pre-infusion PBMC-derived cultures, in two of the four subjects assessed, CAR-specific lytic activity was detected in cultures derived from post-infusion PBMC samples. These results indicate that CAR-specific immune responses can develop following a single infusion of CAR-expressing T cells.

Epitope mapping was carried out to assess region(s) of the CAR recognized by the specific immune responses. Pre- and post-infusion PBMC samples were stimulated in the presence of individual pools of multiple 15-mer peptides, with sequences representing overlapping portions (11 amino acid overlap) of the entire length of an approximately 500 amino acid sequence of the CAR expressed by the administered cells. Cells were stained with antibodies to detect CD8 and CD4 surface expression and intracellular expression of cytokine. Twenty-three (23) pools were assessed, each containing ten (10) peptides each and collectively including 125 individual overlapping peptides, with each peptide represented in at least two of the pools.

This design permitted the generation of an analytic grid to assess responses specific for individual peptides, whereby a peptide present in more than one pool detected as hits in this assay was deemed a potentially immunogenic peptide hit. For the two patients in whom a CAR-specific immune response had been detected, six and three peptide hits, respectively, were identified.

Figure 2:
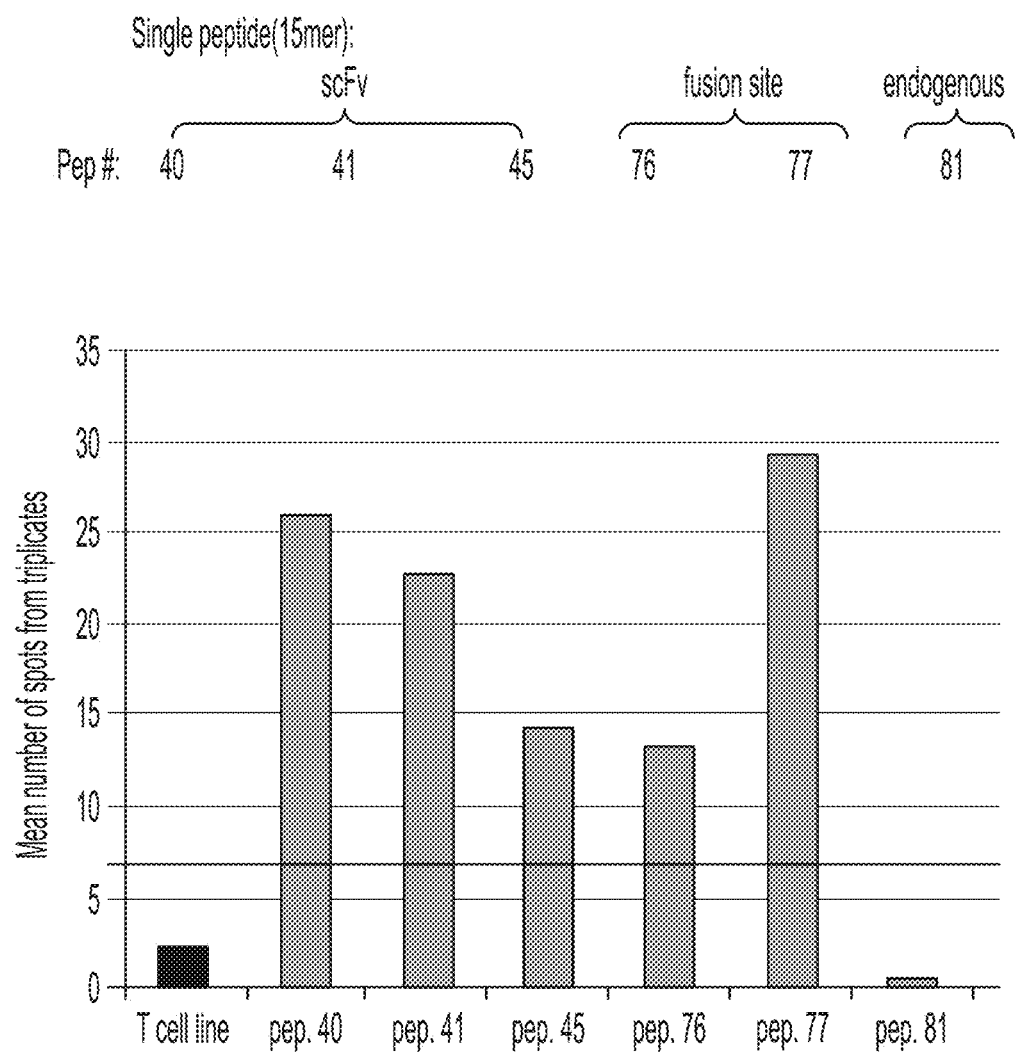
FIG. 2 shows results from an exemplary ELISpot analysis confirming immune responses to certain overlapping peptides representing particular regions of a CAR in an exemplary human subject. Numbers labeled with "pep" represent various overlapping peptides along the length of the CAR sequence, with corresponding regions indicated above the chart.

Individual ELISpot assays were performed using an anti-cytokine capture antibody to assess the presence or absence of a specific immune response for each of these individual hits (see Berger et al. (2006); Berger et al. (2001); Riddell et al. (1996); and Berger et al. (2005), supra). The results of an exemplary assay for one patient are shown in FIG. 2. Specific immune responses against peptides with sequences within the $V_H$ portion of the scFv of the CAR were detected in both patients assessed (including regions within the FR1, CDR1, and FR2 regions for one patient and within the FR3 for the other). For the first patient, specific immune responses also were detected against two overlapping 15-mer peptides, each containing the junction between the transmembrane domain and costimulatory domain of the CAR (labeled "fusion site" in FIG. 2). These two overlapping 15-mer peptides had the amino acid sequences AFIIFWVKRGRKKLL (SEQ ID NO: 8) and FWVKR-GRKKLLYIFK (SEQ ID NO: 9), respectively. In another study following administration with a different CAR having a murine scFv, CD28 transmembrane and costimulatory domains and a CD3 zeta domain, using similar methods, an immune response also was detected for one subject against a pool containing $V_H$ portions of an anti-CD19 scFv and for another subject in a pool containing junction portions.

No specific immune responses were detected in the patients by this assay against peptides within other regions. For example, in this assay, no specific responses were detected against peptides having sequences within other CDRs or framework regions of the scFv, peptides within regions of costimulatory or transmembrane domain but not spanning the junction between the two, or peptides within the EGFRt or CD3-region of the CAR. Specific immune responses were not detected against endogenous sequences.

Example 2: In Silico Analysis of Peptides Derived from Junction Regions of a CAR for Binding to HLA Class I and HLA Class II T cell epitope prediction tools, available from the Immune Epitope Database and analysis resource (IEDB), were used for in silico analysis to predict MHC-binding affinities and other properties related to potential immunogenicity for each of a series of overlapping peptide sequences within a portion of an exemplary CAR sequence. The portion included a spacer having an immunoglobulin-derived hinge domain, a human CD28 transmembrane domain, a human 4-1BB costimulatory domain, and a human CD3zeta signaling domain. In the portion assessed, the hinge domain was a human IgG4 hinge domain, the CD28 transmembrane domain comprised a sequence set forth in SEQ ID NO:2 and the 4-1BB costimulatory domain contained the sequence set forth in SEQ ID NO:3. This portion thus contained three junctions between different domains derived from human sequences (which junctions may have represented sites of potential immunogenicity against a CAR upon administration to a human subject): the junction between the spacer region and transmembrane domain, the junction between the transmembrane domain and costimulatory domain, and the junction between the costimulatory domain and intracellular signaling domain (see FIGS. 3A and 3B).

To identify portions of the sequence that may have particular properties making them more likely to be presented to T cells, affinities for binding to 27 individual HLA class I alleles and 56 individual HLA class II alleles were predicted for overlapping peptides along the length of the portion, of 8-14 amino acids in length and of 15 amino acids in length (containing 9-mer binding core), respectively. These alleles, collectively representing HLA alleles present in greater than 99% of the worldwide population, and their approximate frequency in the United States population are listed in Tables 1A and 1B.

TABLE 1A

| | HLA class I | |
|---|---|---|
| Class I | allele | Frequency in population |
| 1 | HLA-A*01:01 | 12.94 |
| 2 | HLA-A*02:01 | 42.88 |
| 3 | HLA-A*02:03 | 0.19 |
| 4 | HLA-A*02:06 | 1.55 |
| 5 | HLA-A*03:01 | 13.50 |
| 6 | HLA-A*11:01 | 11.60 |
| 7 | HLA-A*23:01 | 8.30 |
| 8 | HLA-A*24:02 | 22.56 |
| 9 | HLA-A*26:01 | 5.36 |
| 10 | HLA-A*30:01 | 6.29 |
| 11 | HLA-A*30:02 | 5.21 |
| 12 | HLA-A*31:01 | 6.87 |
| 13 | HLA-A*32:01 | 3.71 |
| 14 | HLA-A*33:01 | 2.62 |
| 15 | HLA-A*68:01 | 6.36 |
| 16 | HLA-A*68:02 | 4.79 |
| 17 | HLA-B*07:02 | 12.96 |
| 18 | HLA-B*08:01 | 9.23 |
| 19 | HLA-B*15:01 | 6.54 |
| 20 | HLA-B*35:01 | 13.03 |
| 21 | HLA-B*40:01 | 9.79 |
| 22 | HLA-B*44:02 | 7.22 |
| 23 | HLA-B*44:03 | 8.96 |
| 24 | HLA-B*51:01 | 8.51 |
| 25 | HLA-B*53:01 | 7.26 |
| 26 | HLA-B*57:01 | 3.49 |
| 27 | HLA-B*58:01 | 4.82 |

TABLE 1B

| | HLA class II | |
|---|---|---|
| Class II | allele | Frequency in population |
| 1 | HLA-DRB1*01:01 | 13.62 |
| 2 | HLA-DRB1*15:01 | 22.86 |
| 3 | HLA-DRB1*03:01 | 21.82 |
| 4 | HLA-DRB1*04:01 | 15.54 |
| 5 | HLA-DRB1*11:01 | 10.92 |
| 6 | HLA-DRB1*13:01 | 9.86 |
| 7 | HLA-DRB1*07:01 | 19.84 |
| 8 | HLA-DRB1*01:01 | 4.06 |
| 9 | HLA-DRB1*01:02 | 1.85 |
| 10 | HLA-DRB1*04:02 | 6.28 |
| 11 | HLA-DRB1*04:05 | 1.22 |
| 12 | HLA-DRB1*04:07 | 2.78 |
| 13 | HLA-DRB1*04:08 | 1.26 |
| 14 | HLA-DRB1*08:04 | 0.86 |
| 15 | HLA-DRB1*09:01 | 5.33 |
| 16 | HLA-DRB1*10:01 | 2.78 |
| 17 | HLA-DRB1*11:02 | 0.94 |
| 18 | HLA-DRB1*11:03 | 0.74 |
| 19 | HLA-DRB1*11:04 | 4.76 |

TABLE 1B-continued

HLA class II

| Class II | allele | Frequency in population |
|---|---|---|
| 20 | HLA-DRB1*15:02 | 0.78 |
| 21 | HLA-DRB1*15:03 | 1.22 |
| 22 | HLA-DRB1*16:01 | 4.06 |
| 23 | HLA-DRB1*16:02 | 0.84 |
| 24 | HLA-DRB3*02:02 | 0.00 |
| 25 | HLA-DRB3*03:01 | 0.00 |
| 26 | HLA-DRB5*01:01 | 0.00 |
| 27 | HLA-DQA1*01:01/DQB1*05:01 | 30.57 |
| 28 | HLA-DQA1*05:01/DQB1*02:01 | 76.17 |
| 29 | HLA-DQA1*01:02/DQB1*05:02 | 21.13 |
| 30 | HLA-DQA1*01:02/DQB1*06:02 | 30.74 |
| 31 | HLA-DQA1*03:01/DQB1*03:02 | 31.56 |
| 32 | HLA-DQA1*01:02/DQB1*06:04 | 19.00 |
| 33 | HLA-DQA1*05:01/DQB1*03:01 | 80.58 |
| 34 | HLA-DQA1*02:01/DQB1*02:02 | 27.99 |
| 35 | HLA-DQA1*03:01/DQB1*03:01 | 49.92 |
| 36 | HLA-DQA1*02:01/DQB1*03:03 | 23.32 |
| 37 | HLA-DQA1*03:03/DQB1*03:03 | 20.22 |
| 38 | HLA-DPA1*01:03/DPB1*01:01 | 99.83 |
| 39 | HLA-DPA1*01:03/DPB1*02:01 | 99.83 |
| 40 | HLA-DPA1*01:03/DPB1*03:01 | 99.82 |
| 41 | HLA-DPA1*01:03/DPB1*04:01 | 99.88 |
| 42 | HLA-DPA1*01:03/DPB1*04:02 | 99.86 |
| 43 | HLA-DPA1*01:03/DPB1*05:01 | 99.81 |
| 44 | HLA-DPA1*02:01/DPB1*01:01 | 23.54 |
| 45 | HLA-DPA1*02:01/DPB1*02:01 | 24.11 |
| 46 | HLA-DPA1*02:01/DPB1*03:01 | 17.63 |
| 47 | HLA-DPA1*02:01/DPB1*04:01 | 46.73 |
| 48 | HLA-DPA1*02:01/DPB1*04:02 | 38.04 |
| 49 | HLA-DPA1*02:01/DPB1*05:01 | 13.24 |
| 50 | HLA-DPA1*02:01/DPB1*06:01 | 8.59 |
| 51 | HLA-DPA1*02:01/DPB1*09:01 | 7.26 |
| 52 | HLA-DPA1*02:01/DPB1*11:01 | 9.98 |
| 53 | HLA-DPA1*02:01/DPB1*13:01 | 11.55 |
| 54 | HLA-DPA1*02:01/DPB1*14:01 | 7.98 |
| 55 | HLA-DPA1*02:01/DPB1*15:01 | 7.73 |
| 56 | HLA-DPA1*02:01/DPB1*17:01 | 10.40 |

Figure 4A:
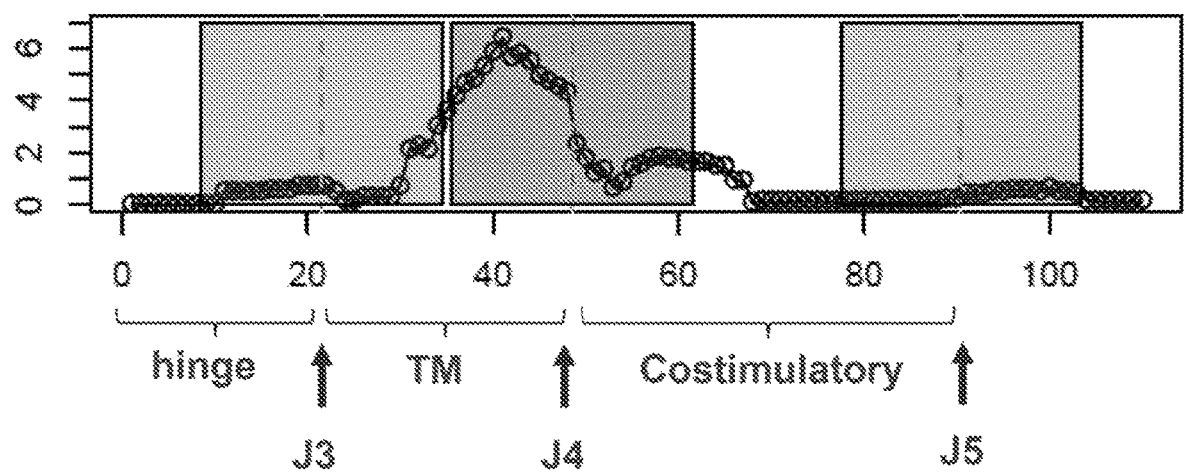
FIG. 4A and FIG. 4B depict algorithm-based T cell epitope predictions for HLA class I and HLA class II alleles, respectively, showing the total number of sequences in the dataset including each position along the length of the sequence with a predicted IC50 of less than 50 nm weighted according to the frequency of the individual HLA alleles in the population.

Algorithm-based T cell epitope prediction tools available from the IEDB were used to predict IC50 values for binding to HLA class I molecules for each 8-14 amino acid peptide in the dataset using ANN (Nielsen et al. (2003) Protein Sci., 12:1007-1017 and Lundegaard et al. (2008) NAR, 36: W509-512) and, in some cases, one or more additional prediction using SMM (Peters and Sette (2005) BMC Bioinformatics, 6:132) and comblib (Sidney et al. (2008) Immunome Res. 4:2, or the Consensus tool (see Kim, et al. (2012) Immune epitope database analysis resource, NAR (combining predictions from any of the foregoing). Predictions for IC50 values for binding to HLA class II for each 15 amino acid peptide in the dataset was made using the NetMHCII-pan method (Karosiene et al. (2013) Immunogenetics 65 (10): 711; Nielsen et al. (2008) PLOS Comput Biol. 4 (7) e1000107). For each individual position within the portion of the CAR amino acid sequence, the total number of sequences in the dataset that included the position and was predicted to bind to any of the class I or class II alleles with a predicted IC50 of less than 50 nm was determined. FIGS. 4A (HLA class I) and 4B (HLA class II), depict the results for class I and class II alleles, respectively, showing positional coverage along the length of the sequence, based on the determined total number, weighted according to the frequency of the individual HLA alleles in the population. The area under the curve (AUC) across the entire assessed region was approximately 1321 for HLA class I binding and 2943 for HLA class II binding. The AUC for the transmembrane-costimulatory domain region was approximately 931 for HLA class I binding and 2212 for HLA class II binding.

Figure 4B:
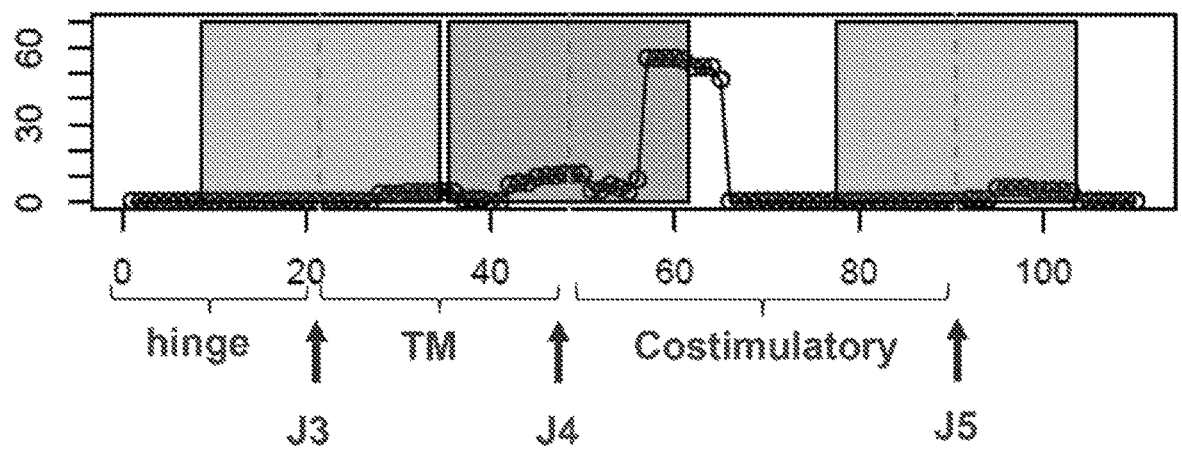
Figure 5:
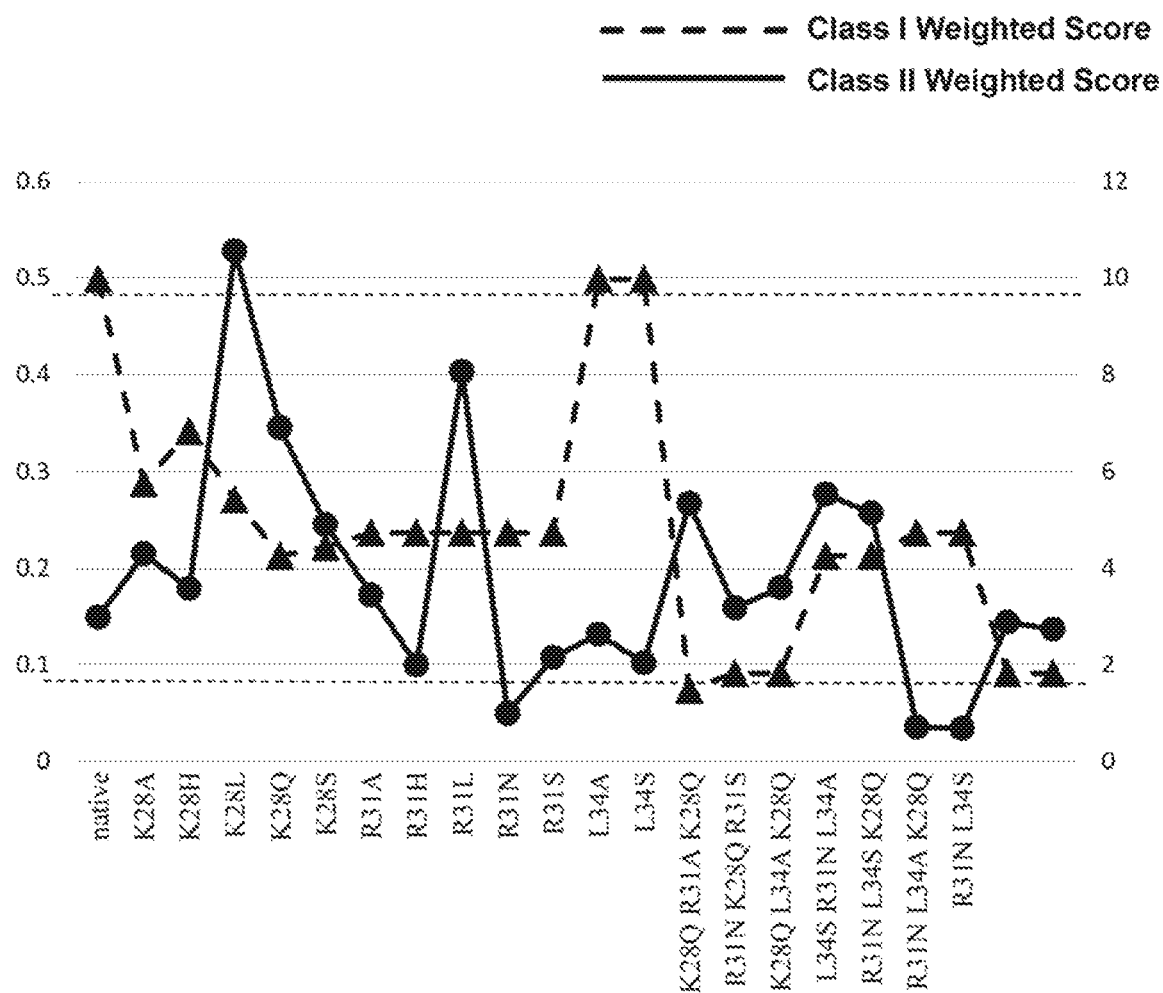
FIG. 5 depicts algorithm-based T cell epitope predictions for HLA class I and HLA class II alleles of a series of variant peptides. Scores were determined and weighted as described in Example 2. Triangles and a dotted line indicated class I weighted scores. Circles and a solid line indicate class II weighted scores.

As shown in FIGS. 4A and 4B, certain portions of the sequence were predicted by this method to contain fragments more likely to bind well in MHC complexes and thus be presented as epitopes for potential recognition by T cells. Binding affinity for HLA alleles alone does not necessarily predict immunogenicity. Given that the individual domains (e.g., transmembrane, costimulatory) in this exemplary CAR were human-derived, upon administration to a human subject, immunogenic responses were less likely to develop against an epitope within any one of these individual regions alone (as opposed to an epitope spanning multiple regions not ordinarily associated with one another, and/or including a junction between such regions). For example, even for a peptide predicted to bind well to and be presented in the context of an MHC molecule, if the peptide was derived entirely from an endogenous protein, it may be recognized as "self" and thus may fail to induce a productive immune response. For example, whereas certain regions entirely within a single transmembrane or cytoplasmic domain scored highly on the HLA-binding affinity prediction, in the results described in Example 1, no immune responses were detected against peptide sequences solely within either one of these domains of a similar CAR sequence. Accordingly, while various "hot spots" were observed with respect to predicted HLA-binding affinity, subsequent assessment and alteration focused on those areas that not only had higher predicted IC50 values, but also included potential epitopes that spanned the junction between different domains derived from two different proteins.

In particular, a junction region that includes one or more potential peptide epitopes spanning the junction of the CD28 transmembrane domain and 4-1BB signaling domain of the exemplary CAR was further assessed. With respect to the sequence set forth in SEQ ID NO:5, which includes the exemplary human CD28 transmembrane domain (SEQ ID NO:2) and exemplary human 4-1BB costimulatory domain (SEQ ID NO:3), the assessed junction region contained 13 amino acids on either side of the junction spanning the CD28 transmembrane and 4-1BB costimulatory domains as follows: FWVLVVVGGVLACYSLLVTVAFIIFWV<u>K</u>R-GRKKLLYIFKQPFMRPVQTTQEEDGCSC RFPEEEEGGCEL (SEQ ID NO:5), in which a 26 amino acid junction region is indicated by bold, and the two amino acids just C' and N' of the junction between the domains is indicated by underline. The assessed 26 amino acid junction region is set forth in SEQ ID NO:137 and corresponds to amino acid residues 15 to 40 of the sequence of amino acids set forth in SEQ ID NO: 5.

In silico modeling was carried out to identify one or more amino acid modifications (mutations) within the 26-amino acid junction region set forth in SEQ ID NO: 137 resulting in peptide fragments that were predicted to bind with high IC50 values to class I and class II alleles, and thus that were likely to reduce the potential for inducing immunogenicity against a CAR containing this region. Specifically, predictions were made for variant peptide fragments of the junction region containing one or more mutations at amino acid residue positions corresponding to positions 14, 17 and 20 with numbering with reference to SEQ ID NO:137 (which correspond to one or more mutations at amino acid positions corresponding to positions 28, 31 and 34 with numbering with reference to SEQ ID NO:5). In this exemplary study, these residues were chosen for further analysis following in silico mutagenesis and binding predictions of all high affinity epitopes in which all possible single amino acid replacements across that epitope were surveyed for their impact on the predicted IC50 values. Residues that resulted in greater IC50 predictions (decrease in the binding) were identified, which identified the above residues as being sensitive to replacements.

A series of different variant junction regions were assessed, each containing one or more amino acid replacement at the assessed position(s), as compared to the non-mutated junction region within the exemplary CAR sequence. An exemplary subset of amino acid replacements at the identified positions were chosen that may be less disruptive to the structure or function of either the transmembrane region of the costimulatory signaling domain. Also, replacements were chosen that may be able to impact more than one epitope at a time, since the epitopes overlap. Specifically, individual variant junction regions contained the following modifications (amino acid replacements): K28A, K28H, K28L, K28Q, K28S, R31A, R31H, R31L, R31N, R31S, L34A, L34S, K28Q/R31A, K28Q/R31N, K28Q/R31S, K28Q/L34A, K28Q/L34S, R31N/L34A, R31N/L34S, K28Q/R31N/L34A, K28Q/R31N/L34S, with numbering with reference to SEQ ID NO:5.

For the non-variant and variant junction regions, weighted immunogenicity scores were obtained for class I and class II alleles, using the T cell epitope prediction tools available from IEDB. Scores were derived using predicted IC50 values for each of a series of 8-mer to 14-mer overlapping peptides (for each of the 27 HLA class I alleles, individually) and a series of 15-mer overlapping peptides (for each of the 56 HLA class II alleles, individually) within the respective (variant or non-variant) 26-amino acid junction region, and were weighted based on relative frequency in the population of the individual HLA class I and class II alleles. A higher relative score is indicative of a higher degree of predicted binding.

The results are set forth in FIG. 5. The results demonstrate the ability to decrease in the overall predicted HLA class I immunogenicity score within a CAR junction region by modifying amino acids within the region. The results also confirm the ability to reduce predicted HLA class I binding affinity (and hence reduced predicted immunogenicity score) without resulting in a substantial increase in the predicted immunogenicity score for HLA class II binding. Thus, in general, the results showed that amino acid modification(s) within a region spanning a junction between a CD28 transmembrane domain and a 4-1BB costimulatory domain of a CAR could be made and effect an overall reduction in the predicted affinity for human HLA binding, which would be consistent with a reduction in potential for immunogenicity, upon administration to a human subject, of a chimeric receptor identical to a receptor having this region, but containing the modification or combination of modifications in this region.

Example 3: Comparison of In Silico Analysis and In Vitro Binding of Peptides Derived from Junction Regions of a CAR for Binding to HLA Class I Actual binding affinities for certain HLA class I alleles (A*02:01, A*03:01. A*11:01, and B*08:01) were assessed in vitro for exemplary overlapping 9 amino acid peptide sequences within a portion of the 26 amino acid junction region spanning the CD28 and 4-1BB junction. Specifically, assessment was of a series of overlapping 9-mer peptides derived from the sequence VAFIIFWVKRGRKKLL (set forth in SEQ ID NO: 7), which contains a portion of the CD28 transmembrane domain and 4-1BB costimulatory domain spanning the junction between the domains (bond joining the two amino acids noted in underline). In addition, a series of overlapping 9-mer peptides of each of a number of different variants of this portion also were assessed, each variant containing a mutation or mutations in this region as described in Example 2.

The various 9-mer overlapping peptides were synthesized and their purity tested by MALDI-TOF Mass Spectrometry. The synthetic peptides were then incubated with recombinant MHC molecules to assess binding properties using the REVEAL Epitope Discovery System, which is a high-throughput binding assay that measures the degree to which each peptide is able to stabilize a ternary MHC-peptide complex (ProImmune, Oxford, United Kingdom). Each peptide was separately tested for this ability with respect to each of the HLA class I alleles, normalized to the degree observed for a positive control (known T cell epitope for the relevant allele). The results are reported as a score, in which the binding was normalized to the positive control peptide set at 100%. In this analysis, a score of greater than 50 generally was considered to represent good or high affinity binding.

The results were compared to predicted binding (IC50) values obtained for binding of the same peptide:MHC complex, using the in silico prediction methods as described in Example 2. Since the maximum IC50 value predicted was about 50,000, the IC50 values were log transformed, subtracted from LOG(50000) and divided by LOG(50000) to obtain a normalized in silico score ((Log(50000)−log IC50)/Log(50000)). In this analysis, an in silico binding prediction score of greater than 2.0 generally was considered to represent predicted good or high affinity binding.

The results are set forth in Table 2A (HLA-A*02:01 and HLA-A*03:01) and Table 2B (HLA-A*11:01 and HLA-B*08:01). In general, the in silico binding predictions were predictive of the actual in vitro binding results. In some cases, a relatively higher binding was predicted in silico, but not observed in the in vitro assay.

The results also were consistent with predicted binding affinity being generally predictive of affinity as measured in the in vitro assay. Additionally, the results demonstrated successful reduction of binding affinity to an HLA by modifications within a junction region, and that it was possible to modify the sequence in a way that resulted in a lower predicted or actual binding affinity or score of one of the overlapping potential epitopes, without increasing (or while also reducing) binding affinity or score for another of the overlapping epitopes containing the same residue. In some embodiments, such mutations or modifications may be particularly advantageous. As a non-limiting example of the results, modifications K28L, R31H, L34S and/or L34A, with reference to numbering set forth in SEQ ID NO:5, generally resulted in a reduced predicted or actual binding affinity or score for at least one HLA allele and/or for at least one peptide within the region assessed, without resulting in a higher binding affinity to another HLA allele and/or without resulting in a higher binding affinity for another peptide.

TABLE 2A

In Silico and In Vitro MHC binding of Variant Peptides

| Overlapping Reference Peptide | Peptide Sequence | Mutation | A*02:01 IEDB IC50 | A*02:01 In Silico Score | A*02:01 In Vitro Score | A*03:01 IEDB IC50 | A*03:01 In Silico | A*03:01 In Vitro | SEQ ID NO. |
|---|---|---|---|---|---|---|---|---|---|
| 1 | VAFIIFWVK | none | 19617 | 0.41 | 0.70 | 262 | 2.28 | 1.50 | 16 |
| 2 | AFIIFWVKR | none | 25314 | 0.30 | 0.50 | 17846 | 0.45 | 5.70 | 17 |
| 3 | FIIFWVKRG | none | 7967 | 0.80 | 10.10 | 23693 | 0.32 | 1.40 | 18 |
| 4 | IIFWVKRGR | none | 24769 | 0.31 | 1.70 | 406 | 2.09 | 24.30 | 19 |
| 5 | IFWVKRGRK | none | 30463 | 0.22 | 4.50 | 3482 | 1.16 | 20.50 | 20 |
| 6 | FWVKRGRKK | none | 28878 | 0.24 | 3.50 | 17327 | 0.46 | 2.20 | 21 |
| 7 | WVKRGRKKL | none | 27956 | 0.25 | 1.40 | 22961 | 0.34 | 13.10 | 22 |
| 1 | VAFIIFWVS | K28S | 12273 | 0.61 | 70.60 | 22660 | 0.34 | 0.70 | 23 |
| 2 | AFIIFWVSR | K28S | 23924 | 0.32 | 4.50 | 18157 | 0.44 | 0.30 | 24 |
| 3 | FIIFWVSRG | K28S | 3382 | 1.17 | 0.20 | 21751 | 0.36 | 0.10 | 25 |
| 4 | IIFWVSRGR | K28S | 21442 | 0.37 | 2.60 | 155 | 2.51 | 25.30 | 26 |
| 5 | IFWVSRGRK | K28S | 30615 | 0.21 | 1.30 | 1880 | 1.42 | 39.20 | 27 |
| 6 | FWVSRGRKK | K28S | 28679 | 0.24 | 1.50 | 17832 | 0.45 | 2.90 | 28 |
| 7 | WVSRGRKKL | K28S | 23551 | 0.33 | 2.30 | 22394 | 0.35 | 2.10 | 29 |
| 1 | VAFIIFWVL | K28L | 1336 | 1.57 | 0.20 | 20145 | 0.39 | 0.00 | 30 |
| 2 | AFIIFWVLR | K28L | 22444 | 0.35 | 5.70 | 15583 | 0.51 | 0.30 | 31 |
| 3 | FIIFWVLRG | K28L | 2037 | 1.39 | 7.20 | 20853 | 0.38 | 0.10 | 32 |
| 4 | IIFWVLRGR | K28L | 17613 | 0.45 | 8.40 | 238 | 2.32 | 2.80 | 33 |
| 5 | IFWVLRGRK | K28L | 30293 | 0.22 | 2.90 | 3675 | 1.13 | 19.50 | 34 |
| 6 | FWVLRGRKK | K28L | 28857 | 0.24 | 3.30 | 16996 | 0.47 | 0.40 | 35 |
| 7 | WVLRGRKKL | K28L | 19522 | 0.41 | 2.40 | 23063 | 0.34 | 0.70 | 36 |
| 1 | VAFIIFWVH | K28H | 23252 | 0.33 | 3.10 | 10359 | 0.68 | 0.30 | 37 |
| 2 | AFIIFWVHR | K28H | 22819 | 0.34 | 0.30 | 18506 | 0.43 | 0.30 | 38 |
| 3 | FIIFWVHRG | K28H | 1691 | 1.47 | 37.30 | 22930 | 0.34 | 0.00 | 39 |
| 4 | IIFWVHRGR | K28H | 23573 | 0.33 | 4.70 | 326 | 2.19 | 30.10 | 40 |
| 5 | IFWVHRGRK | K28H | 29930 | 0.22 | 7.10 | 1062 | 1.67 | 37.80 | 41 |
| 6 | FWVHRGRKK | K28H | 28189 | 0.25 | 1.60 | 17052 | 0.47 | 3.60 | 42 |
| 7 | WVHRGRKKL | K28H | 25035 | 0.30 | 1.60 | 22278 | 0.35 | 3.40 | 43 |
| 1 | VAFIIFWVA | K28A | 2733 | 1.26 | 28.50 | 21010 | 0.38 | 0.00 | 44 |
| 2 | AFIIFWVAR | K28A | 23072 | 0.34 | 2.20 | 17755 | 0.45 | 0.50 | 45 |
| 3 | FIIFWVARG | K28A | 1902 | 1.42 | | 22486 | 0.35 | | 102 |
| 4 | IIFWVARGR | K28A | 22077 | 0.36 | 9.60 | 206 | 2.39 | 18.60 | 46 |
| 5 | IFWVARGRK | K28A | 30251 | 0.22 | 1.00 | 3893 | 1.11 | 53.70 | 47 |
| 6 | FWVARGRKK | K28A | 28353 | 0.25 | 13.50 | 16210 | 0.49 | 5.00 | 48 |
| 7 | WVARGRKKL | K28A | 22630 | 0.34 | 8.80 | 22548 | 0.35 | 1.30 | 49 |
| 1 | VAFIIFWVQ | K28Q | 17921 | 0.45 | 5.30 | 22927 | 0.34 | 0.20 | 50 |
| 2 | AFIIFWVQR | K28Q | 24165 | 0.32 | 0.40 | 19279 | 0.41 | 0.20 | 51 |
| 3 | FIIFWVQRG | K28Q | 4152 | 1.08 | 16.80 | 23136 | 0.33 | 0.40 | 52 |
| 4 | IIFWVQRGR | K28Q | 21783 | 0.36 | 5.80 | 231 | 2.34 | 18.00 | 53 |
| 5 | IFWVQRGRK | K28Q | 30704 | 0.21 | 6.10 | 3177 | 1.20 | 36.70 | 54 |
| 6 | FWVQRGRKK | K28Q | 29501 | 0.23 | 5.20 | 18619 | 0.43 | 6.40 | 55 |
| 7 | WVQRGRKKL | K28Q | 24480 | 0.31 | 8.10 | 23630 | 0.33 | 4.90 | 56 |
| 4 | IIFWVKRGS | R31S | 18902 | 0.42 | 13.60 | 19450 | 0.41 | 16.20 | 57 |
| 5 | IFWVKRGSK | R31S | 29391 | 0.23 | 2.40 | 3348 | 1.17 | 10.40 | 58 |
| 6 | FWVKRGSKK | R31S | 28317 | 0.25 | 1.90 | 14227 | 0.55 | 5.90 | 59 |
| 7 | WVKRGSKKL | R31S | 23485 | 0.33 | 3.00 | 22637 | 0.34 | 1.90 | 60 |
| 4 | IIFWVKRGL | R31L | 2692 | 1.27 | 82.20 | 16661 | 0.48 | 15.90 | 61 |
| 5 | IFWVKRGLK | R31L | 29250 | 0.23 | 2.40 | 1973 | 1.40 | 26.90 | 62 |
| 6 | FWVKRGLKK | R31L | 27554 | 0.26 | 9.40 | 14434 | 0.54 | 2.70 | 63 |
| 7 | WVKRGLKKL | R31L | 20709 | 0.38 | 24.50 | 22985 | 0.34 | 10.00 | 64 |
| 4 | IIFWVKRGH | R31H | 27453 | 0.26 | 5.30 | 1665 | 1.48 | 26.60 | 65 |
| 5 | IFWVKRGHK | R31H | 29806 | 0.22 | 2.20 | 3806 | 1.12 | 9.00 | 66 |
| 6 | FWVKRGHKK | R31H | 27689 | 0.26 | 2.60 | 16743 | 0.48 | 4.10 | 67 |
| 7 | WVKRGHKKL | R31H | 25923 | 0.29 | 3.90 | 22313 | 0.35 | 1.40 | 68 |
| 4 | IIFWVKRGA | R31A | 6107 | 0.91 | 85.90 | 16069 | 0.49 | 42.90 | 69 |
| 5 | IFWVKRGAK | R31A | 29354 | 0.23 | 13.80 | 3470 | 1.16 | 22.00 | 70 |
| 6 | FWVKRGAKK | R31A | 28151 | 0.25 | 4.30 | 17066 | 0.47 | 4.70 | 71 |
| 7 | WVKRGAKKL | R31A | 24746 | 0.31 | 4.70 | 22982 | 0.34 | 4.10 | 72 |
| 4 | IIFWVKRGN | R31N | 25979 | 0.28 | 9.30 | 18552 | 0.43 | 4.30 | 73 |
| 5 | IFWVKRGNK | R31N | 29978 | 0.22 | 3.50 | 2669 | 1.27 | 8.00 | 74 |
| 6 | FWVKRGNKK | R31N | 28430 | 0.25 | 8.70 | 17713 | 0.45 | 3.60 | 75 |
| 7 | WVKRGNKKL | R31N | 24790 | 0.30 | 2.40 | 22813 | 0.34 | 0.90 | 76 |
| 4 | IIFWVQRGS | K28Q/R31S | 14326 | 0.54 | 22.40 | 17741 | 0.45 | 4.50 | 77 |
| 5 | IFWVQRGSK | K28Q/R31S | 29540 | 0.23 | 33.50 | 3052 | 1.21 | 20.30 | 78 |
| 6 | FWVQRGSKK | K28Q/R31S | 28907 | 0.24 | 0.80 | 15992 | 0.50 | 1.90 | 79 |
| 7 | WVQRGSKKL | K28Q/R31S | 18121 | 0.44 | 4.40 | 23279 | 0.33 | 1.20 | 80 |
| 4 | IIFWVQRGA | K28Q/R31A | 2658 | 1.27 | 95.30 | 13467 | 0.57 | 2.70 | 81 |
| 5 | IFWVQRGAK | K28Q/R31A | 29482 | 0.23 | 11.70 | 3205 | 1.19 | 17.00 | 82 |
| 6 | FWVQRGAKK | K28Q/R31A | 28792 | 0.24 | 2.20 | 18649 | 0.43 | 2.70 | 83 |
| 7 | WVQRGAKKL | K28Q/R31A | 20217 | 0.39 | 3.00 | 23651 | 0.33 | 2.00 | 84 |
| 4 | IIFWVQRGN | K28Q/R31N | 23103 | 0.34 | 13.00 | 16590 | 0.48 | 3.60 | 85 |
| 5 | IFWVQRGNK | K28Q/R31N | 30164 | 0.22 | 16.10 | 2438 | 1.31 | 23.20 | 86 |
| 6 | FWVQRGNKK | K28Q/R31N | 29113 | 0.23 | 3.10 | 19165 | 0.42 | 1.30 | 87 |

TABLE 2A-continued

In Silico and In Vitro MHC binding of Variant Peptides

| Overlapping Reference Peptide | Peptide Sequence | Mutation | A*02:01 IEDB IC50 | A*02:01 In Silico Score | A*02:01 In Vitro Score | A*03:01 IEDB IC50 | A*03:01 In Silico Score | A*03:01 In Vitro Score | SEQ ID NO. |
|---|---|---|---|---|---|---|---|---|---|
| 7 | WVQRGNKKL | K28Q/R31N | 19790 | 0.40 | 4.30 | 23457 | 0.33 | 1.50 | 88 |
| 7 | WVKRGRKKS | L34S | 30812 | 0.21 | 3.90 | 25365 | 0.29 | 0.90 | 89 |
| 7 | WVKRGRKKA | L34A | 28556 | 0.24 | 4.50 | 24086 | 0.32 | 0.90 | 90 |
| 7 | WVQRGNKKS | K28Q/L34S | 26883 | 0.27 | 1.20 | 25680 | 0.29 | 0.70 | 91 |
| 7 | WVQRGNKKA | K28Q/L34A | 21998 | 0.36 | 1.90 | 24564 | 0.31 | 1.20 | 92 |
| 1 | VAFIIFWVR | K28R | 20045 | 0.40 | 1.20 | 5746 | 0.94 | 0.70 | 100 |
| 2 | AFIIFWVRR | K28R | 25059 | 0.30 | 1.40 | 17924 | 1.00 | | 101 |

TABLE 2B

In Silico and In Vitro MHC binding of Variant Peptides

| Overlapping Reference Peptide | Peptide Sequence | Mutation | A*11:01 IEDB IC50 | A*11:01 In Silico Score | A*11:01 In Vitro Score | B*08:01 IEDB IC50 | B*08:01 In Silico Score | B*08:01 In Vitro Score | SEQ ID NO. |
|---|---|---|---|---|---|---|---|---|---|
| 1 | VAFIIFWVK | wt | 19 | 3.42 | 109.20 | 15806 | 0.50 | 0.30 | 16 |
| 2 | AFIIFWVKR | wt | 3271 | 1.18 | 25.90 | 23244 | 0.33 | 1.90 | 17 |
| 3 | FIIFWVKRG | wt | 22946 | 0.34 | 0.40 | 18081 | 0.44 | 0.10 | 18 |
| 4 | IIFWVKRGR | wt | 706 | 1.85 | 54.50 | 23025 | 0.34 | 0.00 | 19 |
| 5 | IFWVKRGRK | wt | 9701 | 0.71 | 29.30 | 23513 | 0.33 | 0.40 | 20 |
| 6 | FWVKRGRKK | wt | 22175 | 0.35 | 6.50 | 21764 | 0.36 | 0.00 | 21 |
| 7 | WVKRGRKKL | wt | 24020 | 0.32 | 4.80 | 225 | 2.35 | 28.50 | 22 |
| 1 | VAFIIFWVS | K28S | 12403 | 0.61 | 25.10 | 13796 | 0.56 | 0.10 | 23 |
| 2 | AFIIFWVSR | K28S | 2175 | 1.36 | 54.00 | 21862 | 0.36 | 0.30 | 24 |
| 3 | FIIFWVSRG | K28S | 20651 | 0.38 | 5.10 | 17854 | 0.45 | 0.40 | 25 |
| 4 | IIFWVSRGR | K28S | 162 | 2.49 | 68.90 | 23445 | 0.33 | 0.00 | 26 |
| 5 | IFWVSRGRK | K28S | 5778 | 0.94 | 39.20 | 23448 | 0.33 | 0.00 | 27 |
| 6 | FWVSRGRKK | K28S | 21126 | 0.37 | 6.30 | 23067 | 0.34 | 0.00 | 28 |
| 7 | WVSRGRKKL | K28S | 23684 | 0.32 | 4.40 | 3208 | 1.19 | 6.20 | 29 |
| 1 | VAFIIFWVL | K28L | 14191 | 0.55 | 0.20 | 1196 | 1.62 | 0.00 | 30 |
| 2 | AFIIFWVLR | K28L | 850 | 1.77 | 17.20 | 23012 | 0.34 | 0.20 | 31 |
| 3 | FIIFWVLRG | K28L | 19162 | 0.42 | 2.40 | 17427 | 0.46 | 0.20 | 32 |
| 4 | IIFWVLRGR | K28L | 185 | 2.43 | 35.20 | 23298 | 0.33 | 0.40 | 33 |
| 5 | IFWVLRGRK | K28L | 6386 | 0.89 | 29.30 | 23324 | 0.33 | 0.00 | 34 |
| 6 | FWVLRGRKK | K28L | 21862 | 0.36 | 5.00 | 23437 | 0.33 | 0.00 | 35 |
| 7 | WVLRGRKKL | K28L | 23725 | 0.32 | 3.20 | 1342 | 1.57 | 4.00 | 36 |
| 1 | VAFIIFWVH | K28H | 1209 | 1.62 | 12.30 | 16202 | 0.49 | 0.00 | 37 |
| 2 | AFIIFWVHR | K28H | 4939 | 1.01 | 34.90 | 22682 | 0.34 | 0.30 | 38 |
| 3 | FIIFWVHRG | K28H | 19850 | 0.40 | 0.90 | 17464 | 0.46 | 0.20 | 39 |
| 4 | IIFWVHRGR | K28H | 196 | 2.41 | 77.50 | 22662 | 0.34 | 0.20 | 40 |
| 5 | IFWVHRGRK | K28H | 7133 | 0.85 | 36.60 | 22030 | 0.36 | 0.10 | 41 |
| 6 | FWVHRGRKK | K28H | 22214 | 0.35 | 5.60 | 23778 | 0.32 | 0.00 | 42 |
| 7 | WVHRGRKKL | K28H | 23844 | 0.32 | 5.60 | 814 | 1.79 | 19.20 | 43 |
| 1 | VAFIIFWVA | K28A | 12499 | 0.60 | 2.80 | 5131 | 0.99 | 0.00 | 44 |
| 2 | AFIIFWVAR | K28A | 2784 | 1.25 | 51.80 | 21850 | 0.36 | 0.20 | 45 |
| 3 | FIIFWVARG | K28A | 20922 | 0.38 | | 18463 | 0.43 | | 102 |
| 4 | IIFWVARGR | K28A | 239 | 2.32 | 70.60 | 23580 | 0.33 | 0.30 | 46 |
| 5 | IFWVARGRK | K28A | 8772 | 0.76 | 34.90 | 23612 | 0.33 | 0.00 | 47 |
| 6 | FWVARGRKK | K28A | 20762 | 0.38 | 8.90 | 23035 | 0.34 | 0.00 | 48 |
| 7 | WVARGRKKL | K28A | 23920 | 0.32 | 13.80 | 2821 | 1.25 | 32.40 | 49 |
| 1 | VAFIIFWVQ | K28Q | 15477 | 0.51 | 3.90 | 14875 | 0.53 | 0.20 | 50 |
| 2 | AFIIFWVQR | K28Q | 2174 | 1.36 | 15.00 | 23016 | 0.34 | 0.00 | 51 |
| 3 | FIIFWVQRG | K28Q | 22161 | 0.35 | 1.50 | 17653 | 0.45 | 0.60 | 52 |
| 4 | IIFWVQRGR | K28Q | 361 | 2.14 | 72.80 | 23548 | 0.33 | 0.10 | 53 |
| 5 | IFWVQRGRK | K28Q | 9561 | 0.72 | 128.50 | 23670 | 0.32 | 0.00 | 54 |
| 6 | FWVQRGRKK | K28Q | 22394 | 0.35 | 5.70 | 22604 | 0.34 | 1.90 | 55 |
| 7 | WVQRGRKKL | K28Q | 23688 | 0.32 | 12.80 | 2512 | 1.30 | 45.10 | 56 |
| 4 | IIFWVKRGS | R31S | 18923 | 0.42 | 100.00 | 22325 | 0.35 | 0.40 | 57 |
| 5 | IFWVKRGSK | R31S | 7476 | 0.83 | 47.90 | 21691 | 0.36 | 1.20 | 58 |
| 6 | FWVKRGSKK | R31S | 19910 | 0.40 | 5.60 | 20823 | 0.38 | 0.10 | 59 |
| 7 | WVKRGSKKL | R31S | 24090 | 0.32 | 11.80 | 585 | 1.93 | 56.10 | 60 |
| 4 | IIFWVKRGL | R31L | 20182 | 0.39 | 32.40 | 17368 | 0.46 | 1.70 | 61 |
| 5 | IFWVKRGLK | R31L | 4201 | 1.08 | 61.10 | 23537 | 0.33 | 58.30 | 62 |
| 6 | FWVKRGLKK | R31L | 17309 | 0.46 | 25.30 | 20839 | 0.38 | 6.30 | 63 |
| 7 | WVKRGLKKL | R31L | 24095 | 0.32 | 22.10 | 765 | 1.82 | 65.70 | 64 |
| 4 | IIFWVKRGH | R31H | 7117 | 0.85 | 19.50 | 23227 | 0.33 | 0.10 | 65 |
| 5 | IFWVKRGHK | R31H | 10783 | 0.67 | 30.90 | 23461 | 0.33 | 3.20 | 66 |
| 6 | FWVKRGHKK | R31H | 17635 | 0.45 | 27.60 | 20754 | 0.38 | 0.40 | 67 |

TABLE 2B-continued

In Silico and In Vitro MHC binding of Variant Peptides

| Overlapping Reference Peptide | Peptide Sequence | Mutation | A*11:01 IEDB IC50 | A*11:01 In Silico Score | A*11:01 In Vitro Score | B*08:01 IEDB IC50 | B*08:01 In Silico Score | B*08:01 In Vitro Score | SEQ ID NO. |
|---|---|---|---|---|---|---|---|---|---|
| 7 | WVKRGHKKL | R31H | 23924 | 0.32 | 2.80 | 269 | 2.27 | 47.60 | 68 |
| 4 | IIFWVKRGA | R31A | 19134 | 0.42 | 22.60 | 19585 | 0.41 | 0.90 | 69 |
| 5 | IFWVKRGAK | R31A | 8311 | 0.78 | 69.70 | 21592 | 0.36 | 2.20 | 70 |
| 6 | FWVKRGAKK | R31A | 20234 | 0.39 | 13.20 | 21762 | 0.36 | 0.30 | 71 |
| 7 | WVKRGAKKL | R31A | 23857 | 0.32 | 4.60 | 1366 | 1.56 | 34.10 | 72 |
| 4 | IIFWVKRGN | R31N | 19351 | 0.41 | 42.10 | 22864 | 0.34 | 0.90 | 73 |
| 5 | IFWVKRGNK | R31N | 6780 | 0.87 | 45.90 | 24238 | 0.31 | 0.10 | 74 |
| 6 | FWVKRGNKK | R31N | 20732 | 0.38 | 7.30 | 21565 | 0.37 | 0.10 | 75 |
| 7 | WVKRGNKKL | R31N | 24036 | 0.32 | 4.10 | 1181 | 1.63 | 65.90 | 76 |
| 4 | IIFWVQRGS | K28Q/R31S | 18031 | 0.44 | 16.90 | 22961 | 0.34 | 0.10 | 77 |
| 5 | IFWVQRGSK | K28Q/R31S | 7300 | 0.84 | 103.30 | 22846 | 0.34 | 0.00 | 78 |
| 6 | FWVQRGSKK | K28Q/R31S | 20419 | 0.39 | 6.80 | 21853 | 0.36 | 0.00 | 79 |
| 7 | WVQRGSKKL | K28Q/R31S | 23740 | 0.32 | 5.90 | 5230 | 0.98 | 6.80 | 80 |
| 4 | IIFWVQRGA | K28Q/R31A | 18055 | 0.44 | 56.50 | 20759 | 0.38 | 0.20 | 81 |
| 5 | IFWVQRGAK | K28Q/R31A | 8237 | 0.78 | 61.30 | 22801 | 0.34 | 0.20 | 82 |
| 6 | FWVQRGAKK | K28Q/R31A | 20696 | 0.38 | 18.30 | 22612 | 0.34 | 0.00 | 83 |
| 7 | WVQRGAKKL | K28Q/R31A | 23552 | 0.33 | 3.80 | 8314 | 0.78 | 11.40 | 84 |
| 4 | IIFWVQRGN | K28Q/R31N | 18437 | 0.43 | 29.00 | 23425 | 0.33 | 0.00 | 85 |
| 5 | IFWVQRGNK | K28Q/R31N | 6566 | 0.88 | 67.50 | 24059 | 0.32 | 0.10 | 86 |
| 6 | FWVQRGNKK | K28Q/R31N | 21228 | 0.37 | 5.90 | 22436 | 0.35 | 0.00 | 87 |
| 7 | WVQRGNKKL | K28Q/R31N | 23751 | 0.32 | 10.70 | 7869 | 0.80 | 32.00 | 88 |
| 7 | WVKRGRKKS | L34S | 23906 | 0.32 | 6.70 | 10345 | 0.68 | 4.30 | 89 |
| 7 | WVKRGRKKA | L34A | 23864 | 0.32 | 3.10 | 1225 | 1.61 | 3.10 | 90 |
| 7 | WVQRGNKKS | K28Q/L34S | 23612 | 0.33 | 5.00 | 21235 | 0.37 | 0.00 | 91 |
| 7 | WVQRGNKKA | K28Q/L34A | 23576 | 0.33 | 0.80 | 14247 | 0.55 | 0.70 | 92 |
| 1 | VAFIIFWVR | K28R | 108 | 2.67 | 34.60 | 16290 | 0.49 | 0.10 | 100 |
| 2 | AFIIFWVRR | K28R | 3387 | 1.17 | 1.50 | 22717 | 0.34 | 0.30 | 101 |

Example 4: Analysis of Peptides Derived from Junction Region of a CAR for Binding to HLA-A2:01

In order to identify CAR-derived peptides potentially capable of inducing immunogenic responses, a series of overlapping peptides within the non-variant (reference) sequence containing the junction between the CD28 transmembrane domain and 4-1BB costimulatory domain of a CAR were assessed in silico. Algorithms were used to predict binding affinities for the peptide groove of a common human MHC class I molecule (HLA-A2:01) using in silico analysis to predict affinity for binding. As set forth in FIG. 3, the assessed portion of the CAR had the sequence CYSLLVTVAFIIFWVKRGRKKLLYIFKQPF (set forth in SEQ ID NO: 6), which contains a portion of the of the CD28 transmembrane domain (set forth in SEQ ID NO: 2) and a portion of the 4-1BB costimulatory domain (set forth in SEQ ID NO:3), with the residues spanning the junction of the domains shown by underline. Predicted HLA-A2:01 binding affinity was assessed in silico for a series of 140 overlapping peptides of 8-14 amino acids of the sequence set forth in SEQ ID NO:6. Thirty-five (35) of the peptides contained only sequence from the transmembrane domain portion: 35 of the peptides contained only from the costimulatory domain portion, and 70 of the peptides had a junction or fusion region sequence, containing amino acid residues bridging the junction between the domains. For this assessment, peptide fragments predicted to bind to HLA-A2:01 with a dissociation constant of 0 nM to 50 nM were considered predicted to bind with high affinity. Peptide fragments predicted to bind with a dissociation constant of 51 nM to 1000 nM were considered predicted to bind with low affinity. Peptide fragments predicted to bind with a predicted affinity of 1000 nM to 5000 nM were considered predicted to bind with rare affinity. The results are presented in FIG. 3.

Figure 3:
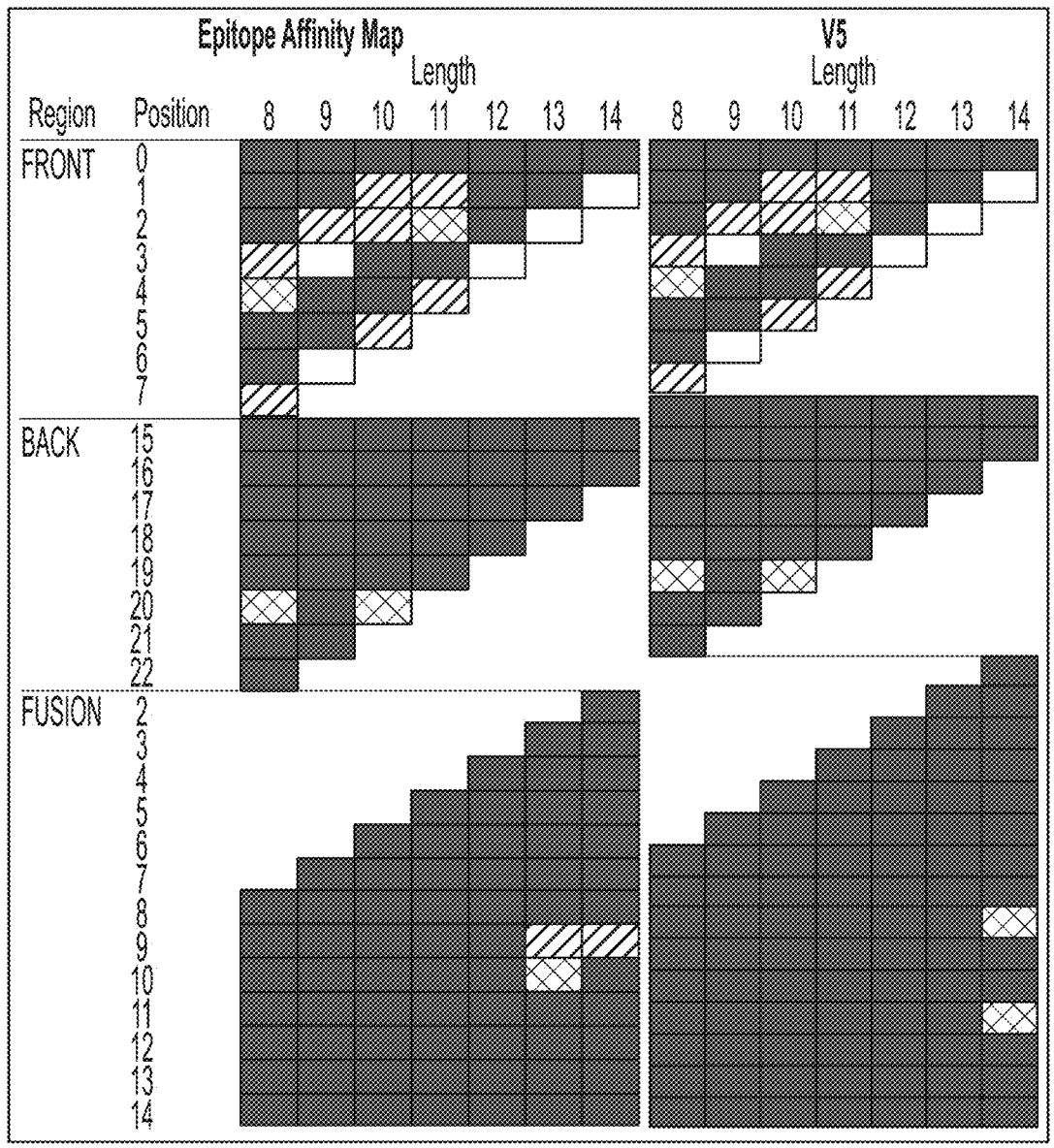
FIG. 3 shows an epitope affinity map for predicted binding affinities of peptides of an exemplary region of a chimeric receptor for binding to HLA-A2:01, including a series of overlapping 8mer to 14mer peptides of an exemplary junction region having an amino acid sequence CYSLLVTVAFIIFWVKRGRKKLLYIFKQPF (SEQ ID NO: 6) where residues 1-15 CYSLLVTVAFIIFWV (SEQ ID NO: 161) correspond to an exemplary CD28 transmembrane domain and residues 16-30 KRGRKKLLYIFKQPF (SEQ ID NO: 166) correspond to an exemplary 4-1BB costimulatory domain. The figure also depicts predicted binding affinities of a series of overlapping 8mer to 14mer peptides of a variant junction region having an amino acid sequence CYSLLVTVAFIIFWVNNKRGRKKLLYIFKQPF (SEQ ID NO: 13), containing inserted asparagine residues between the CD28 transmembrane domain and 4-1BB costimulatory domain.

As shown in FIG. 3, two of the peptides derived from the reference sequence in this region, each containing a sequence with an overlapping region spanning the junction between the domains were predicted to exhibit low binding affinity for HLA-A2:01. Specifically, a 14-mer peptide having the sequence FIIFWVKRGRKKLL (SEQ ID NO: 10), was predicted to bind with a dissociation constant of 294 nM, and a 13-mer peptide having the sequence of FIIFWVKRGRKKL (SEQ ID NO: 11) was predicted to bind with a dissociation constant of 618 nM. These peptides each included a portion of the 15-mer peptide set forth in SEQ ID NO:8 and identified in Example 1. Shorter 8-mer to 12-mer peptides within this sequence were not predicted to exhibit binding to HLA-A2:01. Another 13-mer peptide containing the amino acid sequence IIFWVKRGRKKLL (SEQ ID NO: 12) was predicted to have a rare binding affinity with a predicted dissociation constant of approximately 3000 nM. None of the remaining fragments that bridged the junction between the two domains were predicted by this assay to exhibit binding affinity for HLA-A2:01 (all had a predicted dissociation constant of far greater than 5000 nM, and in most cases higher than 14,000 nm or 20,000 nM or greater). In each of the peptides predicted to bind to HLA-A2:01, neither of the two junction-spanning residues (VK) themselves was predicted to be an anchor residue; rather, such peptides contained these residues in non-flanking positions.

Approximately 15 of the peptides containing sequence derived only from the transmembrane domain were predicted to have a dissociation constant for HLA-A2:01 of less than 5000 nM. Two peptides containing sequence only from the co-stimulatory domain were predicted to have a dissociation constant for HLA-A2:01 binding of less than 5000 nM. The costimulatory domain and transmembrane domain in the assessed sequence are derived from endogenous human sequences, which generally are less likely to be immunogenic to a human subject. For example, in the study described in Example 1, no immune responses were detected that were specific for peptide sequences solely within either one of these domains of the CAR. Accordingly, variants of peptides containing sequence spanning the junction region were assessed.

To generate variant peptides predicted to have reduced binding affinities to HLA-A2:01 and/or reduced immunogenicity in a human subject having this HLA allele, a variant sequence was generated in silico, containing mutations in the junction region as compared to the sequence set forth in SEQ ID NO:6. Given that peptides containing the junction-spanning "VK" residues (at non-anchor positions) were predicted to exhibit high binding affinities for HLA-A2:01, two asparagine residues were inserted in the junction between the CD28 transmembrane and 4-1BB co-stimulatory domains. The variant contained the sequence CYSLL-VTVAFIIFWVNNKRGRKKLLYIFKQPF (set forth in SEQ ID NO: 13, the sequence flanking the junction that was generated by insertion of the asparagine residues is shown in underline). The exemplary variant sequence of SEQ ID NO: 13 was assessed by the same predictive methods. To assess predicted binding affinities for this variant sequence, a series of 154 overlapping fragments of 8-14 amino acids of the sequence set forth in SEQ ID NO: 13 were assessed by in silico analysis as described above, whereby 35 peptides had a sequence only in the transmembrane portion, 35 peptides had a sequence only in the costimulatory domain portion and 84 peptides contained a junction region sequence containing amino acids bridging the domains, including one or both of the inserted asparagine residues.

The results are depicted in FIG. 3. As shown, overall, the HLA-A2:01 binding affinities of overlapping peptides within the variant region containing the junction, collectively, were substantially reduced as compared to the non-variant sequence. In particular, the predicted dissociation constant for binding to HLA-A2:01 of peptides in the portion of the junction region previously predicted to be immunogenic was substantially reduced. For example, peptide variants IIFWVNNKRGRKKL (SEQ ID NO: 14) and IIFWVNNKRGRKK (SEQ ID NO: 15), which included asparagine residues in the altered region flanking the junction compared to peptides identified as set forth in SEQ ID NOS: 10 and 11, respectively, were predicted to exhibit no detectable binding affinity to HLA-A2:01. Two 14-mer peptides, FIIFWVNNKRGRKK (SEQ ID NO:96) and IFWVNNKRGRKKLL (SEQ ID NO:97), were predicted to exhibit a dissociation constant for binding to this HLA indicating a rare binding affinity, within the range of 1000 nM to 5000 nM. All other peptides containing the modified junction region sequence were predicted to exhibit a dissociation constant of greater than 5000 nM, and in most cases higher than 14,000 nM or 20,000 nM or greater, and thus were not predicted to exhibit binding affinity for HLA-A2:01 by this assessment. Additionally, the modification of the junction region sequence did not create any new peptides predicted to have higher binding affinities for HLA-A2:01 within the costimulatory or transmembrane domain regions.

Example 5: Administration of Anti-CD22 CAR-Expressing Cells to Subjects Previously Treated with Anti-CD19 CAR Six subjects with relapsed/refractory CD22+B cell acute lymphoblastic leukemia (ALL) were administered autologous T cells expressing an anti-CD22 chimeric antigen receptor (CAR). The CAR included a human anti-CD22 scFv antibody, a CD8alpha transmembrane domain, a 4-1BB intracellular signaling domain, and a CD3zeta intracellular signaling domain.

All subjects had previously undergone at least one prior allogeneic hematopoietic stem cell transplant and had received treatment with one of various CD19-directed CAR-T cell therapies. Five of the subjects had relapsed with ALL on which CD19 was not detected ("CD19 neg") and one subject was otherwise a non-responder to the prior CD19 CAR therapy.

Table 3 summarizes the characteristics of the treated patients.

TABLE 3

Patient Characteristics

| ID | Age/Sex | Prior HCT | Prior anti-CD19 CAR | CD19 neg relapse | CD22 site density | Pre-HCT disease burden (% leukemia in aspirate) |
|---|---|---|---|---|---|---|
| 1 | 22/M | Y | Y | Y | 2084 | >95% |
| 2 | 20/F | Y (2) | Y | Y | 13452 | 5% |
| 3 | 22/M | Y | Y | Y | 846 | >90% |
| 4 | 22/M | Y | Y | N | 2589 | 95% |
| 5 | 7/F | Y | Y | Y | 2839 | 32% |
| 6 | 17/F | Y | Y | Y | 2185 | 1% |

HCT: hematopoietic cell transplantation.

Prior to administration of the cells, patients underwent autologous leukapheresis to harvest peripheral blood mononuclear cells (PBMCs). T cells were isolated from the harvested PBMCs by immunoaffinity-based enrichment for CD3 expression and cultured in the presence of anti-CD3/-CD28 beads, followed by transduction with a lentiviral vector encoding the anti-CD22 CAR. The cells were cultured for 7-10 days. Subjects received induction chemotherapy with 25 mg/m fludarabine on Days −4, −3 and −2 and 900 mg/m cyclophosphamide on day −2 (cell infusion on Day 0). Each patient received an initial CAR T cell dose of $3 \times 10^5$ transduced T-cells/recipient weight (kg) by intravenous infusion. The second subject enrolled developed grade 3 diarrhea, meeting the criteria for dose-limiting toxicity (DLT), which led to dose expansion at the first dose-level to treat a total of 6 subjects. No subsequent DLTs were seen at this dosage. Two subjects developed grade 1 cytokine release syndrome (CRS), one subject developed grade 2 CRS, and in two subjects CRS was not present.

The number of CAR-T cells in peripheral blood, bone marrow or cerebrospinal fluid was determined at certain timepoints post-treatment by incubating cells with CD22-Fc. For patients in which expansion was observed, evidence for CAR-T cell expansion was seen in peripheral blood, bone marrow and cerebrospinal fluid, beginning at about day 7. The maximum or peak CAR-T cell expansion was generally observed between about day 12 and about day 15 post-infusion. Table 7 sets forth the maximum or peak percentage of anti-CD22 CAR-T cells observed in this assessment period as a percentage of total T cells in each sample for the treated subjects. Clinical responses were evaluated at day 28 (+/−4 days) post-infusion.

As shown in Table 4, the results were consistent with responses being generally correlated to degree of CAR-T cell expansion. For three subjects that exhibited no or low CAR-T cell expansion also showed evidence of disease progression. Two other subjects had stable disease, and one was observed with complete remission with no MRD. Flow cytometric CAR persistence was detected out to 47 days post-infusion in this subject, with remission maintained for 3 months post-infusion. The results demonstrate safe, feasible, and clinically active anti-CD22 CAR T-cell therapy in subjects having undergone (and having become non-responsive to, e.g., due to epitope/antigen loss) previous anti-CD19 CAR therapy.

TABLE 4

Treatment response

| ID | Maximum CAR expansion (flow) | | | CRS | Best Response |
| --- | --- | --- | --- | --- | --- |
| | PB | Marrow | CSF | | |
| 1 | 0 | 0 | n/a | None | PD |
| 2 | 52.3% | 19.5% | 0% | Gr 1 | MRD neg CR |
| 3 | 73% | 36% | 32% | Gr 1 | SD |
| 4 | 6% | 1% | 0% | Gr 2 | SD |
| 5 | 0% | 1.3% | 0% | None | PD |
| 6 | 1.8% | 2% | 0% | None | PD |

PB: peripheral blood;
CSF: cerebrospinal fluid;
CRS: cytokine release syndrome;
PD: progressive disease:
MRD: minimal residual disease;
CR: complete remission;
SD: stable disease.

Example 6: Comparison of In Silico Analysis and In Vitro Binding of Peptides Derived from Junction Regions of a CAR for Binding to HLA Class II Actual binding affinities for certain HLA class II alleles (DPA1*01:03; DPB1*04:01, DRA*01:01; DRB1*03:01, DRA*01:01, DRB1*15:01, DRA*01:01; DRB1*11:01, DPA1*01:03; DPB1*04:02, DPA1*01:03; DPB1*03:01, DPA1*01:03; DPB1*01:01, DPA1*02:01; DPB1*01:01, DPA1*02:01; DPB1*04:02, DRA*01:01, DRB1*11:04, DRA*01:01, DRB1*01:02, and DPA1*02:01; DPB1*15:01) were assessed in vitro for exemplary overlapping 15 amino acid peptide sequences within a portion of the region spanning the junction between the CD28 and 4-1BB-derived sequences of the CAR described in Example 4. Specifically, assessment was of a series of overlapping 15-mer peptides derived from the sequence CYSLLVTVAFIIFW<u>VK</u>R-GRKKLLYIFKQPFMRPVQT (set forth in SEQ ID NO: 160), which contains a portion of the CD28-derived transmembrane domain and 4-1BB-derived costimulatory domain and spans the junction between the domains (bond joining the two amino acids noted in underline). In addition, a series of overlapping 15-mer peptides of each of a number of different variants of this portion also were assessed, each variant containing a mutation or mutations in this region as described in Example 2.

The various 15-mer overlapping peptides were synthesized and their purity tested by MALDI-TOF Mass Spectrometry. The synthetic peptides were then incubated with recombinant MHC molecules to assess binding properties using the REVEAL Epitope Discovery System as described in Example 3. Each peptide was separately tested for this ability with respect to each of the HLA class II alleles, normalized to the degree observed for a positive control (known T cell epitope for the relevant allele). A score was calculated for each allele, in which the binding was normalized to the positive control peptide set at 100%. The potential impact in the population based on these scores was calculated as the sum of the individual allele scores for each peptide.

Figure 7:
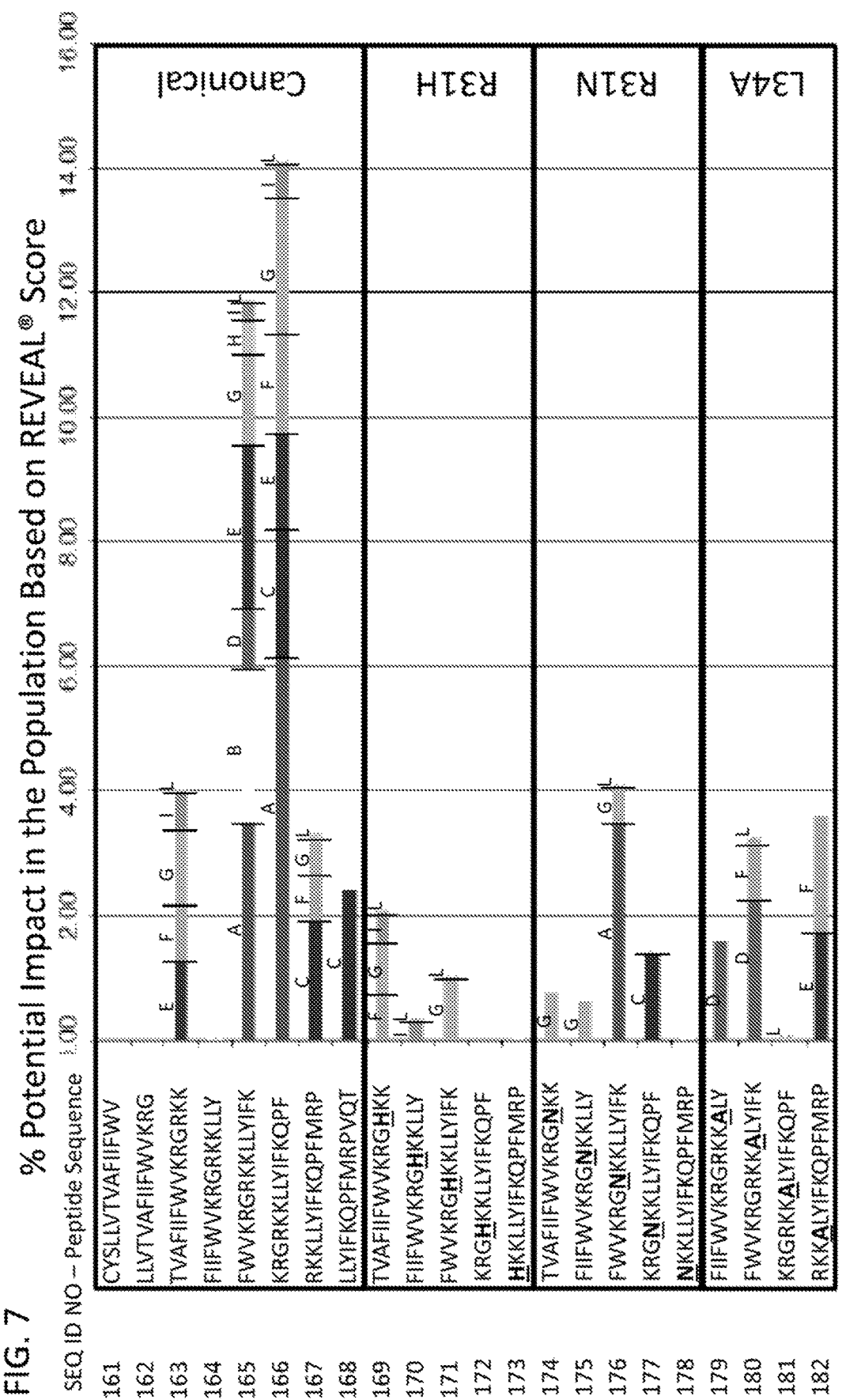
FIG. 7 shows the relative binding to various MHC Class II molecules of overlapping 15-mer peptides within a portion of the region spanning the junction between the CD28 and 4-1 BB-derived sequence (set forth in SEQ ID NO: 160; the canonical or "native" sequence) or within a corresponding portion containing either an R31H, R31N, or L34A substitution (with reference to numbering set forth in SEQ ID NO: 5). The REVEAL R score for binding is shown. The score of individual HLA class II alleles are individually labeled with a corresponding letter as follows: A: DPA1*01:03; DPB1*04:01; B: DRA*01:01; DRB1*03:01; C: DRA*01:01; DRB1*15:01; D: DRA*01:01; DRB1*11:01; E: DPA1*01:03; DPB1*04:02; F: DPA1*01:03; DPB1*03:01; G: DPA1*01:03; DPB1*01:01; H: DPA1*02:01; DPB1*01:01; I: DPA1*02:01; DPB1*04:02; J: DRA*01:01; DRB1*11:04; K: DRA*01:01; DRB1*01:02; and L: DPA1*02:01; DPB1*15:01.

The results are set forth in FIG. 7. As shown, the results demonstrated that modifications within the junction region resulted in successful reduction for HLA class II binding of at least one peptide within the region.

Figure 8:
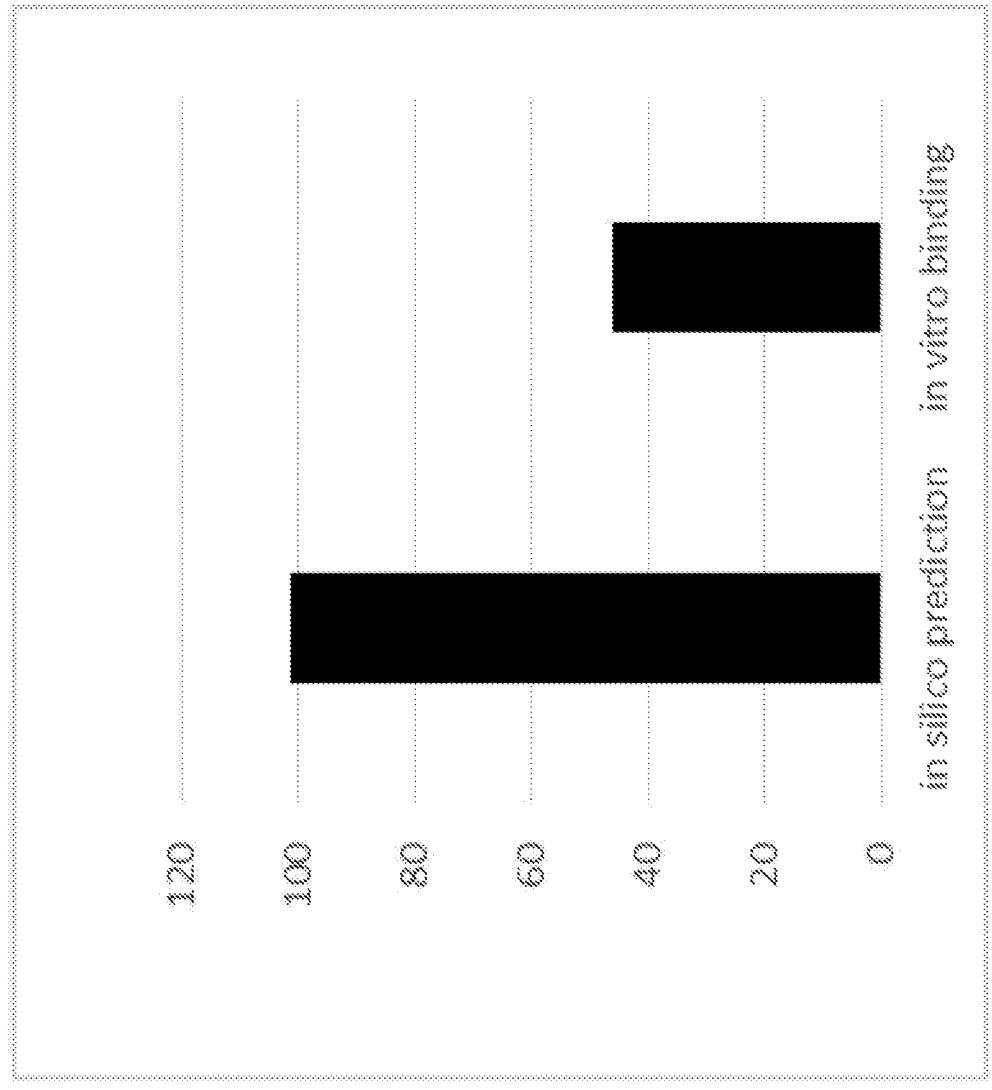
FIG. 8 shows a comparison of the in silico-predicted versus in vitro-determined binding of a 15-mer peptide from the CD28-4-1BB junction to an MHC Class II molecule.

For overlapping 15-mer peptides present within the native junction region, the results were compared to predicted binding (IC50) values obtained for binding of the same peptide:MHC complex, using the in silico prediction methods as described in Example 2. Since the maximum IC50 value predicted was about 50,000, the IC50 values were log transformed, subtracted from LOG(50000) and divided by LOG(50000) to obtain a normalized in silico score ((Log (50000)–log IC50)/Log(50000)). Immunogenicity scores (weighted based on relative frequency in the population of the individual HLA class II alleles) were obtained for the normalized in silico and actual binding affinities. The results are set forth in FIG. 8. In general, the in silico binding predictions were predictive of, and in some cases were over-predictive of, the actual in vitro binding results.

Example 7: Engineering and Characterization of T Cells Transduced with CARs Having Modified Junction Regions CAR-engineered T cells were generated by transduction of primary T cells with a lentiviral vector encoding either (1) the original chimeric antigen receptor (CAR) as described in Example 1, containing an anti-CD19 scFv, a hinge domain, the junction region set forth in SEQ ID NO: 5 (including a transmembrane domain derived from the native CD28 and an intracellular signaling domain derived from the native 4-1BB) (deemed the "native" junction region) and a CD3-zeta intracellular signaling domain or (2) one of a number of particular variants thereof, individually containing a modified junction region in which one or more mutations were introduced in the junction region spanning the junction between the CD28 transmembrane domain and 4-1BB costimulatory signaling domain. Each of the particular variant CARs contained a modified junction region having a mutation (with reference to SEQ ID NO:5) selected from among: K28Q/R31N/L34S, K28Q/R31N/L34A, R31N/L34S, R31N/L34A, K28Q/L34A, K28Q/R31S, K28Q/R31N, K28Q/R31A, L34S, L34A, R31S, R31N, R31A, K28S, K28Q, K28L, K28H, and K28A.

Primary human CD4+ and CD8+ T cells were isolated by immunoaffinity-based selection from human PBMC samples obtained from healthy donors. The resulting cells were stimulated by culturing with an anti-CD3/anti-CD28 reagent prior to engineering with the respective CAR. Cells were transduced using a lentiviral vector containing a nucleic acid molecule encoding the CAR and a nucleic acid encoding a truncated EGFR (EGFRt), for use as a surrogate marker for transduction, separated by a sequence encoding a T2A ribosome switch. A mock transduction was used as negative control. Transduced cells were used for expression analysis and cytolytic activity assay.

A. CAR Expression

Cell surface CAR expression (as indicated via the surrogate marker) was assessed at day 17 post-transduction with nucleic acid encoding the native CAR or each of the modified CARs. Cells were stained with anti-EGFR antibody to detect EGFRt as a surrogate to verify CAR expression and assessed by flow cytometry. CAR expression was similar in cells transduced to express the various variant CARs containing a modified junction region, and was comparable to expression of the CAR containing the native junction region.

B. Cytolytic Activity

Cells engineered to express the native or variant CARs were assessed for cytolytic activity against K562 target cells expressing the CD19 antigen (K562-CD19). The T cells were incubated with the target cells (K562-CD19) at various effector:target ratios (CAR:Target ratios of 1:1, 2:1 and 4:1) in a well of a culture plate. Lytic activity of the engineered T cells was assessed by measuring the number of caspase-positive target cells per well. The results showed that in this study, the T cells expressing the various variant CARs containing the modified junction region were able to kill CD19-expressing target cells in a target-specific manner, to a similar degree as T cells expressing the CAR containing the "native" junction region.

Example 8: Assessment of Surface Expression and Functionality of CARs Having Modified Junction Regions CAR-engineered T cells were generated by transduction of primary T cells with a nucleic acid encoding either (1) the original chimeric antigen receptor (CAR) described in Example 1 containing an anti-CD19 scFv, a hinge domain, the native junction region set forth in SEQ ID NO:5 (including a transmembrane domain derived from the native CD28 and an intracellular signaling domain derived from the native 4-1BB), or (2) a variant thereof containing a modified junction region having a mutation selected from among: K28L, R31H, L34A, or L34S with reference to SEQ ID NO:5. Cell surface CAR expression and functional properties of T cells engineered with CARs containing a modified junction region were assessed.

A. Surface Expression

To directly assess surface expression of the CARs, CAR-engineered T cells were stained with an anti-idiotype antibody specific for the anti-CD19 scFv contained in the CAR. The engineered cells also were assessed for surface expression of the surrogate marker EGFRt using an anti-EGFR antibody. To detect intracellular expression of the CARs, cells were first permeabilized and then stained under similar conditions using the anti-idiotype antibody and anti-EGFR antibody. Expression of the CAR and surrogate marker was analyzed by flow cytometry in CD4+ or CD8+ subsets.

Figure 9A:
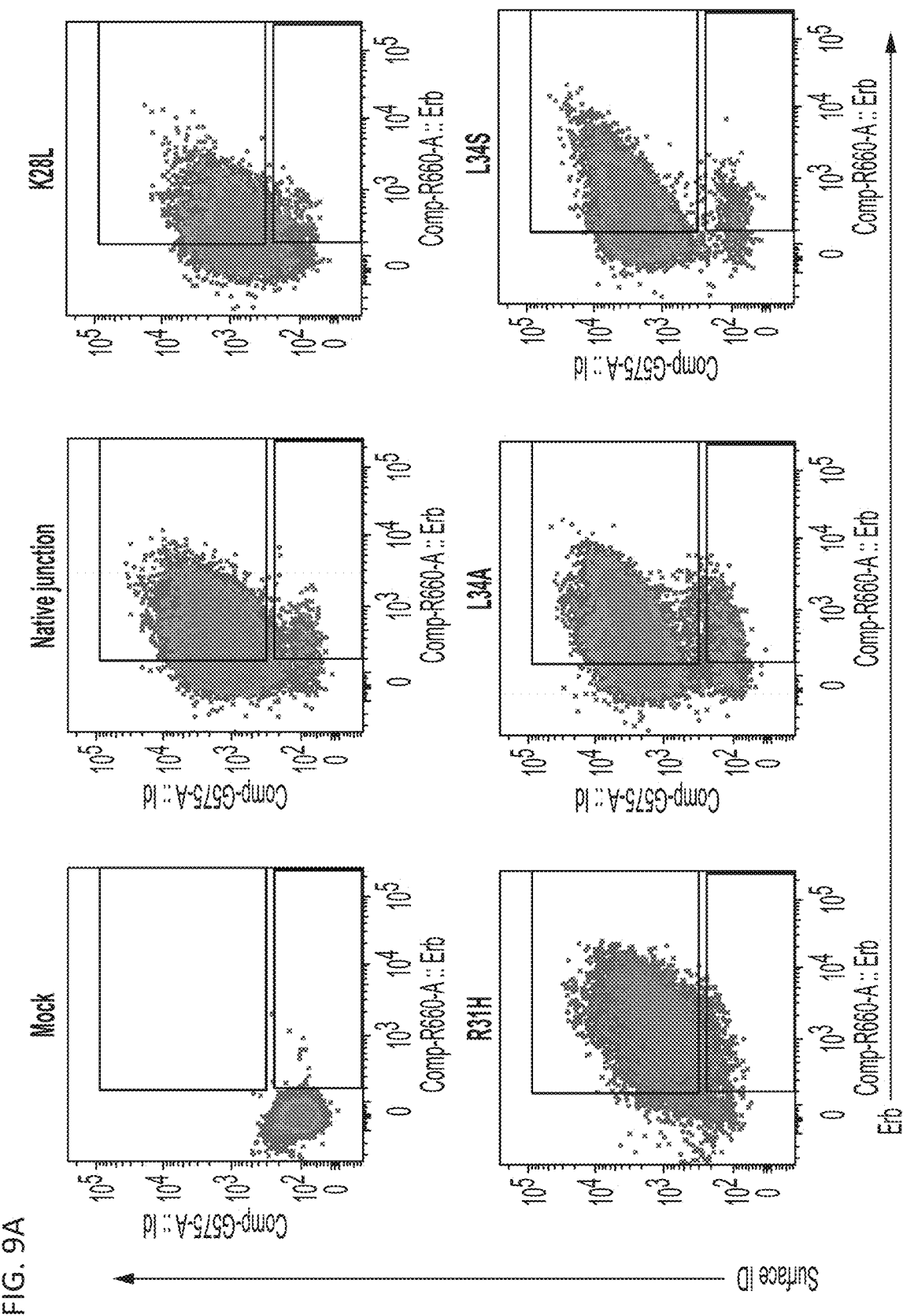
FIG. 9A and FIG. 9B show expression of the variant CARs containing a modified junction region on the surface and intracellularly, respectively, in engineered CD4+ T cells. The Y-axis depicts surface expression of the CAR by detection with an anti-idiotype antibody (Surface ID). The X-axis depicts surface expression of the surrogate EGFRt marker using an anti-EGFR antibody (Erb).
Figure 9B:
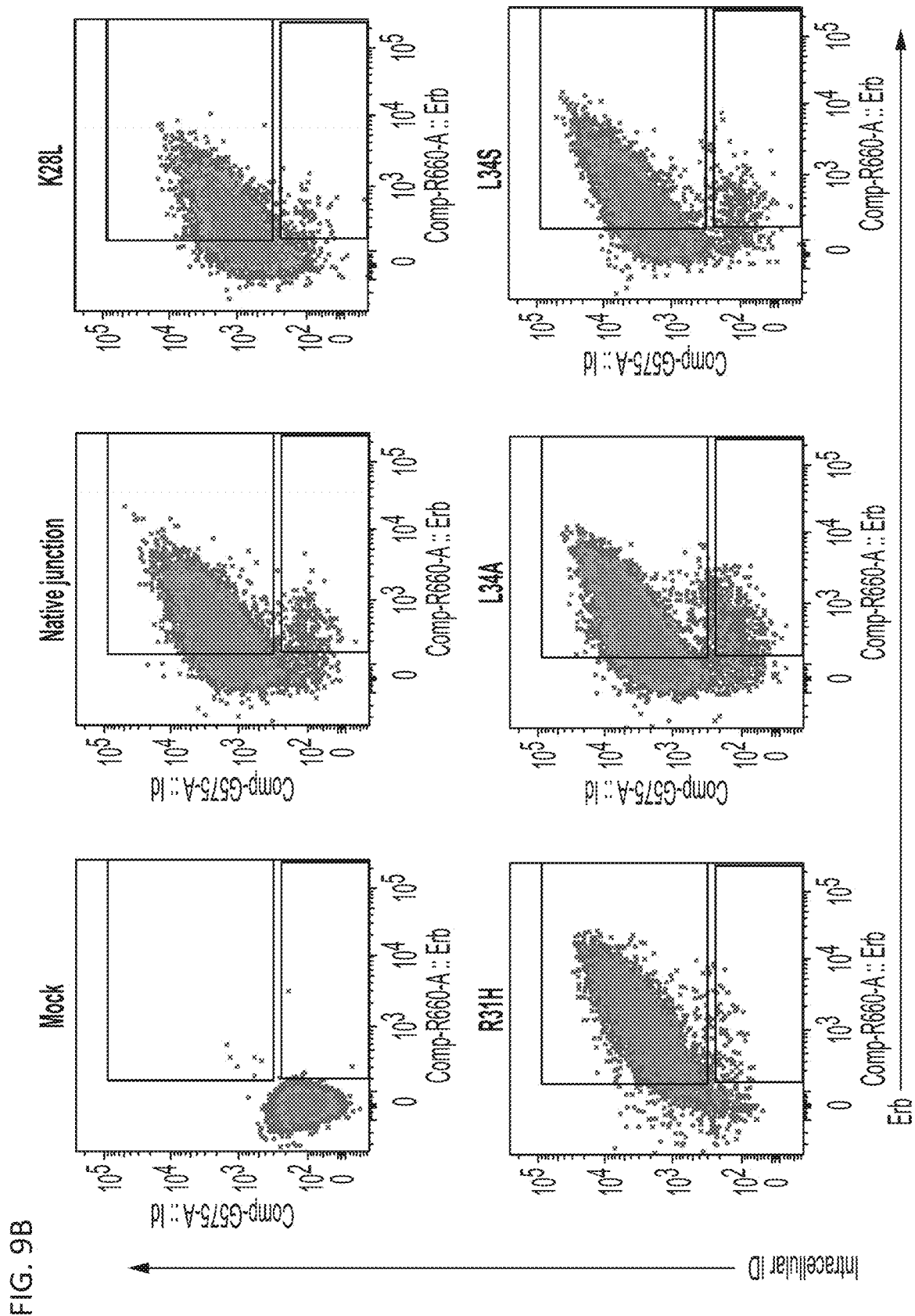

FIGS. 9A and 9B show that the variant CARs containing a modified junction region were expressed on the surface and intracellularly, respectively, in engineered CD4+ T cells. The level of surface expression of the variant CARs was similar or greater than the surface expression of the unmodified CAR containing the native junction region. The surrogate marker, which was co-transduced with the CARs, was expressed similarly in all engineered cells.

Figure 10:
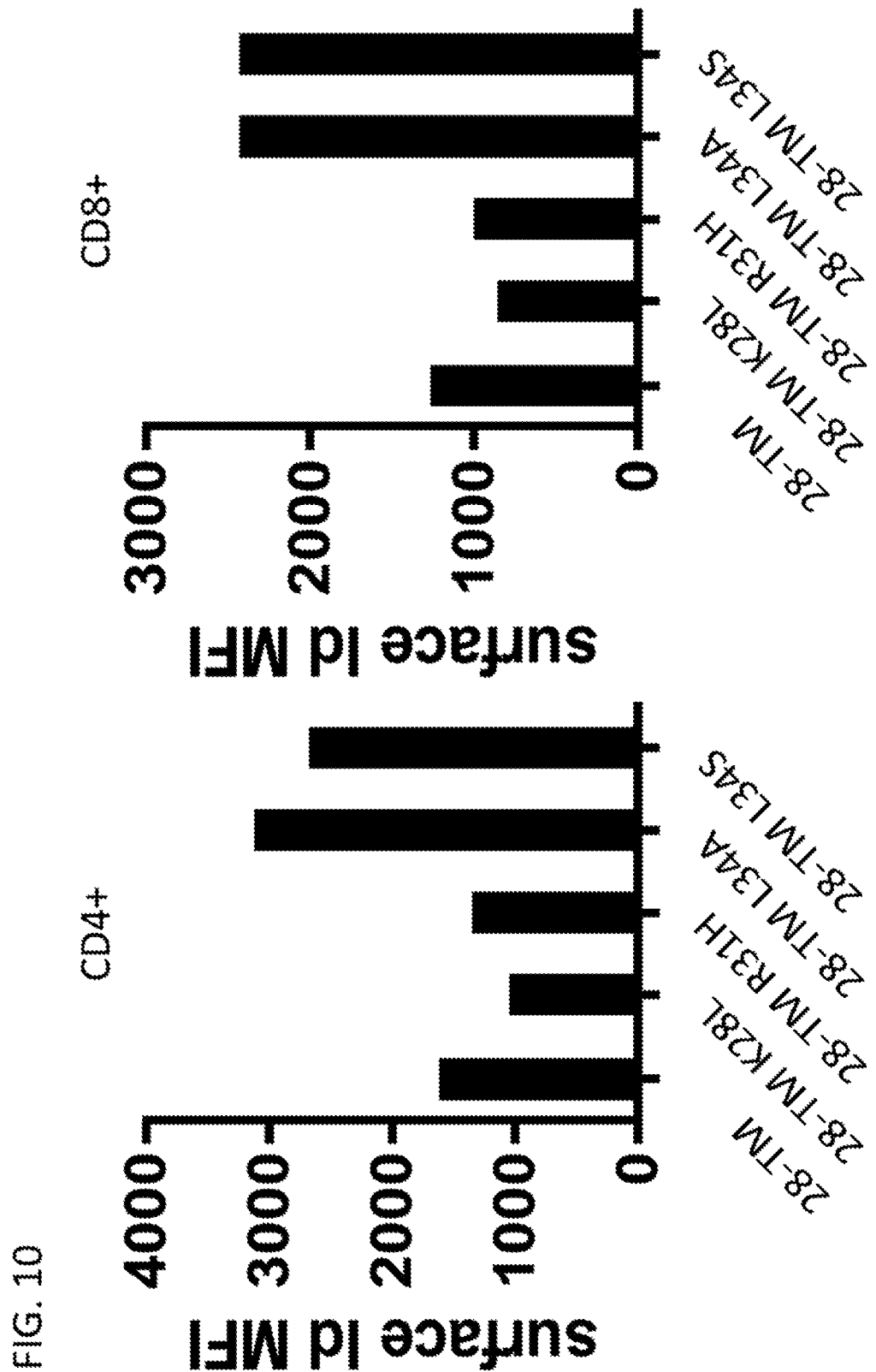
FIG. 10 shows mean fluorescence intensity (MFI) as determined by flow cytometry for surface expression of the CARs on both CD4+ and CD8+ T cells.

The mean fluorescence intensity (MFI) of CAR surface expression, as determined using the CAR-specific anti-idiotype antibody, was quantified in engineered T cells gated for CD4+ and CD8+ cells. As shown in FIG. 10, surface expression of the CARs was similar on both CD4+ and CD8+ T cells. Variant CARs containing a modified junction region having the L34A and L34S mutations exhibited increased surface expression as compared to the CAR with the native junction region.

B. Cytokine Expression

Figure 11:
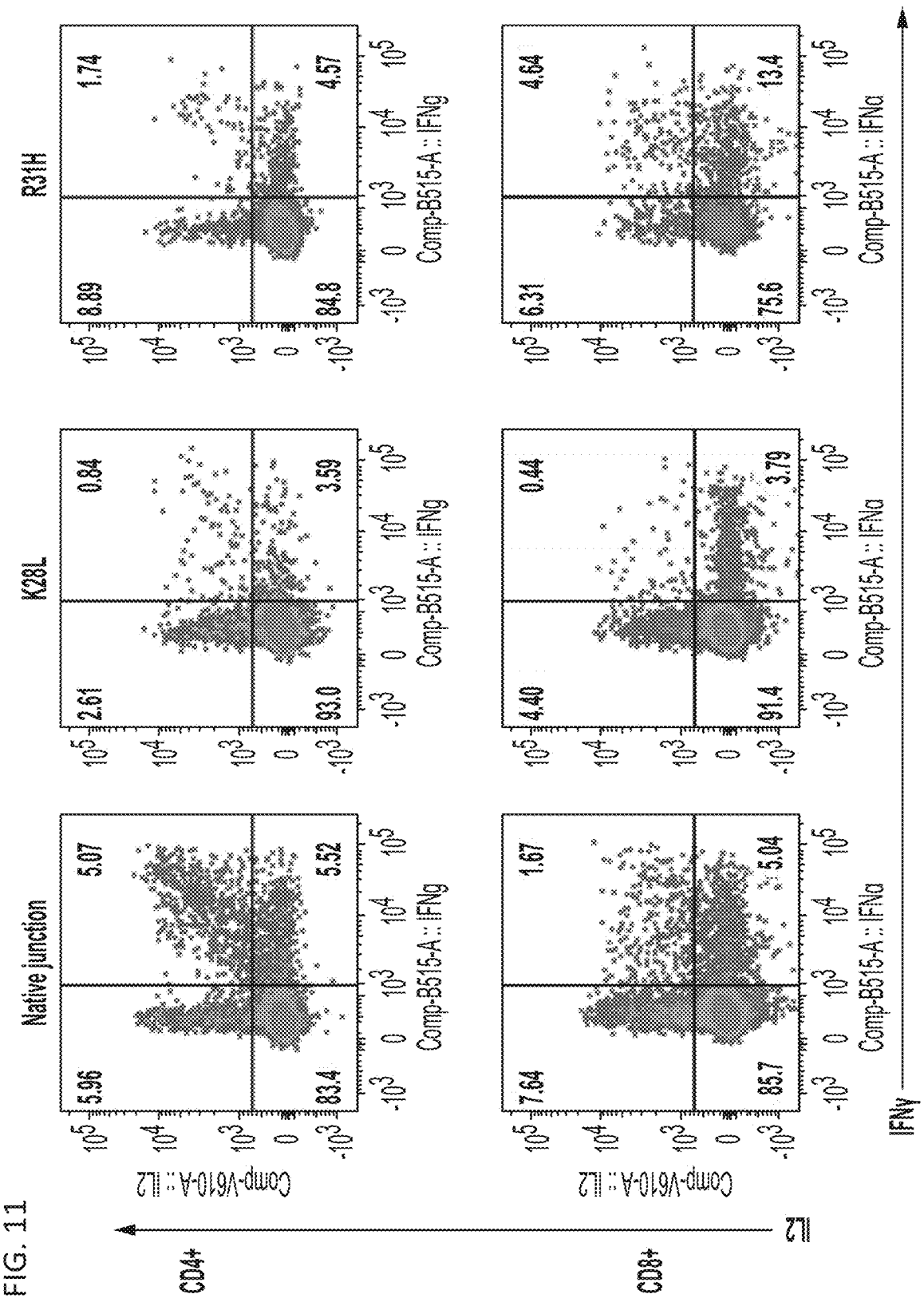
FIG. 11 shows flow cytometry plots depicting intracellular levels of IL-2 and IFN-γ in CD4+/CAR+ cells and CD8+/CAR+ cells.
Figure 11:
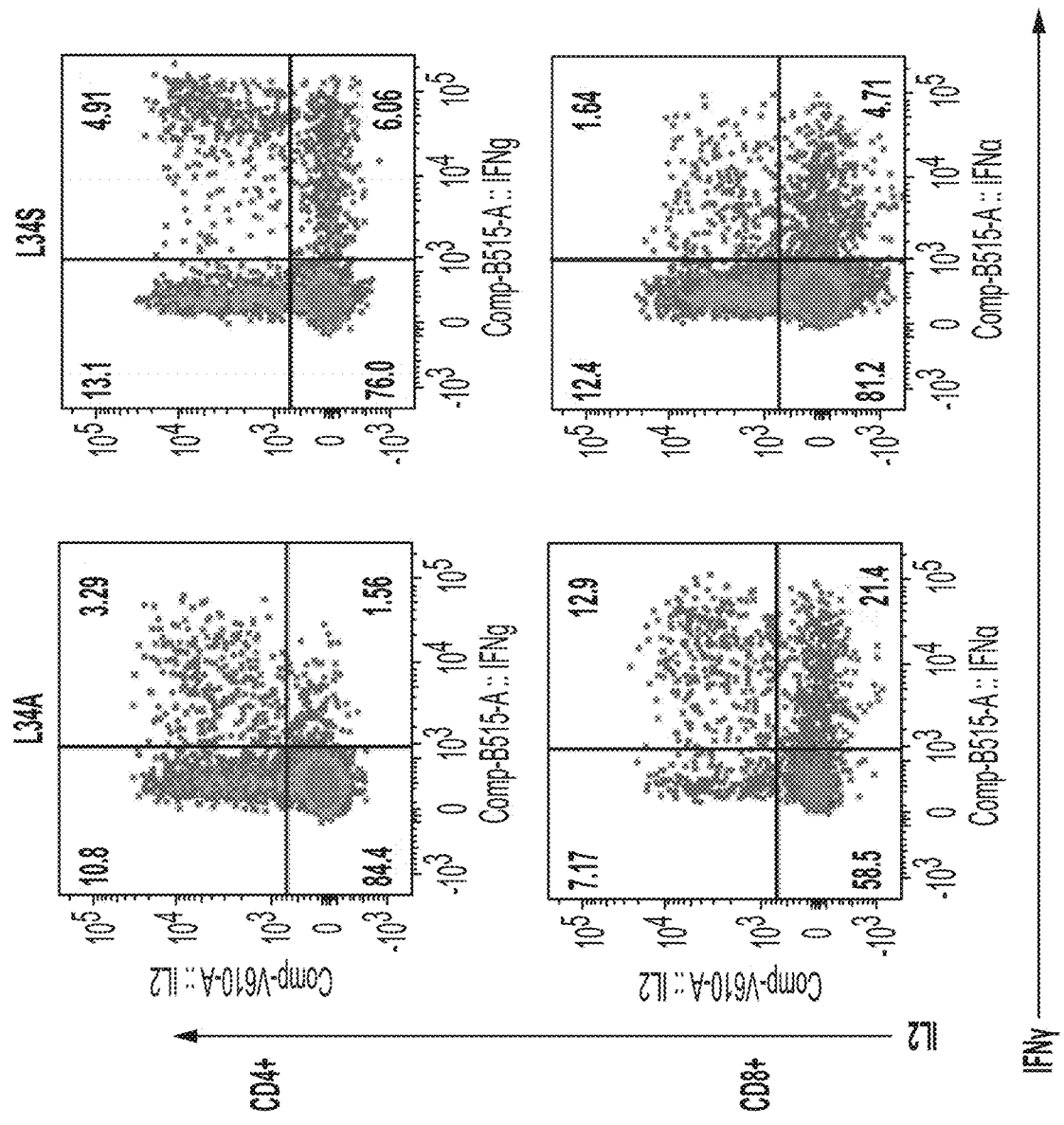

The production of cytokines by the anti-CD19 CAR T cells, expressing CARs containing either the native junction region or the various modified junction regions, was assessed. Engineered T cells were co-cultured with irradiated CD19-transduced K562 target cells (K562-CD19) or parental K562 cells not expressing the CD19 antigen in the presence of Golgi inhibitor. After stimulation, the cells were then fixed, permeabilized and intracellular IL-2 and IFN-γ cytokine levels were assessed by flow cytometry in CD4+/CAR+ cells and CD8+/CAR+ cells Exemplary flow cytometry plots depicting intracellular levels of IL-2 and IFN-γ in CD4+/CAR+ cells and CD8+/CAR+ cells are shown in FIG. 11. As shown, a greater percentage of CD4+/CAR+ T cells and CD8+/CAR+ T cells expressing the L34A and L34S variant CARs exhibited intracellular expression of IL-2 after antigen stimulation as compared to cells engineered with the unmodified CAR. A greater percentage of CD8+/CAR+ T cells expressing the R31H and L34A CAR variants had increased IFN-γ cytokine expression after antigen stimulation as compared to cells engineered with the unmodified CAR. Without wishing to be bound by theory, the increased level of cytokine expression may roughly correlate with the higher surface expression observed for the R31H and L34A variant CARs.

C. CAR T Cell Expansion

The ability of cells to expand ex vivo following repeated stimulations in some aspects can indicate capacity of CAR-T cells to persist (e.g. following initial activation) and/or is indicative of function in vivo (Zhao et al. (2015) Cancer Cell, 28:415-28). CAR-T cells were generated as described above and cultured with irradiated target cells (K562-CD19). Cells were stimulated, harvested every 3-4 days and counted, and restimulated with new target cells using the same culture conditions after resetting cell number to initial seeding density for each round. A total of 5 rounds of stimulation during a 17 day culture period were carried out. For each round of stimulation, the number of cells was determined.

Figure 12:
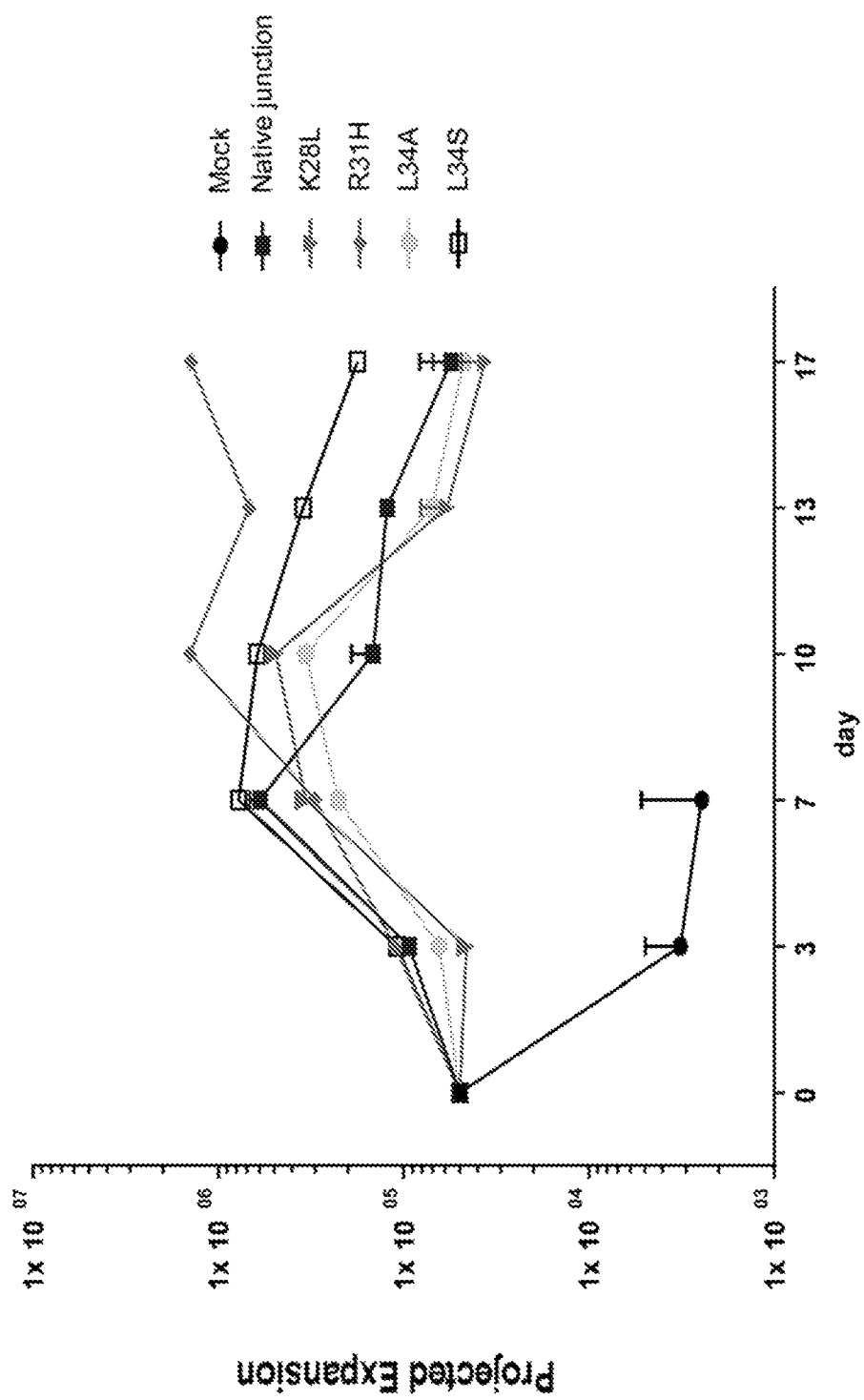
FIG. 12 shows expansion in a serial re-stimulation assay of the anti-CD19 CAR-engineered cells expressing variant CARs containing a modified junction region as compared to cells expressing the CAR with the native junction region.

As shown in FIG. 12, comparable initial growth of the anti-CD19 CAR-engineered cells was observed for cells expressing variant CARs containing a modified junction region as compared to cells expressing the CAR with the native junction region. After day 7 of restimulation, the degree of cell expansion declined in cells expressing the CAR containing the native junction region, whereas the variant CARs exhibited continued or similar expansion until at least day 10 of restimulation.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 5

Sequences

| SEQ ID NO | Sequence | Note |
|---|---|---|
| 1 | ESKYGPPCPPCP | IgG4 hinge |
| 2 | FWVLVVVGGVLACYSLLVTVAFIIFWV | CD28 transmembrane domain |
| 3 | KRGRKKLLYIFKQPFMRPVQTTQEEDGCSCRFPEEEEGGCEL | 4-1BB costimulatory domain (amino acids 214-255 of Q07011.1) *Homo sapien* |
| 4 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3-zeta intracellular signaling domain |
| 5 | FWVLVVVGGVLACYSLLVTVAFIIFWVKRGRKKLLYIFKQPFMRPVQTTQEEDGCSCRFPEEEEGGCEL | CD28-4-1BB |
| 6 | CYSLLVTVAFIIFWVKRGRKKLLYIFKQPF | Peptide |
| 7 | VAFIIFWVKRGRKKLL | Peptide |
| 8 | AFIIFWVKRGRKKLL | Peptide |
| 9 | FWVKRGRKKLLYIFK | Peptide |
| 10 | FIIFWVKRGRKKLL | Peptide |
| 11 | FIIFWVKRGRKKL | Peptide |
| 12 | IIFWVKRGRKKLL | Peptide |
| 13 | CYSLLVTVAFIIFWVNNKRGRKKLLYIFKQPF | Variant junction region |
| 14 | IIFWVNNKRGRKKL | Variant peptide |
| 15 | IIFWVNNKRGRKK | Variant peptide |
| 16 | VAFIIFWVK | Synthetic peptide |
| 17 | AFIIFWVKR | Synthetic peptide |
| 18 | FIIFWVKRG | Synthetic peptide |
| 19 | IIFWVKRGR | Synthetic peptide |
| 20 | IFWVKRGRK | Synthetic peptide |
| 21 | FWVKRGRKK | Synthetic peptide |
| 22 | WVKRGRKKL | Synthetic peptide |
| 23 | VAFIIFWVS | Synthetic peptide K28S |
| 24 | AFIIFWVSR | Synthetic peptide K28S |
| 25 | FIIFWVSRG | Synthetic peptide K28S |
| 26 | IIFWVSRGR | Synthetic peptide K28S |
| 27 | IFWVSRGRK | Synthetic peptide K28S |
| 28 | FWVSRGRKK | Synthetic peptide K28S |
| 29 | WVSRGRKKL | Synthetic peptide K28S |
| 30 | VAFIIFWVL | Synthetic peptide K28L |

TABLE 5-continued

Sequences

| SEQ ID NO | Sequence | Note |
|---|---|---|
| 31 | AFIIFWVLR | Synthetic peptide K28L |
| 32 | FIIFWVLRG | Synthetic peptide K28L |
| 33 | IIFWVLRGR | Synthetic peptide K28L |
| 34 | IFWVLRGRK | Synthetic peptide K28L |
| 35 | FWVLRGRKK | Synthetic peptide K28L |
| 36 | WVLRGRKKL | Synthetic peptide K28L |
| 37 | VAFIIFWVH | Synthetic peptide K28H |
| 38 | AFIIFWVHR | Synthetic peptide K28H |
| 39 | FIIFWVHRG | Synthetic peptide K28H |
| 40 | IIFWVHRGR | Synthetic peptide K28H |
| 41 | IFWVHRGRK | Synthetic peptide K28H |
| 42 | FWVHRGRKK | Synthetic peptide K28H |
| 43 | WVHRGRKKL | Synthetic peptide K28H |
| 44 | VAFIIFWVA | Synthetic peptide K28A |
| 45 | AFIIFWVAR | Synthetic peptide K28A |
| 46 | IIFWVARGR | Synthetic peptide K28A |
| 47 | IFWVARGRK | Synthetic peptide K28A |
| 48 | FWVARGRKK | Synthetic peptide K28A |
| 49 | WVARGRKKL | Synthetic peptide K28A |
| 50 | VAFIIFWVQ | Synthetic peptide K28Q |
| 51 | AFIIFWVQR | Synthetic peptide K28Q |
| 52 | FIIFWVQRG | Synthetic peptide K28Q |
| 53 | IIFWVQRGR | Synthetic peptide K28Q |
| 54 | IFWVQRGRK | Synthetic peptide K28Q |
| 55 | FWVQRGRKK | Synthetic peptide K28Q |

TABLE 5-continued

Sequences

| SEQ ID NO | Sequence | Note |
|---|---|---|
| 56 | WVQRGRKKL | Synthetic peptide K28Q |
| 57 | IIFWVKRGS | Synthetic peptide R31S |
| 58 | IFWVKRGSK | Synthetic peptide R31S |
| 59 | FWVKRGSKK | Synthetic peptide R31S |
| 60 | WVKRGSKKL | Synthetic peptide R31S |
| 61 | IIFWVKRGL | Synthetic peptide R31L |
| 62 | IFWVKRGLK | Synthetic peptide R31L |
| 63 | FWVKRGLKK | Synthetic peptide R31L |
| 64 | WVKRGLKKL | Synthetic peptide R31L |
| 65 | IIFWVKRGH | Synthetic peptide R31H |
| 66 | IFWVKRGHK | Synthetic peptide R31H |
| 67 | FWVKRGHKK | Synthetic peptide R31H |
| 68 | WVKRGHKKL | Synthetic peptide R31H |
| 69 | IIFWVKRGA | Synthetic peptide R31A |
| 70 | IFWVKRGAK | Synthetic peptide R31A |
| 71 | FWVKRGAKK | Synthetic peptide R31A |
| 72 | WVKRGAKKL | Synthetic peptide R31A |
| 73 | IIFWVKRGN | Synthetic peptide R31N |
| 74 | IFWVKRGNK | Synthetic peptide R31N |
| 75 | FWVKRGNKK | Synthetic peptide R31N |
| 76 | WVKRGNKKL | Synthetic peptide R31N |
| 77 | IIFWVQRGS | Synthetic peptide K28Q/R31S |
| 78 | IFWVQRGSK | Synthetic peptide K28Q/R31S |
| 79 | FWVQRGSKK | Synthetic peptide K28Q/R31S |
| 80 | WVQRGSKKL | Synthetic peptide K28Q/R31S |

TABLE 5-continued

Sequences

| SEQ ID NO | Sequence | Note |
|---|---|---|
| 81 | IIFWVQRGA | Synthetic peptide K28Q/R31A |
| 82 | IFWVQRGAK | Synthetic peptide K28Q/R31A |
| 83 | FWVQRGAKK | Synthetic peptide K28Q/R31A |
| 84 | WVQRGAKKL | Synthetic peptide K28Q/R31A |
| 85 | IIFWVQRGN | Synthetic peptide K28Q/R31N |
| 86 | IFWVQRGNK | Synthetic peptide K28Q/R31N |
| 87 | FWVQRGNKK | Synthetic peptide K28Q/R31N |
| 88 | WVQRGNKKL | Synthetic peptide K28Q/R31N |
| 89 | WVKRGRKKS | Synthetic peptide L34S |
| 90 | WVKRGRKKA | Synthetic peptide L34A |
| 91 | WVQRGNKKS | Synthetic peptide K28Q/L34S |
| 92 | WVQRGNKKA | Synthetic peptide K28Q/L34A |
| 93 | MGNSCYNIVATLLLVLNFERTRSLQDPCSNCPAGTFCDNNRNQICSPCP PNSFSSAGGQRTCDICRQCKGVFRTRKECSSTSNAECDCTPGFHCLGAG CSMCEQDCKQGQELTKKGCKDCCFGTFNDQKRGICRPWTNCSLDGKSVL VNGTKERDVVCGPSPADLSPGASSVTPPAPAREPGHSPQIISFFLALTS TALLFLLFFLTLRFSVVKRGRKKLLYIFKQPFMRPVQTTQEEDGCSCRF PEEEEGGCEL | 4-1BB costimulatory domain (Accession No. Q07011.1) Homo sapien |
| 94 | MLRLLLALNLFPSIQVTGNKILVKQSPMLVAYDNAVNLSCKYSYNLFSR EFRASLHKGLDSAVEVCVVYGNYSQQLQVYSKTGFNCDGKLGNESVTFY LQNLYVNQTDIYFCKIEVMYPPPYLDNEKSNGTIIHVKGKHLCPSPLFP GPSKPFWVLVVVGGVLACYSLLVTVAFIIFWVRSKRSRLLHSDYMNMTP RRPGPTRKHYQPYAPPRDFAAYRS | CD28 transmembrane domain (Accession No. P10747) Homo sapien |
| 95 | MKWKALFTAAILQAQLPITEAQSFGLLDPKLCYLLDGILFIYGVILTAL FLRVKFSRSADAPAYQQGQNQLYNELNLGRREEYDVLDKRRGRDPEMGG KPQRRKNPQEGLYNELQKDKMAEAYSEIGMKGERRRGKGHDGLYQGLST ATKDTYDALHMQALPPR | CD3 zeta chain (Accession No. P20963) Homo sapien |
| 96 | FIIFWVNNKRGRKK | Synthetic peptide |
| 97 | IFWVNNKRGRKKLL | Synthetic peptide |
| 98 | FIIFWVNNKRGRKK | Synthetic peptide |
| 99 | IFWVNNKRGRKKLL | Synthetic peptide |
| 100 | VAFIIFWVR | Synthetic peptide K28R |
| 101 | AFIIFWVRR | Synthetic peptide K28R |
| 102 | FIIFWVARG | Synthetic peptide K28A |
| 103 | MFWVLVVVGGVLACYSLLVTVAFIIFWV | CD28 transmembrane domain (amino acids 153-179 of |

TABLE 5-continued

Sequences

| SEQ ID NO | Sequence | Note |
|---|---|---|
| | | Accession No. P10747) *Homo sapien* |
| 104 | IEVMYPPPYLDNEKSNGTIIHVKGKHLCPSPLFPGPSKPFWVLVVVGGV LACYSLLVTVAFIIFWV | CD28, including transmembrane (amino acids 114-179 of Accession No. P10747) *Homo sapien* |
| 105 | RVKFSRSAEPPAYQQGQNQLYNELNLGRREEYDVLDKRRGRDPEMGGKP RRKNPQEGLYNELQKDKMAEAYSEIGMKGERRRGKGHDGLY QGLSTATKDTYDALHMQALPPR | CD3 zeta *Homo sapien* |
| 106 | GAATCTAAGTACGGACCGCCCTGCCCCCCTTGCCCT | spacer (IgG4hinge) (nt) *homo sapien* |
| 107 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer *Homo sapien* |
| 108 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2—CH3 spacer *Homo sapien* |
| 109 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC EVSGFSPPNILLMWLEDQREVNTSGFAPARPPPQPGSTTFWAWSVLRVP APPSPQPATYTCVVSHEDSRTLLNASRSLEVSYVTDH | IgD-hinge-Fc *Homo sapien* |
| 110 | LEGGGEGRGSLLTCGDVEENPGPR | T2A artificial |
| 111 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR artificial |
| 112 | RSKRSRLLHSDYMNMTPRRPGPTRKHYQPYAPPRDFAAYRS | CD28 cytoplasmic domain (amino acids 180-220 of P10747) *Homo sapien* |
| 113 | RSKRSRGGHSDYMNMTPRRPGPTRKHYQPYAPPRDFAAYRS | CD28 cytoplasmic domain variant (LL to GG) *Homo sapien* |
| 114 | FWVLVVVGGVLACYSLLVTVAFIIFWVARGRKKLLYIFKQPFMRPVQTT QEEDGCSCRFPEEEEGGCEL | CD28-4-1BB K28A variant |
| 115 | FWVLVVVGGVLACYSLLVTVAFIIFWVHRGRKKLLYIFKQPFMRPVQTT QEEDGCSCRFPEEEEGGCEL | CD28-4-1BB K28H variant |
| 116 | FWVLVVVGGVLACYSLLVTVAFIIFWVLRGRKKLLYIFKQPFMRPVQTT QEEDGCSCRFPEEEEGGCEL | CD28-4-1BB K28L variant |
| 117 | FWVLVVVGGVLACYSLLVTVAFIIFWVQRGRKKLLYIFKQPFMRPVQTT QEEDGCSCRFPEEEEGGCEL | CD28-4-1BB K28Q variant |
| 118 | FWVLVVVGGVLACYSLLVTVAFIIFWVSRGRKKLLYIFKQPFMRPVQTT QEEDGCSCRFPEEEEGGCEL | CD28-4-1BB K28S variant |
| 119 | FWVLVVVGGVLACYSLLVTVAFIIFWVKRGAKKLLYIFKQPFMRPVQTT QEEDGCSCRFPEEEEGGCEL | CD28-4-1BB R31A variant |
| 120 | FWVLVVVGGVLACYSLLVTVAFIIFWVKRGHKKLLYIFKQPFMRPVQTT QEEDGCSCRFPEEEEGGCEL | CD28-4-1BB R31H variant |

TABLE 5-continued

Sequences

| SEQ ID NO | Sequence | Note |
|---|---|---|
| 121 | FWVLVVVGGVLACYSLLVTVAFIIFWVKRGLKKLLYIFKQPFMRPVQTTQEEDGCSCRFPEEEEGGCEL | CD28-4-1BB R31L variant |
| 122 | FWVLVVVGGVLACYSLLVTVAFIIFWVKRGNKKLLYIFKQPFMRPVQTTQEEDGCSCRFPEEEEGGCEL | CD28-4-1BB R31N variant |
| 123 | FWVLVVVGGVLACYSLLVTVAFIIFWVKRGRKKALYIFKQPFMRPVQTTQEEDGCSCRFPEEEEGGCEL | CD28-4-1BB L34A variant |
| 124 | FWVLVVVGGVLACYSLLVTVAFIIFWVKRGRKKSLYIFKQPFMRPVQTTQEEDGCSCRFPEEEEGGCEL | CD28-4-1BB L34S variant |
| 125 | FWVLVVVGGVLACYSLLVTVAFIIFWVQRGAKKLLYIFKQPFMRPVQTTQEEDGCSCRFPEEEEGGCEL | CD28-4-1BB K28Q/R31A variant |
| 126 | FWVLVVVGGVLACYSLLVTVAFIIFWVQRGNKKLLYIFKQPFMRPVQTTQEEDGCSCRFPEEEEGGCEL | CD28-4-1BB K28Q/R31N variant |
| 127 | FWVLVVVGGVLACYSLLVTVAFIIFWVQRGSKKLLYIFKQPFMRPVQTTQEEDGCSCRFPEEEEGGCEL | CD28-4-1BB K28Q/R31S variant |
| 128 | FWVLVVVGGVLACYSLLVTVAFIIFWVQRGRKKALYIFKQPFMRPVQTTQEEDGCSCRFPEEEEGGCEL | CD28-4-1BB K28Q/L34A variant |
| 129 | FWVLVVVGGVLACYSLLVTVAFIIFWVQRGRKKSLYIFKQPFMRPVQTTQEEDGCSCRFPEEEEGGCEL | CD28-4-1BB K28Q/L34S variant |
| 130 | FWVLVVVGGVLACYSLLVTVAFIIFWVKRGNKKALYIFKQPFMRPVQTTQEEDGCSCRFPEEEEGGCEL | CD28-4-1BB R31N/L34A variant |
| 131 | FWVLVVVGGVLACYSLLVTVAFIIFWVKRGNKKSLYIFKQPFMRPVQTTQEEDGCSCRFPEEEEGGCEL | CD28-4-1BB R31N/L34S variant |
| 132 | FWVLVVVGGVLACYSLLVTVAFIIFWVQRGNKKALYIFKQPFMRPVQTTQEEDGCSCRFPEEEEGGCEL | CD28-4-1BB K28Q/R31N/L34A variant |
| 133 | FWVLVVVGGVLACYSLLVTVAFIIFWVQRGNKKSLYIFKQPFMRPVQTTQEEDGCSCRFPEEEEGGCEL | CD28-4-1BB K28Q/R31N/L34S variant |
| 134 | FWVLVVVGGVLACYSLLVTVAFIIFWVNNKRGRKKLLYIFKQPFMRPVQTTQEEDGCSCRFPEEEEGGCEL | CD28-4-1BB with variant junction region with NN insertion |
| 135 | MFWVLVVVGGVLACYSLLVTVAFIIFWVKRGRKKLLYIFKQPFMRPVQTTQEEDGCSCRFPEEEEGGCEL | CD28-4-1BB |
| 136 | IEVMYPPPYLDNEKSNGTIIHVKGKHLCPSPLFPGPSKPFWVLVVVGGVLACYSLLVTVAFIIFWVKRGRKKLLYIFKQPFMRPVQTTQEEDGCSCRFPEEEEGGCEL | CD28-4-1BB |
| 137 | SLLVTVAFIIFWVKRGRKKLLYIFKQ | CD28-4-1BB junction region |
| 138 | SLLVTVAFIIFWVARGRKKLLYIFKQ | CD28-4-1BB junction region K14A variant |
| 139 | SLLVTVAFIIFWVHRGRKKLLYIFKQ | CD28-4-1BB junction region K14H variant |
| 140 | SLLVTVAFIIFWVLRGRKKLLYIFKQ | CD28-4-1BB junction region K14L variant |
| 141 | SLLVTVAFIIFWVQRGRKKLLYIFKQ | CD28-4-1BB junction region K14Q variant |
| 142 | SLLVTVAFIIFWVSRGRKKLLYIFKQ | CD28-4-1BB junction region K14S variant |
| 143 | SLLVTVAFIIFWVKRGAKKLLYIFKQ | CD28-4-1BB junction region R17A variant |

TABLE 5-continued

Sequences

| SEQ ID NO | Sequence | Note |
|---|---|---|
| 144 | SLLVTVAFIIFWVKRGHKKLLYIFKQ | CD28-4-1BB junction region R17H variant |
| 145 | SLLVTVAFIIFWVKRGLKKLLYIFKQ | CD28-4-1BB junction region R17L variant |
| 146 | SLLVTVAFIIFWVKRGNKKLLYIFKQ | CD28-4-1BB junction region R17N variant |
| 147 | SLLVTVAFIIFWVKRGRKKALYIFKQ | CD28-4-1BB junction region L20A variant |
| 148 | SLLVTVAFIIFWVKRGRKKSLYIFKQ | CD28-4-1BB junction region L20S variant |
| 149 | SLLVTVAFIIFWVQRGAKKLLYIFKQ | CD28-4-1BB junction region K14Q/R17A variant |
| 150 | SLLVTVAFIIFWVQRGNKKLLYIFKQ | CD28-4-1BB junction region K14Q/R17N variant |
| 151 | SLLVTVAFIIFWVQRGSKKLLYIFKQ | CD28-4-1BB junction region K14Q/R17S variant |
| 152 | SLLVTVAFIIFWVQRGRKKALYIFKQ | CD28-4-1BB junction region K14Q/L20A variant |
| 153 | SLLVTVAFIIFWVQRGRKKSLYIFKQ | CD28-4-1BB junction region K14Q/L20S variant |
| 154 | SLLVTVAFIIFWVKRGNKKALYIFKQ | CD28-4-1BB junction region R17N/L20A variant |
| 155 | SLLVTVAFIIFWVKRGNKKSLYIFKQ | CD28-4-1BB junction region R17N/L20S variant |
| 156 | SLLVTVAFIIFWVQRGNKKALYIFKQ | CD28-4-1BB junction region K14Q/R17N/L20A variant |
| 157 | SLLVTVAFIIFWVQRGNKKSLYIFKQ | CD28-4-1BB junction region K14Q/R17N/L20S variant |
| 158 | GAATCTAAGTACGGACCGCCCTGCCCCCCTTGCCCT | spacer (IgG4hinge) (nucleotide) *homo sapien* |
| 159 | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 Zeta |
| 160 | CYSLLVTVAFIIFWVKRGRKKLLYIFKQPFMRPVQT | peptide |
| 161 | CYSLLVTVAFIIFWV | Synthetic peptide |
| 162 | LLVTVAFIIFWVKRG | Synthetic peptide |
| 163 | TVAFIIFWVKRGRKK | Synthetic peptide |
| 164 | FIIFWVKRGRKKLLY | Synthetic peptide |
| 165 | FWVKRGRKKLLYIFK | Synthetic peptide |

TABLE 5-continued

Sequences

| SEQ ID NO | Sequence | Note |
|---|---|---|
| 166 | KRGRKKLLYIFKQPF | Synthetic peptide |
| 167 | RKKLLYIFKQPFMRP | Synthetic peptide |
| 168 | LLYIFKQPFMRPVQT | Synthetic peptide |
| 169 | TVAFIIFWVKRGHKK | Synthetic peptide R31H |
| 170 | FIIFWVKRGHKKLLY | Synthetic peptide R31H |
| 171 | FWVKRGHKKLLYIFK | Synthetic peptide R31H |
| 172 | KRGHKKLLYIFKQPF | Synthetic peptide R31H |
| 173 | HKKLLYIFKQPFMRP | Synthetic peptide R31H |
| 174 | TVAFIIFWVKRGNKK | Synthetic peptide R31N |
| 175 | FIIFWVKRGNKKLLY | Synthetic peptide R31N |
| 176 | FWVKRGNKKLLYIFK | Synthetic peptide R31N |
| 177 | KRGNKKLLYIFKQPF | Synthetic peptide R31N |
| 178 | NKKLLYIFKQPFMRP | Synthetic peptide R31N |
| 179 | FIIFWVKRGRKKALY | Synthetic peptide L34A |
| 180 | FWVKRGRKKALYIFK | Synthetic peptide L34A |
| 181 | KRGRKKALYIFKQPF | Synthetic peptide L34A |
| 182 | RKKALYIFKQPFMRP | Synthetic peptide L34A |
| 183 | FWVLVVVGGVLACYSLLVTVAFIIFWVKRGSKKLLYIFKQPFMRPVQTTQEEDGCSCRFPEEEEGGCEL | CD28-4-1BB R31S variant |
| 184 | SLLVTVAFIIFWVKRGSKKLLYIFKQ | CD28-4-1BB junction region R31S variant |

What is claimed:

1. An engineered T cell comprising a chimeric receptor, wherein the chimeric receptor comprises a CD28 transmembrane domain and a 4-1BB costimulatory signaling domain having one or more amino acid sequence modifications compared to a reference chimeric receptor comprising the sequence set forth in SEQ ID NO:5 wherein:
the CD28 transmembrane domain and the 4-1BB costimulatory signaling domain of the chimeric receptor together comprise a sequence of amino acids that exhibits at least 95% sequence identity to SEQ ID NO:5;
and wherein:
the one or more amino acid sequence modifications comprise an amino acid replacement(s) corresponding to replacement selected from among K28A, K28H, K28L, K28Q, K28L, K28Q, K28S, R31A, R31H, R31L, R31N, R31S, L34A and L34S, with reference to the numbering set forth in SEQ ID NO:5.

2. An engineered T cell comprising a chimeric receptor, wherein the chimeric receptor comprises a CD28 transmembrane domain and a 4-1BB costimulatory signaling domain having one or more amino acid sequence modifications compared to a reference chimeric receptor comprising the sequence set forth in SEQ ID NO:5, and wherein:
the one or more amino acid sequence modifications consist of an insertion of two asparagine (N) residues between amino acid residues 27 and 28 with reference to the numbering set forth in SEQ ID NO:5.

3. The engineered T cell of claim 1, wherein the CD28 transmembrane domain and the 4-1BB costimulatory signaling domain of the chimeric receptor together comprise a sequence of amino acids that exhibits at least 97% sequence identity to SEQ ID NO:5.

4. The engineered T cell of claim 1, wherein the amino acid replacement(s) are or correspond to amino acid replacements selected from among K28Q/R31A, K28Q/R31N, K28Q/R31S, K28Q/L34A, K28Q/L34S, R31N/L34A, R31N/L34S, K28Q/R31N/L34A, and K28Q/R31N/L34S.

5. The engineered T cell of claim 1, wherein the chimeric receptor comprises a modified junction region selected from among:
the sequence of amino acids set forth in any of SEQ ID NOS: 138-157.

6. The engineered T cell of claim 1, wherein the chimeric receptor comprises:
the sequence of amino acids set forth in any of SEQ ID NOS: 114-133.

7. The engineered T cell of claim 1, wherein:
the reference chimeric receptor comprises from its N to C terminus in order: an extracellular ligand-binding domain, the CD28 transmembrane domain, the 4-1BB intracellular costimulatory domain and an activating cytoplasmic signaling domain; and the chimeric receptor comprises from its N to C terminus in order: the extracellular ligand-binding domain, the CD28 transmembrane domain and the 4-1BB intracellular costimulatory domain having the one or more amino acid sequence modifications and the activating cytoplasmic signaling domain.

8. The engineered T cell of claim 7, wherein the ligand-binding domain is an antigen-binding domain comprising an antibody or an antibody fragment.

9. The engineered T cell of claim 8, wherein the antigen-binding domain is an antibody or an antibody fragment that is a single chain fragment.

10. The engineered T cell of claim 9, wherein the antibody fragment comprises an scFv.

11. The engineered T cell of claim 7, wherein the ligand-binding domain specifically binds an antigen that is associated with a disease or disorder.

12. The engineered T cell of claim 7, wherein the activating cytoplasmic domain comprises a T cell receptor (TCR) component and/or comprises an immunoreceptor tyrosine-based activation motif (ITAM).

13. The engineered T cell of claim 7, wherein the activating cytoplasmic signaling domain comprises a cytoplasmic signaling domain of a zeta chain of a CD3-zeta (CD3ζ) chain.

14. The engineered T cell of claim 2, wherein:
the reference chimeric receptor comprises from its N to C terminus in order: an extracellular ligand-binding domain, the CD28 transmembrane domain, the 4-1BB intracellular costimulatory domain and an activating cytoplasmic signaling domain; and
the chimeric receptor comprises from its N to C terminus in order: the extracellular ligand-binding domain, the CD28 transmembrane domain and the 4-1BB intracellular costimulatory domain having the one or more amino acid modifications, and the activating cytoplasmic signaling domain.

15. The engineered T cell of claim 14, wherein the extracellular ligand-binding domain comprises an scFv that specifically binds an antigen that is associated with a disease or disorder.

16. The engineered T cell of claim 14, wherein the activating cytoplasmic signaling domain comprises a cytoplasmic signaling domain of a zeta chain of a CD3-zeta (CD3ζ) chain.

17. An engineered T cell comprising a chimeric receptor, wherein the chimeric receptor comprises a CD28 transmembrane domain and a 4-1BB costimulatory signaling domain having one or more amino acid sequence modifications compared to a reference chimeric receptor comprising the sequence set forth in SEQ ID NO:5, and wherein the chimeric receptor comprises the sequence of amino acids set forth in SEQ ID NO:134.

18. The engineered T cell of claim 17, wherein:
the reference chimeric receptor comprises from its N to C terminus in order: an extracellular ligand-binding domain, the CD28 transmembrane domain, the 4-1BB intracellular costimulatory domain and an activating cytoplasmic signaling domain; and
the chimeric receptor comprises from its N to C terminus in order: the extracellular ligand-binding domain, the CD28 transmembrane domain and the 4-1BB intracellular costimulatory domain having the one or more amino acid modifications, and the activating cytoplasmic signaling domain.

19. The engineered T cell of claim 18, wherein the extracellular ligand-binding domain comprises an scFv that specifically binds an antigen that is associated with a disease or disorder.

20. The engineered T cell of claim 18, wherein the activating cytoplasmic signaling domain comprises a cytoplasmic signaling domain of a zeta chain of a CD3-zeta (CD3ζ) chain.

* * * * *